United States Patent
Green et al.

(10) Patent No.: US 11,970,542 B2
(45) Date of Patent: Apr. 30, 2024

(54) BISPECIFIC ANTIBODIES SPECIFIC FOR TREATING HEMATOLOGICAL MALIGNANCIES

(71) Applicants: FRED HUTCHINSON CANCER CENTER, Seattle, WA (US); Massachusetts Institute of Technology, Cambridge, MA (US)

(72) Inventors: Damian J. Green, Seattle, WA (US); Yukang Lin, Issaquah, WA (US); Oliver W. Press, Seattle, WA (US); Alice Tzeng, Beachwood, OH (US); Karl Dane Wittrup, Boston, MA (US)

(73) Assignees: Fred Hutchinson Cancer Center, Seattle, WA (US); Massachusetts Institute of Technology, Cambridge, MA (US)

( * ) Notice: Subject to any disclaimer, the term of this patent is extended or adjusted under 35 U.S.C. 154(b) by 689 days.

(21) Appl. No.: 16/762,410

(22) PCT Filed: Nov. 8, 2018

(86) PCT No.: PCT/US2018/059872
§ 371 (c)(1),
(2) Date: May 7, 2020

(87) PCT Pub. No.: WO2019/094626
PCT Pub. Date: May 16, 2019

(65) Prior Publication Data
US 2021/0171651 A1   Jun. 10, 2021

Related U.S. Application Data

(60) Provisional application No. 62/583,414, filed on Nov. 8, 2017.

(51) Int. Cl.
| | |
|---|---|
| *A61K 39/395* | (2006.01) |
| *A61K 31/203* | (2006.01) |
| *A61K 45/06* | (2006.01) |
| *A61K 51/04* | (2006.01) |
| *A61P 35/00* | (2006.01) |
| *C07K 16/28* | (2006.01) |
| *C07K 16/44* | (2006.01) |
| *A61K 39/00* | (2006.01) |

(52) U.S. Cl.
CPC ........ *C07K 16/2896* (2013.01); *A61K 31/203* (2013.01); *A61K 39/3955* (2013.01); *A61K 45/06* (2013.01); *A61K 51/0482* (2013.01); *A61P 35/00* (2018.01); *C07K 16/2878* (2013.01); *C07K 16/44* (2013.01); *A61K 2039/505* (2013.01); *C07K 2317/31* (2013.01); *C07K 2317/622* (2013.01)

(58) Field of Classification Search
None
See application file for complete search history.

(56) References Cited

U.S. PATENT DOCUMENTS

2017/0107295 A1   4/2017  Lokhorst et al.

FOREIGN PATENT DOCUMENTS

| WO | 01/74384 A1 | 10/2001 |
| WO | 2009/082624 A2 | 7/2009 |
| WO | 2010/0099536 A2 | 9/2010 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Green, D.J., et al., "Comparative Analysis of Bispecific Antibody and Streptavidin-Targeted Radioimmunotherapy for B-Cell Cancers," Cancer Research 76(22): 6669-6679, Nov. 2016, 12 pages.
International Search Report dated Apr. 1, 2019, issued in corresponding International Application No. PCT/US2018/059872, filed Nov. 8, 2018, 6 pages.
Written Opinion dated Apr. 1, 2019, issued in corresponding International Application No. PCT/US2018/059872, filed Nov. 8, 2018, 10 pages.

* cited by examiner

*Primary Examiner* — Christine J Saoud
*Assistant Examiner* — Jon M Lockard
(74) *Attorney, Agent, or Firm* — Christensen O'Connor Johnson Kindness PLLC

(57) ABSTRACT

The present disclosure provides compositions and methods for improved pre-targeted radioimmunotherapeutics (PRIT) to treat various hematological disorders, such as B cell hyperproliferative disorders and solid tumors. The disclosed compositions include bispecific antibody compositions having a first domain that specifically bind to an antigen such as CD38, BCMA, Muc1, GPRC5D, or Slam7, and a second domain that specifically binds to a radioactive ligand. Methods include administering the disclosed bispecific antibody reagent and separately administering the radioactive ligand. In some embodiments, a clearing agent is also administered. In some embodiments, the therapeutic methods comprise administering a combination of two or more bispecific antibody reagents. In some embodiments, an enhancing agent, such as ATRA, gamma secretase inhibitor, or dextramethasone, is also administered to enhance expression of the target antigen on the target cells.

7 Claims, 18 Drawing Sheets
Specification includes a Sequence Listing.

BISPECIFIC ANTIBODIES SPECIFIC FOR TREATING HEMATOLOGICAL MALIGNANCIES

CROSS-REFERENCE TO RELATED APPLICATION

This application is a national stage of International Application No. PCT/US2018/059872, filed Nov. 8, 2018, which claims the benefit of U.S. Application No. 62/583,414, filed Nov. 8, 2017, the disclosures of which are hereby expressly incorporated herein by reference in their entireties.

STATEMENT OF GOVERNMENT LICENSE RIGHTS

This invention was made with government support under CA205248 awarded by the National Institutes of Health. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 67150_Sequence_Listing_final.txt. The text file is 242,145 bytes; was created on Nov. 8, 2018; and is being submitted electronically via Patent Center with the filing of the specification.

BACKGROUND

Effective agents and therapeutic strategies have been developed in hematological oncology over the past decade to improve cancer patient outcomes.

For example, effective agents have been introduced to make complete response (CR) to induction therapy possible in almost half of multiple myeloma (MM) patients. However, complete disease eradication often remains elusive, creating conditions that strongly favor the persistence and evolution of therapy resistant malignant plasma cell clones. As a result the vast majority of the 130,000 people in the United States living with MM will ultimately die of progressive disease. High dose chemotherapy followed by autologous stem cell transplantation (ASCT) increases CR rates and prolongs disease-free survival, and the number of ASCTs for MM increases annually, emphasizing the importance of ASCT in current treatment paradigms. Yet disease almost invariably recurs even after ASCT.

Radioimmunotherapy (RIT) promises critical improvements in cancer therapy compared to strategies such as ASCT. RIT is less toxic to the patient than ASCT and provides the potential to completely eradicate disease. For illustration, in the context of MM the radiosensitivity of malignant plasma cells outside of the bone marrow (BM) is well documented in clinical settings. Local recurrence of solitary extramedullary plasmacytomas occurs in less than 10% of cases after external beam radiotherapy (RT) alone, and sustained local disease control and durable symptom relief has been reported for 98% of lesions receiving >10 Gy. Furthermore, this excellent efficacy of external beam RT for extramedullary plasmacytomas occurs even in patients with poor risk cytogenetics and active MM, suggesting that targeted RIT is agnostic to certain high risk features.

RIT selectively delivers radiation to target cells at disseminated disease sites, facilitating escalation to radiation doses not achievable through external beam RT. The efficacy of RIT is well-established for several hematologic malignancies, and has been successfully integrated into ASCT-conditioning regimens with a significant improvement in progression free survival and overall survival among patients with non-Hodgkin lymphoma (NHL) and acute myeloid leukemia (AML) when targeting CD20 and CD45 antigens, respectively.

However, few studies have examined RIT in MM and none have explored pretargeted radioimmunotherapy (PRIT), a two-step process shown in the clinic to be markedly superior to conventional, single-step RIT. In conventional RIT, a targeting antibody is directly labeled with a radioactive molecule. In two-step PRIT, a non-radioactive targeting antibody is administered first and allowed to localize to tumor sites. The second step, after this "cold" antibody has maximally accumulated in the tumor, is to administer a low molecular weight radioactive moiety with a high affinity for the antibody. The small size of the second reagent facilitates rapid tumor penetration, rapid capture and retention by the pre-targeted antibody, and rapid clearance of unbound radioactive molecules from the blood. This two-step approach greatly decreases radiation absorption by healthy tissues. The efficacy of PRIT can be further amplified by administering a "clearing agent" (CA) prior to the radioactive reagent. The CA accelerates clearance of any unbound antibody from the bloodstream, greatly reducing the chance of radioactive molecules attaching to unbound antibody and, thus reducing incidence of offsite toxicity.

CD38 is a transmembrane glycoprotein with high surface density and uniform expression on MM and NHL cells, and relatively low expression on normal myeloid and lymphoid cells, and has proven a successful target for mAb-based immunotherapy in MM. Unlike many surface antigens, CD38 is stable on the cell surface, and this trait combined with high density and uniform expression in MM and NHL make CD38 an excellent target for PRIT. The inventors recently documented striking therapeutic efficacy of PRIT in MM xenograft models using anti-CD38-streptavidin (OKT10-SA) and the β-emitter $^{90}$Y labeled biotin. Objective remissions were observed within 7 days in 100% of mice treated with 800 to 1200 μCi of CD38-SA PRIT, including 100% complete remissions (i.e., having no detectable tumor in treated mice compared to tumors in control mice that were 2982±1002% of initial tumor volume) by day 23. Despite these dramatic results obtained with the PRIT approach, concerns remain, including immunogenicity of bacterially-derived streptavidin used to confer high binding affinity between the antigen targeting antibody reagent and the radioactive moiety. Furthermore, the presence of endogenous biotin can lower efficacy by blocking binding of radiolabeled biotin to the cancer-bound, streptavidin-labeled antibody reagent.

Accordingly, despite the advances in the art, a need remains for effective therapeutic reagents and methods that effectively target and eradicate cancers such as hematological malignancies, while avoiding issues of immunogenicity, off-site toxicity, and endogenous interference of the radiolabel. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a bispecific affinity reagent, comprising:
a first binding domain that specifically binds to a target antigen selected from CD38, B cell maturation antigen (BCMA), Muc1, GPRC5D, and SlamF7; and a second binding domain that specifically binds to a radioactive ligand.

In another aspect, the disclosure provides a method of treating a hematological malignancy in a subject. The method comprises administering to the subject a therapeutically effective amount of a bispecific affinity reagent disclosed herein, and thereafter administering to the subject a therapeutically effective amount of a radioactive ligand. In some embodiments, the method further comprises administering an enhancer, such as ATRA, GSI, or dextramethasone.

In another aspect, the disclosure provides a method of treating a hematological malignancy in a subject. The method comprises:
administering to the subject a therapeutically effective amount of a first bispecific affinity reagent and a therapeutically effective amount of a second bispecific affinity reagent, and thereafter
administering to the subject a therapeutically effective amount of a radioactive ligand;
wherein the first bispecific affinity reagent and the second bispecific affinity reagent each comprises a first binding domain that specifically binds to a cancer antigen and a second binding domain that specifically binds to the radioactive ligand,
wherein the first binding domain of the first bispecific affinity reagent and the first binding domain of the second bispecific affinity reagent specifically bind to different cancer antigens selected from CD38, BCMA, Muc1, SlamF7, GPRC5D, and CD20.

In another aspect, the disclosure provides a method of treating a malignancy characterized by expression of CD38. The method comprises:
administering to the subject an amount of all trans retinoic acid (ATRA), or functional derivatives or subunits thereof, sufficient to upregulate expression of CD38 in the malignant cells,
administering to the subject a therapeutically effective amount of a bispecific affinity reagent comprising a first binding domain that specifically binds to CD38 and a second binding domain that specifically binds to a radioactive ligand, and thereafter
administering to the subject a therapeutically effective amount of a radioactive ligand.

In another aspect, the disclosure provides a method of treating a malignancy characterized by expression of GPRC5D. The method comprises:
administering to the subject an amount of all trans retinoic acid (ATRA), or functional derivatives or subunits thereof, sufficient to upregulate expression of GPRC5D in the malignant cells,
administering to the subject a therapeutically effective amount of a bispecific affinity reagent comprising a first binding domain that specifically binds to GPRC5D and a second binding domain that specifically binds to a radioactive ligand, and thereafter
administering to the subject a therapeutically effective amount of a radioactive ligand.

In some embodiments, of the above aspects, the ATRA or functional derivatives or subunits thereof are administered in a liposomal formulation.

In another aspect, the disclosure provides a method of treating a malignancy characterized by expression of BCMA. The method comprises:
administering to the subject an amount of gamma secretase inhibitor (GSI) sufficient to upregulate expression of BCMA in the malignant cells,
administering to the subject a therapeutically effective amount of a bispecific affinity reagent comprising a first binding domain that specifically binds to BCMA and a second binding domain that specifically binds to a radioactive ligand, and thereafter
administering to the subject a therapeutically effective amount of a radioactive ligand.

In another aspect, the disclosure provides a method of treating a malignancy characterized by expression of Muc1. The method comprises:
administering to the subject an amount of gamma secretase inhibitor (GSI) sufficient to upregulate expression of Muc1 in the malignant cells,
administering to the subject a therapeutically effective amount of a bispecific affinity reagent comprising a first binding domain that specifically binds to Muc1 and a second binding domain that specifically binds to a radioactive ligand, and thereafter
administering to the subject a therapeutically effective amount of a radioactive ligand.

In some embodiments, the disclosed methods can further comprise administering an effective amount of a clearing agent (CA) after administering the bispecific affinity reagent and before administering the radioactive ligand. In some embodiments, the disclosed radioactive moiety comprises yttrium DOTA. In some embodiments, the disclosed affinity reagent is a fusion protein and the first binding domain and the second binding domain are separated by a hinge region. In some embodiments, the disclosed hinge region is or comprises a construct selected from an IgG1 Fc fragment, an IgG2 Fc fragment, and IgG3 Fc fragment, and an IgG4 Fc fragment. In some embodiments, the one or both of the disclosed first binding domain and the second binding domain are an antibody, a functional antibody fragment, functional antibody derivative. In some embodiments, the one or both of the disclosed first binding domain and the second binding domain comprise a variable light chain domain and variable heavy chain domain. In some embodiments, the disclosed variable light chain and variable heavy chain of the binding domain and/or the second binding are separated by a linker domain. In some embodiments, the one or both of the first binding domain and the second binding domain is an scFv. In some embodiments, the disclosed scFv is humanized.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1E. Structure and characterization of the CD38 bispecific protein. (1A) Schematic of the 028-Fc-C825 bispecific (anti-CD38 x anti-Y-DOTA) Fc fusion gene. An anti-human CD38 028 scFv gene and an yttrium-DOTA capturing C825 disulfide-stabilized scFv (ds-scFv) gene were fused to the human IgG1 Fc fragment at the amino and carboxyl ends, respectively. An N-linked glycosylation containing linker (NLG) was incorporated between the Fc and C825 ds-scFv domains, as shown. Relevant restriction enzymes for cloning and linearization are indicated. (Schematic not drawn to scale). (1B) SDS-PAGE analysis of the 028-Fc-C825 fusion protein. Bispecific 028-Fc-C825 fusion polypeptides were expressed in CHO-DG44 cells, where they spontaneously formed dimers via the hinge regions and were secreted into the growth medium. The purification fractions and the 028-Fc-C825 fusion protein (5 μg) were analyzed by electrophoresis on a 4-20% MES SDS PAGE gel (Invitrogen). Lane 1: SeeBlue Plus2 marker proteins in kDa (Invitrogen); Lane 2: Culture supernatant; Lane 3: Protein A column flow-through; Lane 4: wash; Lane 5: the non-reduced 028-Fc-C825 fusion protein (samples boiled); Lane 7: the monomeric 028-Fc-C825 fusion protein (samples boiled and reduced with 2-mercaptoethanol); Lane 6 is empty. The gel was stained with Coomassie blue. (1C) Sandwich ELISA assay demonstrating concentration-dependent binding of the CD38 (028-Fc-C825) bispecific protein to the Y-DOTA ligand. A 96-well plate was coated with 70 μL of the BSA-Y-DOTA conjugate (1 μg/mL in PBS) and then blocked with 200 μL of 2% BSA in PBS buffer. After washing, the wells were treated with 100 μL of bispecific protein at 16 μg/mL followed by serial dilution as indicated. The plate was further treated with HRP-anti-human Fc antibody followed by 3,3',5,5'-Tetramethylbenzidine (TMB). Controls demonstrate that binding to Y-DOTA is dependent on the C825 portion of the bispecific protein: the positive control, CD20 2H7-Fc-C825 bispecific, shows binding to Y-DOTA while the negative control, fusion protein-Fc without C825, shows a lack of binding. (1D) and (1E) bifunctional binding assays of the CD38 (028-Fc-C825) bispecific protein demonstrate targeted binding to CD38+ cells and ligand capture of Y-DOTA-biotin. (1D) CD38+ multiple myeloma target cells (H929) or (E) CD38- control cells (U266) ($0.5 \times 10^6$) were incubated in 40 μL of HBSS-2% FBS buffer containing 1 μg of biotin-Y-DOTA ligand and 2 μg of either CD38 or CD20 bispecific proteins, or no protein for 30 min at 4° C. For CD38 blocking controls, cells were pre-incubated for 30 min in buffer containing 40 μg anti-CD38 Ab. Cells were finally washed and resuspended in 40 μL buffer plus 2 μL of PE-streptavidin, incubated 30 min at 4° C., washed 3 times, resuspended in 500 μL of PBS buffer containing 1% formaldehyde, and analyzed by flow cytometry.

Figure 8:
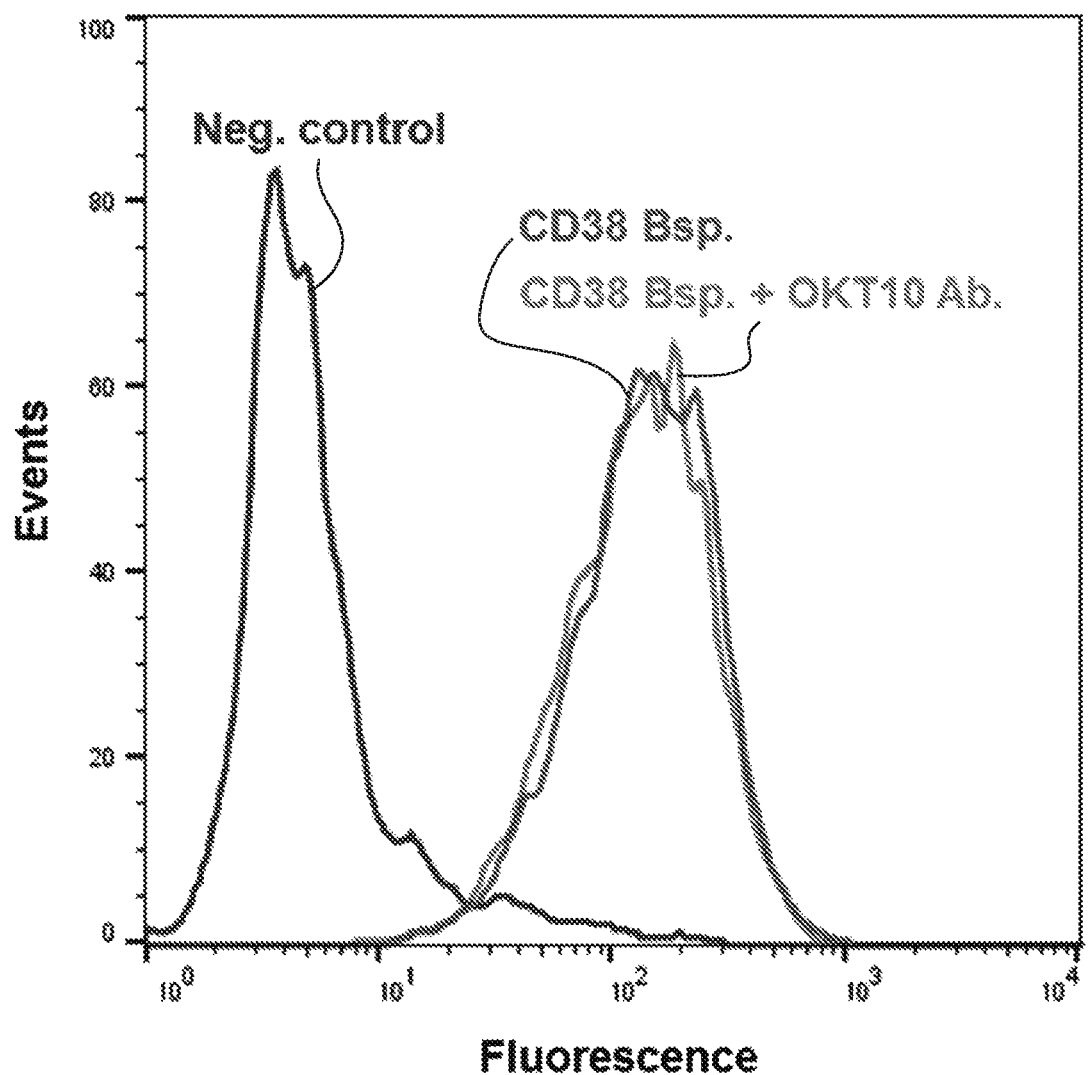

FIG. 8. Flow cytometry demonstrates that the CD38 Ab OKT10, used in CD38-SA PRIT experiments, fails to block targeted binding of the CD38 bispecific to CD38+ cells (H929). CD38+ target cells (H929) (Red and Green) or CD38-control cells (U266) (Blue) (0.5×10$^6$) were incubated in 40 μL of HBSS-2% FBS buffer containing 1 μg of biotin-Y-DOTA ligand and 2 μg of CD38 bispecific protein for 30 min at 4° C. For blocking test (Green), cells were pre-incubated for 30 min in buffer containing 40 μg CD38 Ab OKT10. After bispecific incubation, cells were washed, resuspended in 40 μL buffer plus 2 μL of PE-streptavidin, incubated 30 min at 4° C., washed 3 times, resuspended in 500 μL of PBS buffer containing 1% formaldehyde, and analyzed by flow cytometry.

Figure 9A:
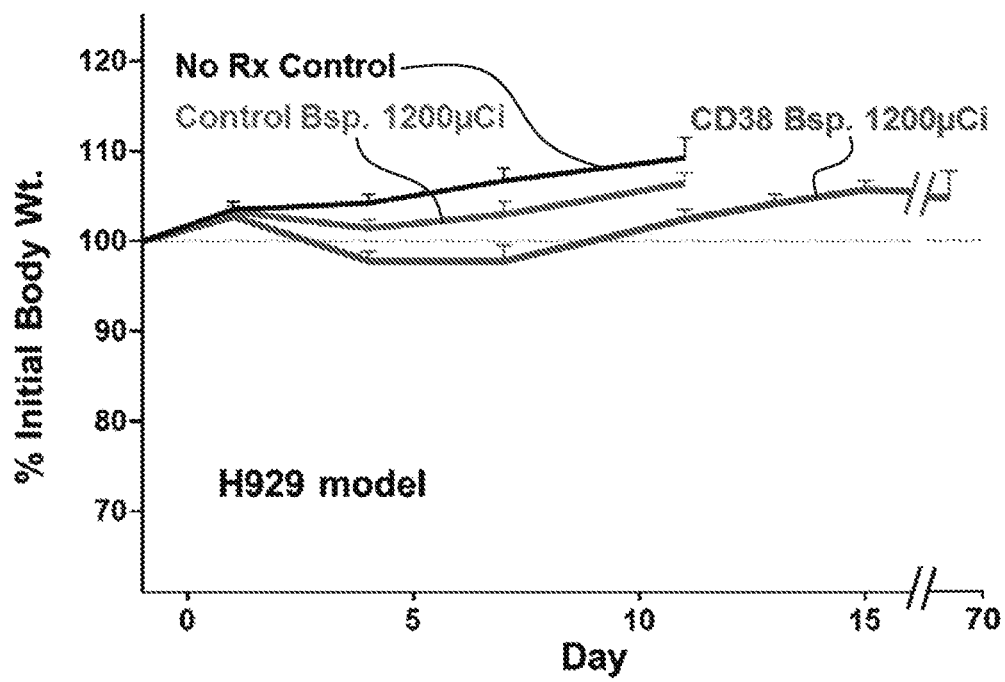
Figure 9B:
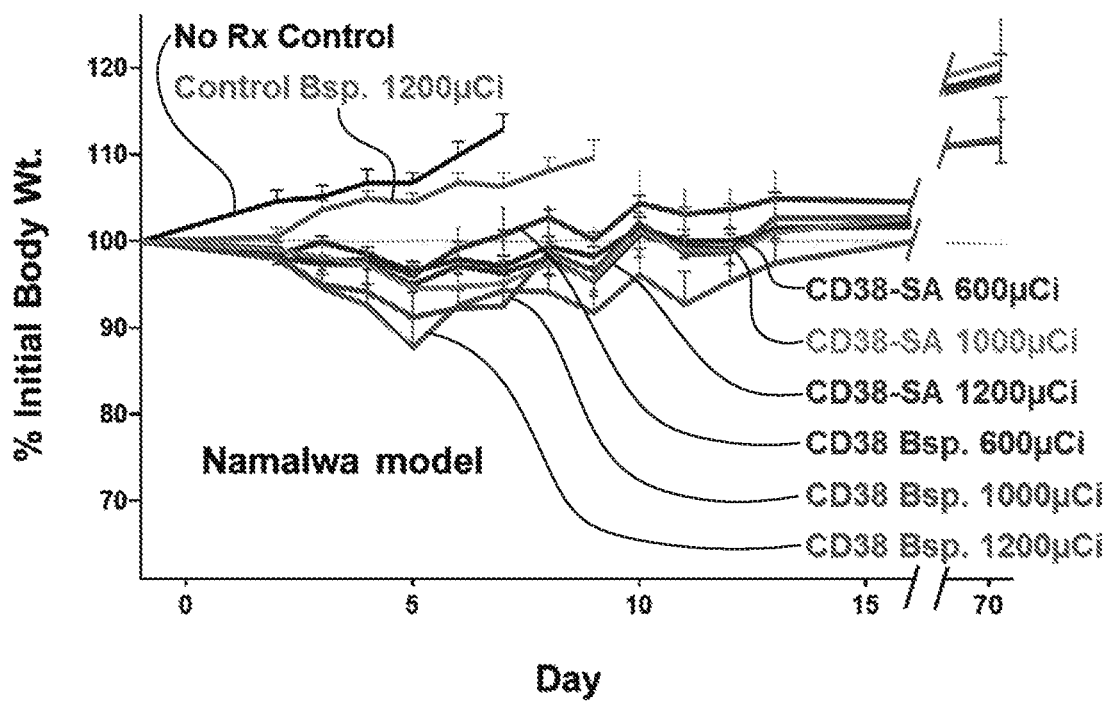
Figure 9C:
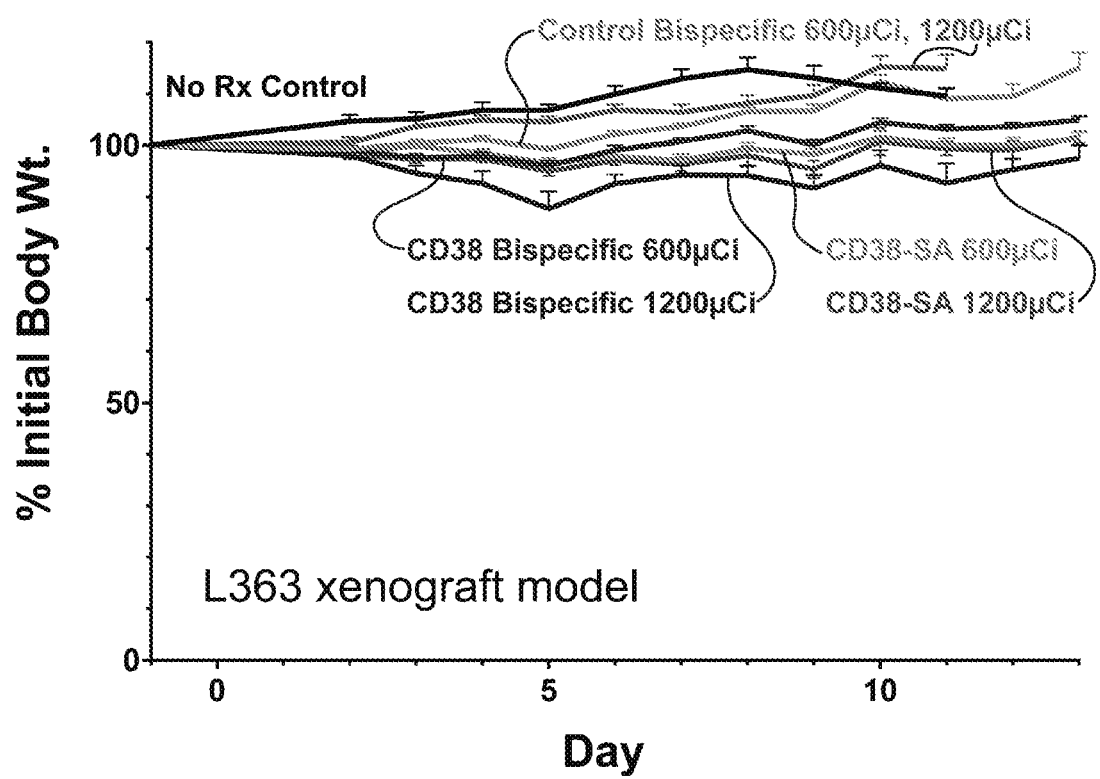

FIGS. 9A-9C. Effect of CD38 bispecific PRIT on body weights of mice bearing H929 (MM), Namalwa (BL), or L363 (MM) xenografts. Athymic nude mice (n=8-10 per group) with (9A) H929, (9B) Namalwa, or (9C) L363 xenografts were injected at −24 hrs with a pretargeting protein (CD38 bispecific, CD38-SA, or control [anti-CD20] bispecific), then at −1 hr with CA, and at 0 hrs with 600, 1000 or 1200 μCi $^{90}$Y-DOTA-Biotin. Body weights and tumor volumes were monitored three times weekly and mice euthanized when tumor size reached IACUC mandated limits.

FIGS. 10A-10D. (10A) Sandwich ELISA assay demonstrating concentration-dependent binding of the CD38 and BCMA bispecific FPs to microtiter wells coated with the Y-DOTA ligand. (10B) Flow Cytometric Analysis of Binding of purified CD38 bispecific fusion protein to H929 MM cells. (10C) Flow Cytometric Analysis of Binding of purified BCMA bispecific fusion protein to H929 MM cells with, or without, gamma secretase inhibition (GSI). A control bispecific fusion molecule not targeting BCMA was also tested. (10D) Comparison of survival of athymic mice bearing subcutaneous H929 (MM) xenografts treated with bispecific antibody PRIT.

FIGS. 11A-11D. Dose dependent effect of the gamma secretase inhibitor, R04929097, on BCMA expression on 4 MM cell lines (11A, 11B) and 7 primary MM samples (11C, 11D). (11A) Surface BCMA expression by MM.1R cells cultured with the indicated concentrations of R04929097; staining with anti-BCMA antibody (black lines) compared to isotype control (grey line). (11B) Fold-change in surface BCMA expression by MM cell lines when cultured with the indicated concentrations of R04929097; fold change indicated relative to untreated MM cells of the same line. (11C) Surface BCMA expression by primary patient MM cells cultured with the indicated concentrations of R04929097. Staining was as described in regard to FIG. 11A. (11D) Fold change in BCMA on primary myeloma cells (n=7) cultured with vary amounts of GSI for 4 h. Primary and cell lines were cultured at 0.5×10$^6$ cells/mL. Fold change in BCMA is defined as Treated (MFIBCMA-MFIiso)/Control (MFIBCMA-MFIiso). Data is representative of 3 independent experiments with T cells derived from different donors.

Figure 12:
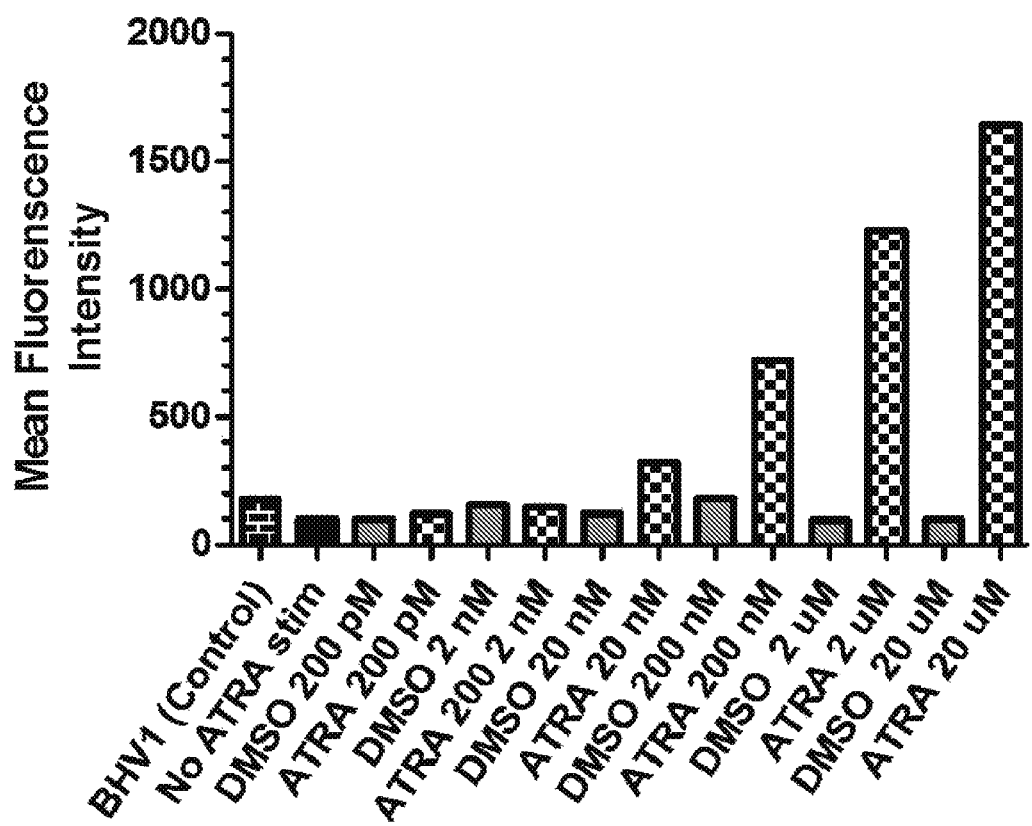

FIG. 12. To identify a physiologically relevant range of all-trans-retinoic acid (ATRA) doses capable of increasing CD38 receptor expression in MM cell lines, a series of in vitro experiments were performed and confirmed a dose dependent increase in CD38 receptor express ion in three MM cell lines (U266, H929 and L363). These studies generated data to refine the process of manipulating CD38 receptor density for the purpose of increasing targeted delivery of radiolabeled DOTA-biotin after CD38 tumor cell pretargeting. A key outcome was that the effect on the U266 MM line was particularly notable because, while constitutive expression of CD38 is low on these cells, a striking dose dependent increase in expression is observed after incubation with solubilized ATRA.

Figure 13:
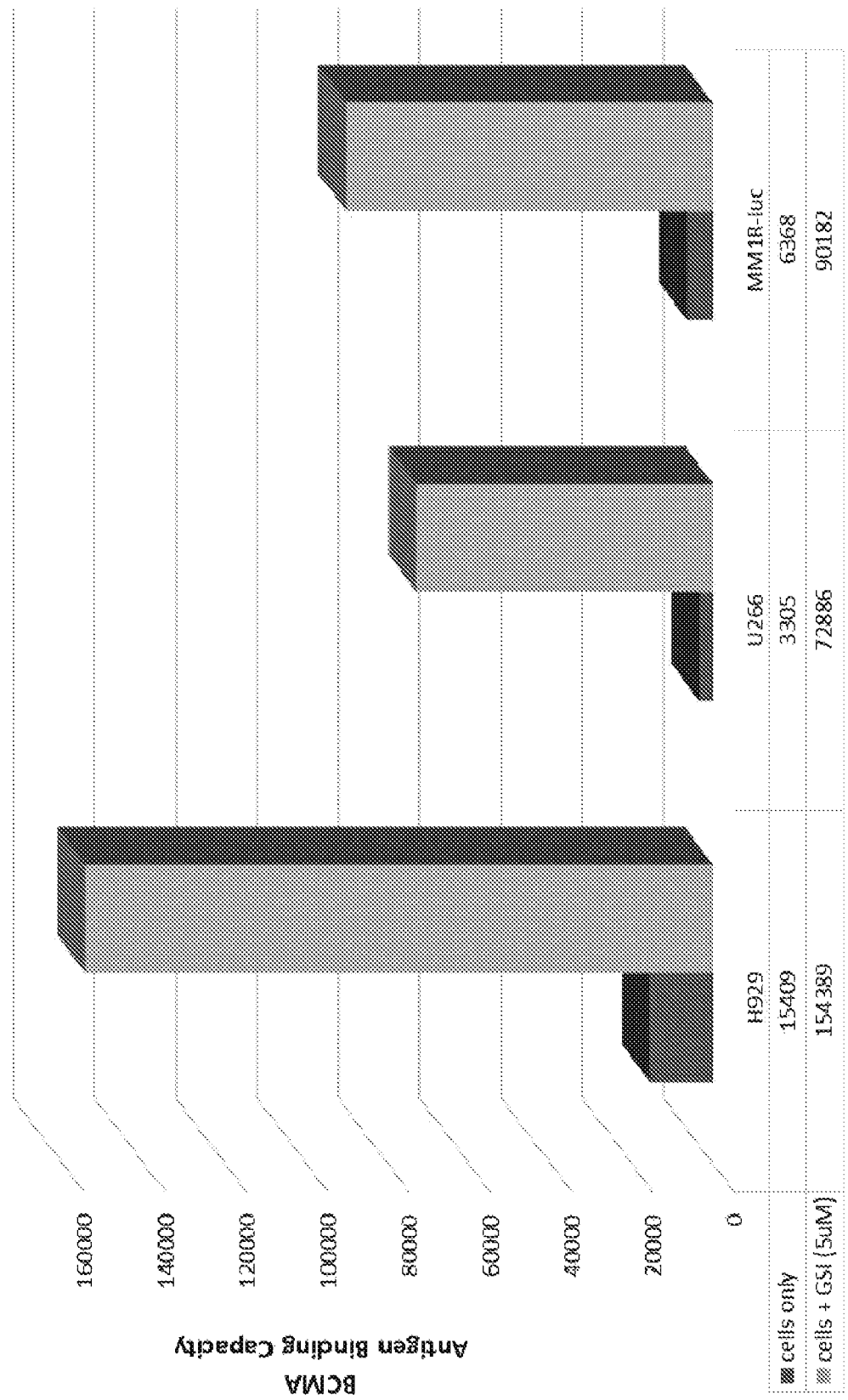

FIG. 13. Antibody Binding Capacity assay (QuantiBrite, Cat. No. 340495, BD Biosciences) was used according to manufacturer instructions to measure the absolute number of BCMA molecules on the self-surface and accessible to antibody binding following 17 hours incubation in the presence or absence of 5 μM gamma secretase inhibitor (R04929097) on three multiple myeloma cells lines. Data demonstrates that GSI upregulates surface BCMA target expression. This data supports BCMA as a viable target for bispecific radioimmunotherapy approaches through binding of BCMA.

Figure 14:
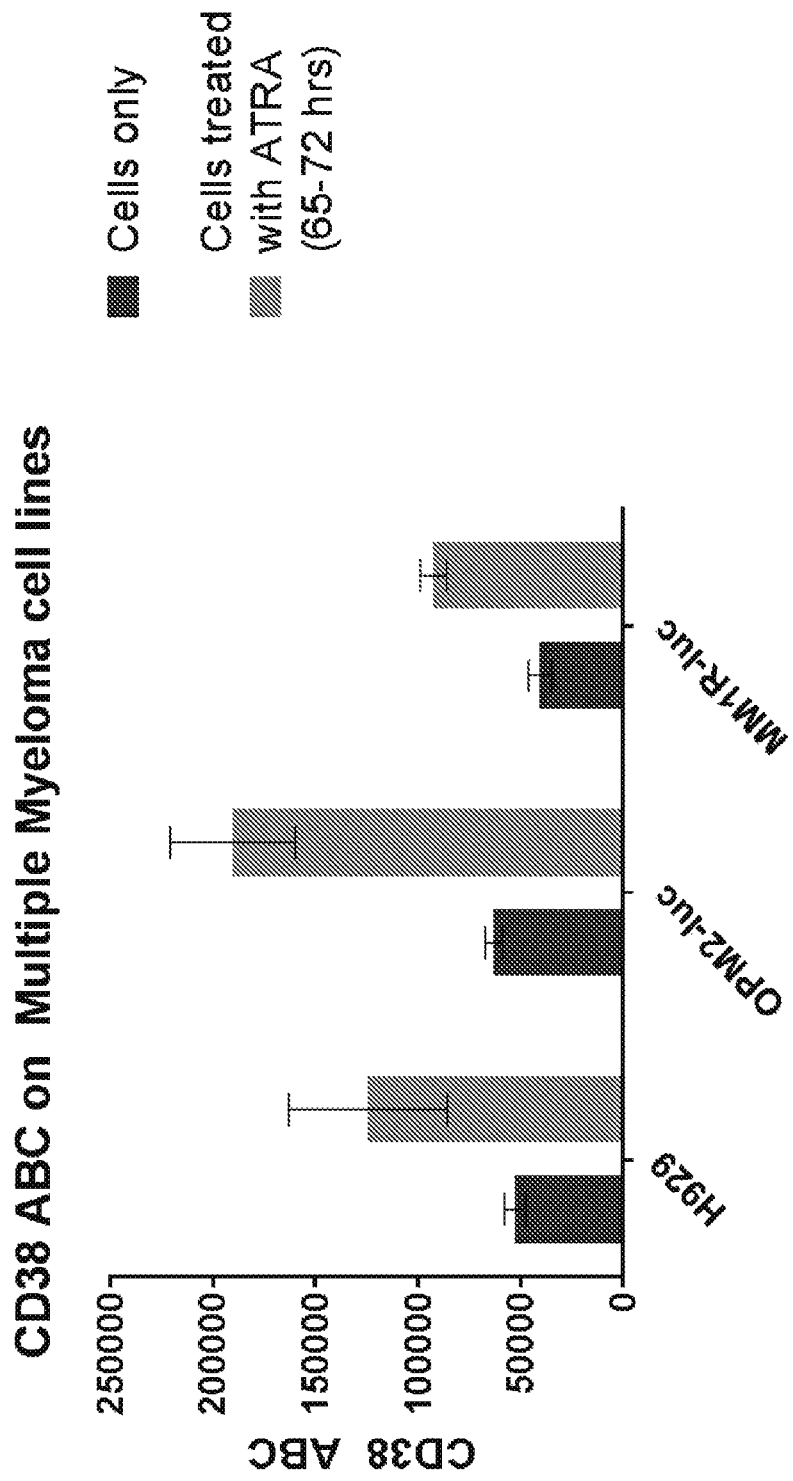

FIG. 14. Antibody Binding Capacity assay (QuantiBrite, BD Biosciences) was used according to manufacturer instructions to measure the absolute number of CD38 molecules on the self-surface and accessible to antibody binding following 65-72 hours treatment of ATRA on three multiple myeloma cells lines. Data demonstrates that ATRA upregulates surface CD38 target expression. This data supports CD38 as a viable target for bispecific radioimmunotherapy approaches through binding of CD38.

Figure 15:
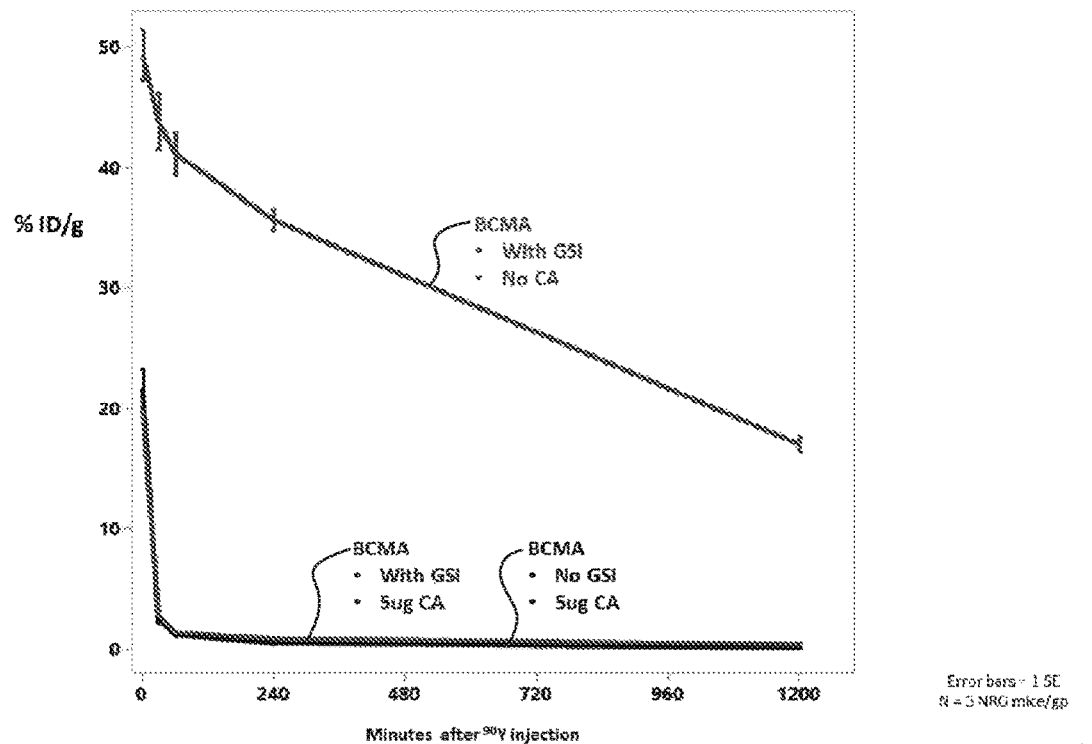

FIG. 15. To ensure our clearing agent was able to effectively clear unbound agent from the blood stream, we conducted a time course experiment to test the impact of the clearing agent on the BCMA bispecific in the presence or absence of GSI. The percent of the injected dose (% ID) was monitored in the blood during a time course experiment by measuring the relative amount of Yttrium$^{90}$ in blood samples obtained from mice.

Figure 16:
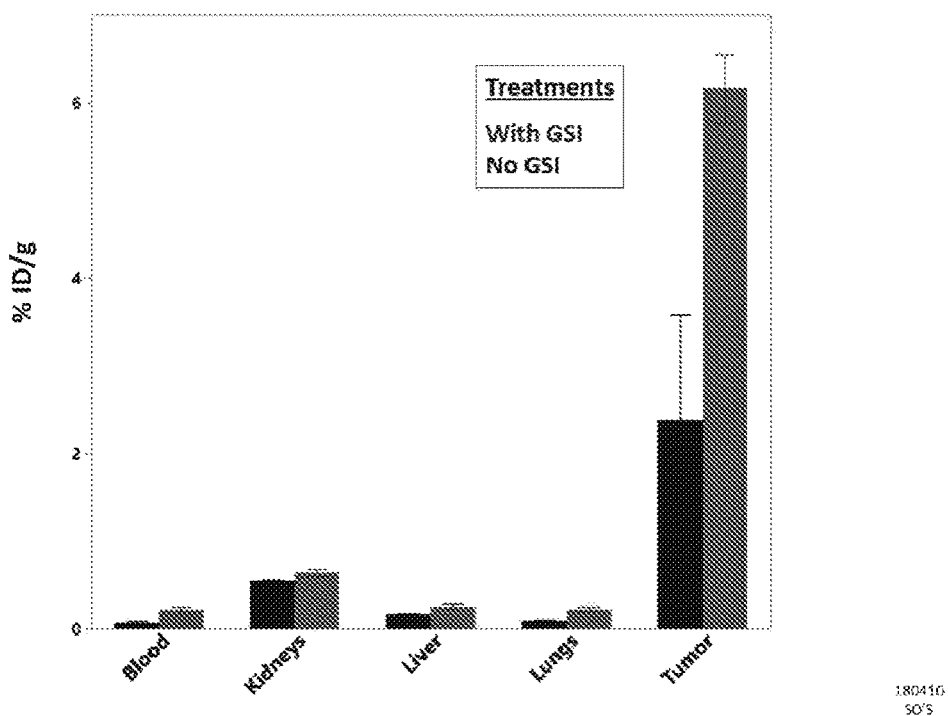

FIG. 16. Biodistribution of $^{90}$Y-DOTA-Biotin using BCMA-Bispecific PRIT. Athymic nude mice (n=5 per group) bearing H929 (MM) xenografts (10$^7$ cells injected in the right flank) were injected at −24 hrs with BCMA bispecific fusion then at −1 hr with CA, and at 0 hrs with $^{90}$Y-DOTA-Biotin, Tumor and normal organ specimens were taken 24 hrs after radioactivity injections. Select tissue biodistributions were obtained 24 hrs after $^{90}$Y-DOTA-Biotin injection.

DETAILED DESCRIPTION

Pretargeted radioimmunotherapy (PRIT) has demonstrated remarkable efficacy targeting tumor antigens, but immunogenicity and endogenous biotin blocking may limit clinical translation. Disclosed herein is a new PRIT approach for the treatment of hematological malignancies such as Multiple Myeloma (MM) and other B cell hyperproliferative disorders.

As described herein, the inventors developed bispecific antibody reagents for PRIT applications that avoids integration of biotin/streptavidin binding and, thus, eliminates endogenous biotin interference and immunogenic elements.

As described in more detail below, as a proof of concept, the inventors developed an anti-CD38 bispecific fusion protein that also specifically binds to radioactive ligands that can be administered separately. In murine xenograft models of MM and non-Hodgkin lymphoma (NHL), the CD38 bispecific construct demonstrated excellent blood clearance and tumor targeting. Dosimetry calculations showed a tumor absorbed dose of 43.8 Gy per mCi injected dose of yttrium-90, with tumor-to-normal organ dose ratios of 7:1 for liver and 15:1 for lung and kidney. In therapy studies, CD38 bispecific PRIT resulted in 100% complete remissions (CR) by day 12 in MM and NHL xenograft models, ultimately curing 80% of mice at optimal doses. In direct comparisons, efficacy of the CD38 bispecific proved equal or superior to streptavidin (SA)-biotin-based CD38-SA PRIT. Each approach cured at least 75% of mice at the highest radiation dose tested (1200 μCi), while at 600 and 1000 μCi doses the bispecific outperformed the SA approach, curing 35% more mice overall ($p<0.004$). The high efficacy of the bispecific PRIT, combined with its' reduced risk of immunogenicity and endogenous biotin interference, make this design of bispecific affinity reagent an attractive candidate for clinical translation. Critically, CD38 PRIT can benefit patients with unresponsive, high-risk disease, because refractory disease typically retains radiation sensitivity.

Based on these positive results, the inventors applied this design to other B cell hyperproliferative associated antigens, such as B cell maturation antigen (BCMA) For example, as described in Example 2, a bispecific molecule that targets BCMA was developed as an alternative target for MM and other cancer cells for PRIT therapy. Experiments demonstrate the BCMA bispecific was able to target tumor cells with minimal off-tissue accumulation and toxicity. The enhancing agent of gamma secretase inhibitor (GSI) in combination with the BCMA bispecific fusion further facilitated blood clearance.

Based off the selective targeting of CD38 bispecific and BCMA bispecific on tumor cells enhancing agents were validated to upregulate surface target expression. In certain embodiments, gamma secretase inhibitors (GSIs) can be used to prevent cleavage of surface bound BCMA and therefore remove cleaved BCMA from the blood stream. In particular embodiments, all-trans-retinoic acid (ATRA) can be used to upregulate CD38, Muc1, and GPRC5D on target cells.

Based on these results, PRIT utilizing the disclosed bispecific antibody compositions will serve as an effective treatment for various hematological disorders, including MM, NHL, and other B cell hyperproliferative diseases, as well as other solid tumor indications as further outlined below. Not to be bound by any particular theory, the PRIT bispecific antibody compositions described herein can be applied to any malignancy or neoplastic diseases in which CD38, BCMA, Muc1, GPRC5D, and/or SlamF7 is/are expressed.

Bispecific Affinity Reagent

In accordance with the foregoing, the disclosure provides a bispecific fusion protein comprising a first binding domain and a second binding domain. The protein is also referred to herein as a reagent or therapeutic agent. The first binding domain specifically binds to a target antigen selected from CD38, B cell maturation antigen (BCMA), Muc1, GPRC5D (G Protein-Coupled Receptor Class C Group 5 Member D), and SlamF7, and the second binding domain specifically binds to a radioactive ligand.

As used herein the term "binding domain" refers to a molecular domain, such as in a peptide, oligopeptide, polypeptide, or protein, that possesses the ability to specifically and non-covalently associate, unite, or combine with a target molecule (e.g., CD38, BCMA, Muc1, GPRC5D, SlamF7, or radioactive moiety). A binding domain includes any naturally occurring, synthetic, semi-synthetic, or recombinantly produced binding partner for the target biological molecule (e.g., CD38, BCMA, Muc1, GPRC5D, SlamF7, or radioactive moiety) or therapeutic compound (e.g., radioactive ligand, such as yttrium-DOTA (Y-DOTA)). In some embodiments, a binding domain is or comprises functional elements of an immunoglobulin or immunoglobulin-like molecule, such as an antibody or T cell receptor (TCR), which includes a functional binding domain or antigen-binding fragment thereof.

As used herein, the term "antibody" encompasses immunoglobulin molecules produced by or derived from any antibody-producing mammal (e.g., mouse, rat, rabbit, and primate including human), and which specifically bind to an antigen of interest. Exemplary antibodies include or are derived from polyclonal, monoclonal and recombinant antibodies.

The antibodies can be human or humanized antibodies; murine antibodies; chimeric, mouse-human, mouse-primate, primate-human monoclonal antibodies; and anti-idiotype antibodies.

In some embodiments, one or both of the first and second binding domains is or comprises a functional antibody, or antigen binding fragment derivative thereof. An antibody fragment is a portion derived from or related to a full-length antibody, including the complementarity-determining regions (CDRs), antigen binding regions, or variable regions thereof. Illustrative examples of antibody fragments useful in the present disclosure include Fab, Fab', F(ab)$_2$, F(ab')$_2$ Fv fragment, VHH fragment, and VNAR fragment. Derivatives indicate that the domain incorporates further modification over mere selection of a portion or fragment of a source antibody. Derivatives can incorporate fusions of disparate parts of a source antibodies (or from multiple source antibodies) to provide a new, single protein domain that functions to bind the antigen of interest. Derivatives can include scFv fragments, single-chain Fab fragment (scFab), diabodies, linear antibodies, single-chain antibody molecules, multispecific antibodies formed from antibody fragments, and the like. A "single-chain Fv" or "scFv" antibody fragment comprises the $V_H$ and $V_L$ domains of an antibody, wherein these domains are present in a single polypeptide chain. The Fv polypeptide can further comprise a polypeptide linker between the $V_H$ and $V_L$ domains, which enables the scFv to form the desired structure for antigen binding.

Antibodies can be further modified to suit various uses. For example, a "chimeric antibody" is a recombinant protein that contains domains from different sources. For example, the variable domains and complementarity-determining regions (CDRs) can be derived from a non-human species (e.g., rodent) antibody, while the remainder of the antibody molecule is derived from a human antibody. A "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions (CDRs) are of non-human origin.

Antibody fragments and derivatives that recognize specific epitopes can be generated by any technique known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain. Further, the antibodies of the present invention can also be generated using various phage display methods known in the art. Finally, the antibodies, or antibody fragments or derivatives, can be produced recombinantly according to known techniques.

In some embodiments, the binding proteins can include single chain antibody variable regions (e.g., domain antibodies, sFv, scFv, Fab), BCMA ligands (e.g., BAFF, APRIL and binding fragments thereof), antigen-binding regions of T cell receptors (TCRs), such as single chain TCRs (scTCRs), or synthetic polypeptides selected for the specific ability to bind to a biological molecule.

As used herein, "specifically binds" refers to an association or union of a binding domain, or a fusion protein containing the binding domain, to a target and bind to molecule with an affinity or $K_a$ (i.e., an equilibrium association constant of a particular binding interaction with units of 1/M) equal to or greater than $10^5$ M$^{-1}$, while not significantly associating or uniting with any other molecules or components in a sample. Binding domains (or fusion proteins thereof) can be classified as "high affinity" binding domains (or fusion proteins thereof) or "low affinity" binding domains (or fusion proteins thereof). "High affinity" binding domains refer to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M-1, or at least $10^{13}$ M$^{-1}$. "Low affinity" binding domains refer to those binding domains with a $K_a$ of up to $10^7$ M$^{-1}$, up to $10^6$ M$^{-1}$, up to $10^5$ M$^{-1}$. Alternatively, affinity can be defined as an equilibrium dissociation constant (Kd) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is higher than the wild type binding domain, or due to a $K_d$ (dissociation constant) for the target antigen that is less 10 than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., *Ann. N.Y. Acad. Sci.* 51:660, 1949; and U.S. Pat. Nos. 5,283,173, 5,468,614, or the equivalent).

In some embodiments, one or both of the first binding domain and a second binding domain comprises a variable light chain domain and variable heavy chain domain, for example of an antibody. The variable light chain domain and variable heavy chain domain can be separated by a "linker domain" . . . . The linker domain can be a five to about 35 amino acid sequence that connects the heavy chain immunoglobulin variable region to the light chain immunoglobulin variable region. In alternative embodiments where the first and/or second binding domain is a T cells receptor, the linker connects T cell receptor V$\alpha$/$\beta$ and C$\alpha$/$\beta$ chains (e.g., V$\alpha$-C$\alpha$, V$\beta$-C$\beta$, V$\alpha$-V$\beta$) or connects each V$\alpha$-C$\alpha$, V$\beta$-C$\beta$, V$\alpha$-V$\beta$ pair to a hinge or hydrophobic domain. The linker domain provides a spacer function and flexibility sufficient for interaction of the two sub-binding domains so that the resulting single chain polypeptide retains a specific binding affinity to the same target molecule as an antibody or T cell receptor. In certain embodiments, a variable region linker comprises from about ten to about 30 amino acids or from about 15 to about 25 amino acids. In particular embodiments, a variable region linker peptide comprises from one to ten repeats of Gly$_x$Ser$_y$, wherein x and y are independently an integer from 1 to 5 (e.g., Gly$_4$Ser, Gly$_3$Ser, Gly$_2$Ser, or (Gly$_3$Ser)$_n$(Gly$_4$Ser)$_1$, (Gly$_3$Ser)$_n$(Gly$_4$Ser)$_n$, or (Gly$_4$Ser)$_n$, wherein n is an integer of 1, 2, 3, 4, or 5) and wherein linked variable regions form a functional binding domain (e.g., scFv, scTCR). In particular embodiments, a linker domain may contain an N-linked glycosylation motif.

Exemplary first and second binding domains and bispecific affinity reagents are now described.

As indicated above, the defined first domains of the bispecific affinity reagents bind to one of CD38, BCMA, Muc1, GPRC5D, or SlamF7, which are antigens associated with the target cells in relevant hematological diseases, including B cell malignancies or hyperproliferative diseases. In some embodiments, the first binding domain comprises an amino acid sequence with at least about 80%, 85%, 90%, 91%, 92%, 93%, 94%, 95%, 96%, 97%, 98%, 99%, or 100% sequence identity to the domains disclosed herein that specifically bind to the target antigens.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, 2$^{nd}$ Edition; Worth Publishers, Inc. NY, NY, pp. 71-77, 1975; and Lewin, Genes IV, Oxford University Press, NY and Cell Press, Cambridge, MA, p. 8, 1990). "Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST 2.0 software as defined by Altschul, et al. (1997) "Gapped BLAST and PSI-BLAST: a new generation of protein database search programs," Nucleic Acids Res. 25:3389-3402, with the parameters set to default values.

CD38 Binding Domains

CD38 is also expressed in a variety of malignant hematological diseases, including multiple myeloma, leukemias and lymphomas, such as B-cell chronic lymphocytic leukemia, T- and B-cell acute lymphocytic leukemia, Waldenstrom macroglobulinemia, primary systemic amyloidosis, mantle-cell lymphoma, pro-lymphocytic/myelocytic leukemia, acute myeloid leukemia, chronic myeloid leukemia, follicular lymphoma, Burkitt's lymphoma, large granular lymphocytic (LGL) leukemia, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression could be involved, include, e.g., broncho-epithelial carcinomas of the lung, breast cancer (evolving from malignant proliferation of epithelial lining in ducts and lobules of the breast), pancreatic tumors, evolving from the 3-cells (insulinomas), tumors evolving from epithelium in the gut (e.g. adenocarcinoma and squamous cell carcinoma), carcinoma in the prostate gland, and seminomas in testis and ovarian cancers. In the central nervous system, neuroblastomas express CD38. The present compositions and methods can encompass any of these disease indications characterized by expression of CD38. See, e.g., U.S. Pat. No. 9,732,154, incorporated herein by reference in its entirety.

In some embodiments, the first binding domain specifically binds to CD38. In some embodiments, the CD38 is a human CD38. (Gene ID: 952).

In certain embodiments, the first binding domain that specifically binds CD38 comprises a $V_L$ region. For example, a $V_L$ region in the first binding domain of the present disclosure is derived from or based on a $V_L$ of a known monoclonal antibody that binds CD38 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds CD38. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds CD38, and provided a binding domain containing the modified $V_L$ region specifically binds its CD38 target with an affinity similar to the wild type binding domain. Similarly, in certain embodiments, the first binding domain that specifically binds CD38 comprises a $V_H$ region. For example, a $V_H$ region in the first binding domain of the present disclosure is derived from or based on a $V_H$ of a known monoclonal antibody that binds CD38 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds CD38. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds CD38, and provided a binding domain containing the modified $V_H$ region specifically binds its CD38 target with an affinity similar to the wild type binding domain.

Exemplary CD38-specific antibodies include daratumumab, isatuximab, TAK-079, TAK-573, GBR-1342, AMG-424, MOR-202, MT-4019, MT-4019ND, MT-4019AS, A-145D, TAK-169, MT-4001V5, MT-4001V6, OSX-1750, Xmab-13243, DOM-1112, MT-4001V3, MT-4007ND.

Exemplary domains that bind to CD38 that can serve as (or part of) the first binding domain have at least 80% sequence identity (e.g., about 80%, 85%, 90%, 91%, 92%, 93%, 94%, 95%, 96%, 97%, 98%, 99%, or 100% sequence identity) to a CD38 binding domain included in an amino acid sequence of a bispecific affinity reagent as set forth in one of SEQ ID NO:2, 4, and 6 (which are encoded by the nucleic acid sequences set forth in SEQ ID NOs:1, 3, and 5, respectively).

In some embodiments, the bispecific affinity reagent comprises an amino acid sequence as set forth in SEQ ID NOs:2, 4, or 6, or comprises an amino acid sequence with at least about 80% identity (e.g., about 80%, 85%, 90%, 91%, 92%, 93%, 94%, 95%, 96%, 97%, 98%, 99%, or 100% sequence identity) to an amino acid sequence of as set forth in one of SEQ ID NO:2, 4, and 6. In some embodiments, the bispecific affinity reagent consists of or consists essentially of an amino acid sequence as set forth in SEQ ID NOs:2, 4, or 6. As used herein with respect to sequence identity, the term "consists essentially of" refers to a near exact identity but allowing for minor variation, such as conservative mutations or addition/deletions that do not otherwise impede or effect the ability of the bispecific molecule to function as described herein.

BCMA Binding Domains

In some embodiments, the first binding domain specifically binds to BCMA. In some embodiments, the BCMA is a human BCMA.

In certain embodiments, the first binding domain that specifically binds BCMA comprises a $V_L$ region. For example, a $V_L$ region in the first binding domain of the present disclosure is derived from or based on a $V_L$ of a known monoclonal antibody that binds BCMA and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds BCMA. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds BCMA, and provided a binding domain containing the modified $V_L$ region specifically binds its BCMA target with an affinity similar to the wild type binding domain. Similarly, in certain embodiments, the first binding domain that specifically binds BCMA comprises a $V_H$ region. For example, a $V_H$ region in the first binding domain of the present disclosure is derived from or based on a $V_H$ of a known monoclonal antibody that binds BCMA and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds BCMA. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds BCMA, and provided a binding domain containing the modified $V_H$ region specifically binds its BCMA target with an affinity similar to the wild type binding domain.

Proteins that specifically bind to BCMA, their active binding sites, and representative polynucleotides encoding the BCMA-specific binding proteins that are encompassed by the present disclosure are described in more detail in WO 2018/151836, which is incorporated herein by reference in its entirety.

Exemplary BCMA-specific antibodies include antibodies J22.0-xi, J22.9-xi, J6M0, J6M1, J6M2, J9M0, J9M1, J9M2, 11D5-3, CA8, A7D12.2, Cl 1 D5.3, C12A3.2, C13F12.1, 13C2, 17A5, 83A10, 13A4, 13D2, 14B1 1, 14E1, 29B1 1, 29F3, 13A7, CA7, SGI, S3071 18G03, S332121F02, S332126E01, S3221 10D07, S336105A07, S3351 15G01, S335122F05, ET140-3, ET140-24, ET140-37, ET140-40, ET140-54, TBL-CLN1, C4.E2.1, Vicky-1, pSCHLI333, pSCHLI372, and pSCHLI373, and antigen-binding portions thereof. Various embodiments of BCMA-specific antibodies and antigen-binding portions thereof, including humanized versions, are disclosed in, for example, PCT Publication Nos. WO 2002/066516, WO 2007/062090, WO 2010/104949, WO 201 1/108008, WO 2012/163805, WO 2014/068079, WO 2015/166073, WO 2014/122143, WO 2014/089335, WO 2016/090327, and WO 2016/079177; Ryan et al., Mol. Cancer. Ther. 6\1):3009, 2007; and Abbas et al., Blood 725:1688, 2016, which BCMA-specific antibodies, antigen-binding portions thereof and humanized versions are all incorporated herein by reference in their entireties. Variable domains and scFv molecules from these BCMA-specific antibodies, or binding domains with at least 90%, at least 91%, at least 92%, at least 93%, at least 94%, at least 95%, at least 96%, at least 97%, at least 98%, at least 99%, at least 99.5%, or 100% identity to the binding domains therein, can be used as the first binding domain the bispecific affinity reagents described herein.

One exemplary scFv that can be incorporated into the first binding domain to specifically bind BCMA is set forth in SEQ ID NO:19. Thus, in some embodiments, the first binding domain is or comprises a sequence with at least about 80%, 85%, 90%, 91%, 92%, 93%, 94%, 95%, 96%, 97%, 98%, 99%, or 100% sequence identity to SEQ ID NO:19.

Additional exemplary domains that bind to BCMA that can serve as (or part of) the first binding domain have at least 80% sequence identity (e.g., about 80%, 85%, 90%, 91%, 92%, 93%, 94%, 95%, 96%, 97%, 98%, 99%, or 100% sequence identity) to a BCMA binding domain included in an amino acid sequence of a bispecific affinity reagent as set forth in one of SEQ ID NO:8 and 10 (which are encoded by the nucleic acid sequences set forth in SEQ ID NOs:7 and 9, respectively).

In some embodiments, the bispecific affinity reagent comprises an amino acid sequence as set forth in SEQ ID NOs:8 or 10, or comprises an amino acid sequence with at least about 80% identity (e.g., about 80%, 85%, 90%, 91%, 92%, 93%, 94%, 95%, 96%, 97%, 98%, 99%, or 100% sequence identity) to an amino acid sequence of as set forth in one of SEQ ID NO:8 and 10. In some embodiments, the bispecific affinity reagent consists of or consists essentially of an amino acid sequence as set forth in one of SEQ ID NOs:8 and 10.

Muc1 Binding Domains

In some embodiments, the first binding domain specifically binds to Muc1. In some embodiments, the Muc1 is a human Muc1 isoform. In some embodiments, the human Muc1 isoform is a tumor associated isoform such as described in Nath, S. and Mukherjee, P., Muc1: a multifaceted oncoprotein with a key role in cancer progression, *Trends Mol Med.* 2014; 20(6):332-342, incorporated herein by reference in its entirety; see also GenBank accession nos. NP_001018016.1, NP_001018017.1, NP_001037855.1, NP_001037856.1, NP_001037857.1, NP_001037858.1, NP_001191214.1, NP_001191215.1, NP_001191216.1, NP_001191217.1, NP_001191218.1, NP_001191219.1, NP_001191220.1, NP_001191221.1, NP_001191222.1, NP_001191223.1, NP_001191224.1, NP_001191225.1, NP_001191226.1, NP 002447.4, each of which is incorporated herein by reference in its entirety. Muc1 is also known in the literature as: ADMCKD, ADMCKD1, CA 15-3, CD227, EMA, H23AG, KL-6, MAM6, MCD, MCKD, MCKD1, MUC-1, MUC-1/SEC, MUC-1/X, MUC1/ZD, PEM, PEMT, and PUM. Mucins are O-glycosylated proteins that play an essential role in forming protective mucous barriers on epithelial surfaces. These proteins also play a role in intracellular signaling. This protein is expressed on the apical surface of epithelial cells that line the mucosal surfaces of many different tissues including lung, breast stomach and pancreas. This protein is proteolytically cleaved into alpha and beta subunits that form a heterodimeric complex. The N-terminal alpha subunit functions in cell-adhesion and the C-terminal beta subunit is involved in cell signaling. Overexpression, aberrant intracellular localization, and changes in glycosylation of this protein have been associated with carcinomas. Muc1 is associated with neoplastic progression and cellular adhesion. In addition to its expression in the hematopoietic lineage, it is also expressed in breast (including luminal, HER2+, and basal), ovarian, prostate, gastric, bile duct, liver, oral squamous cell carcinoma, thyroid, and pancreatic cancers in addition to leukemias, lymphohomas, and MM. See, e.g., Horm, T. M., and Schroeder, J. A., MUC1 and Metastatic Cancer, *Cell Adh Migr.* 2013:7(2):187-198, incorporated herein by reference in its entirety.

In certain embodiments, the first binding domain that specifically binds Muc1 comprises a $V_L$ region. For example, a $V_L$ region in the first binding domain of the present disclosure is derived from or based on a $V_L$ of a known monoclonal antibody that binds Muc1 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds Muc1. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds Muc1, and provided a binding domain containing the modified $V_L$ region specifically binds its Muc1 target with an affinity similar to the wild type binding domain. Similarly, in certain embodiments, the first binding domain that specifically binds Muc1 comprises a $V_H$ region. For example, a $V_H$ region in the first binding domain of the present disclosure is derived from or based on a $V_H$ of a known monoclonal antibody that binds Muc1 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds Muc1. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds Muc1, and provided a binding domain containing the modified $V_H$ region specifically binds its Muc1 target with an affinity similar to the wild type binding domain.

Exemplary Muc1-specific antibodies include antibodies GO-2032c, gatipotuxumab, BrevaRex Mab-AR20.5, Seelomab-GEX, GO-3D1ADC, GO-203/NPs, TAB-004, BLSM-101, SPmAb-2.1, SPmAb-6, GO-3D1ADCC, clivatuzumab tetratextan, and sontuzumab.

Exemplary domains that bind to Muc1 that can serve as (or part of) the first binding domain have at least 80% sequence identity (e.g., about 80%, 85%, 90%, 91%, 92%, 93%, 94%, 95%, 96%, 97%, 98%, 99%, or 100% sequence identity) to a Muc1 binding domain included in an amino acid sequence of a bispecific affinity reagent as set forth in SEQ ID NO:18 (which is encoded by the nucleic acid set forth in SEQ ID NO:17).

Slam7 Binding Domains In some embodiments, the first binding domain specifically binds to Slam7. In some embodiments, the Slam7 is a human Slam7. See, e.g., GenBank accession nos. NP_001269517.1, NP_001269518.1, NP_001269519.1, NP_001269520.1, NP_001269521.1, NP_001269522.1, NP_001269523.1, NP_001269524.1, NP_001269525.1, and NP_067004.3, which are human isoforms of Slamf7 and are encompassed by the present disclosure). SlamF7 is also known as 19A24 protein, CD2 subset, CD2-like receptor activating cytotoxic cells, membrane protein FOAP-12, novel LY9 (lymphocyte antigen 9) like protein, and protein 19A SlamF7 is a signaling lymphocyte activation molecule F7 previously known as cell surface 1 CS1 (CCND3 subset 1, CD2-like receptor-activating cytotoxic cells [CRACC]).

In certain embodiments, the first binding domain that specifically binds Slam7 comprises a $V_L$ region. For example, a $V_L$ region in the first binding domain of the present disclosure is derived from or based on a $V_L$ of a known monoclonal antibody that binds Slam7 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds Slam7. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds Slam7, and provided a binding domain containing the modified $V_L$ region specifically binds its Slam7 target with an affinity similar to the wild type binding domain. Similarly, in certain embodiments, the first binding domain that specifically binds Slam7 comprises a $V_H$ region. For example, a $V_H$ region in the first binding domain of the present disclosure is derived from or based on a $V_H$ of a known monoclonal antibody that binds Slam7 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds Slam7. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds Slam7, and provided a binding domain containing the modified $V_H$ region specifically binds its Slam7 target with an affinity similar to the wild type binding domain.

Exemplary SlamF7-specific antibodies include antibodies elotuzumab, ABP-400, ABBV-838, and PDL-241. Exemplary SlamF7-specific antibodies (and their respective binding domains) are described in more detail in, e.g., Friend, R., et al., Clinical potential of SLAMF7 antibodies-focus on elotuzumab in multiple myeloma, Drug Des Devel Ther. 2017; 11: 893-900; and WO2014055370, each of which is incorporated herein by reference.

Exemplary domains that bind to Slam7 that can serve as (or part of) the first binding domain have at least 80% sequence identity (e.g., about 80%, 85%, 90%, 91%, 92%, 93%, 94%, 95%, 96%, 97%, 98%, 99%, or 100% sequence identity) to a Slam7 binding domain included in an amino acid sequence of a bispecific affinity reagent as set forth in SEQ ID NO:16 (which is encoded by the nucleic acid set forth in SEQ ID NO:15).

In one embodiment, the first domain that binds to SlamF7 comprises a variable heavy chain comprising the sequence set forth herein as SEQ ID NO:54. In one embodiment, the first domain that binds to SlamF7 comprises a variable light chain comprising the sequence set forth herein as SEQ ID NO:55. In a further embodiment, the first domain that binds to SlamF7 comprises the variable heavy domain of SEQ ID NO:54 and the variable light domain of SEQ ID NO:55. These are the heavy and light domains of elotuzumab. In other embodiments, the indicated sequence can incorporate modifications, as described above, so long as the domain retains SlamF7 binding capacity.

GPRC5D binding domains GPRC5D mRNA is predominantly expressed in all malignant plasma cells from MM patients (Atamaniuk J A et al. *Eur J Clin Invest* 42(9) 953-960; 2012; Frigyesi-blood and Cohen, et al. *Hematology* 18(6): 348-35; 2013). GPRC5D expression is variable among the patients and correlate well with plasma cell burden and genetic aberrations such as Rb-1 deletion (Atamaniuk J A et al. Eur J Clin Invest 42(9) 953-960; 2012).

This exclusive expression of GPRC5D on the plasma-cell lineage designates it as an ideal target for therapies targeting multiple myeloma. In some embodiments, the first binding domain specifically binds to GPRC5D. In some embodiments, the GPRC5D is a human GPRC5D (see, e.g., GenBank AB099817.1 and BAC79169.1, incorporated herein by reference).

In certain embodiments, the first binding domain that specifically binds GPRC5D comprises a $V_L$ region. For example, a $V_L$ region in the first binding domain of the present disclosure is derived from or based on a $V_L$ of a known monoclonal antibody that binds GPRC5D and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds GPRC5D. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds GPRC5D, and provided a binding domain containing the modified $V_L$ region specifically binds its GPRC5D target with an affinity similar to the wild type binding domain. Similarly, in certain embodiments, the first binding domain that specifically binds GPRC5D comprises a $V_H$ region. For example, a $V_H$ region in the first binding domain of the present disclosure is derived from or based on a $V_H$ of a known monoclonal antibody that binds GPRC5D and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds GPRC5D. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds GPRC5D, and provided a binding domain containing the modified $V_H$ region specifically binds its GPRC5D target with an affinity similar to the wild type binding domain.

Exemplary GPRC5D antibodies, and thus GPRC5D binding domains, encompassed by the present disclosure include are described in WO 2018/147245, WO 2018/017786A2, and WO 2016/090329, each of which is incorporated herein by reference in its entirety.

Exemplary binding domains that specifically bind GPRC5D comprise a variable heavy ($V_H$) chain region selected from the group consisting of SEQ ID NOs: 59, 60, 61, 62, 63, 64, 65, 66, 67, 68, 69, 70, or 71.

Exemplary binding domains that specifically bind GPRC5D comprise a variable light ($V_L$) chain region selected from the group consisting of SEQ ID NOs: 72, 73, 74, 75, 76, or 77.

In some embodiments, the first binding domain that specifically binds GPRC5D comprises a variable heavy ($V_H$) chain region selected from the group consisting of SEQ ID NOs: 59, 60, 61, 62, 63, 64, 65, 66, 67, 68, 69, 70, or 71 and a variable light ($V_L$) region selected from the group consisting of SEQ ID NOs: 72, 73, 74, 75, 76, or 77. In further embodiments, the first binding domain that specifically binds GPRC5D comprises a variable heavy ($V_H$) chain region selected from the group consisting of SEQ ID NOs: 59, 60, 61, 62, 63, 64, 65, 66, 67, 68, 69, 70, or 71 respectively paired with a variable light ($V_L$) region selected from the group consisting of SEQ ID NOs: 72, 73, 74, 75, 76, or 77.

In further embodiments, the first binding domain that specifically binds GPRC5D comprises a SEQ ID NO: 59, 60, or 64 paired with a $V_L$ chain region comprising SEQ ID NO: 72. In some embodiments, the first binding domain that specifically binds GPRC5D comprises a $V_H$ chain region that comprises SEQ ID NO: 61, 65, 66, 67, or 71 paired with a $V_L$ chain region comprising SEQ ID NO: 73. In some embodiments, the first binding domain that specifically binds GPRC5D comprises a $V_H$ chain region that comprises SEQ ID NO: 62 or 69 paired with a $V_L$ chain region comprising SEQ ID NO: 74. In some embodiments, the first binding domain that specifically binds GPRC5D comprises a $V_H$ chain region that comprises SEQ ID NO: 63 or 68 paired with a $V_L$ chain region comprising SEQ ID NO: 75. In some embodiments, the first binding domain that specifically binds GPRC5D comprises a $V_H$ chain region comprising SEQ ID NO: 70 paired with a $V_L$ chain region comprising SEQ ID NO: 76. In some embodiments, the first binding domain that specifically binds GPRC5D comprises a $V_H$ chain region comprising SEQ ID NO: 71 paired with a $V_L$ chain region comprising SEQ ID NO: 77.

Exemplary binding domains that specifically bind GPRC5D comprise a variable heavy ($V_H$) chain region selected from the group consisting of SEQ ID NOs: 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108.

Exemplary binding domains that specifically bind GPRC5D comprise a variable light ($V_L$) chain region selected from the group consisting of SEQ ID NOs: 109, 110, 111, 112, 113, 22, 115, 30,117, 38, 119, 120, 50, 122, 123, 62,125, 126, 127, 128, 82, 130, 131, 94, 133, 134, 135, 311, 137, 335, 139.

In some embodiments, the first binding domain that specifically bind GPRC5D comprise a variable heavy ($V_H$) chain region selected from the group consisting of SEQ ID NOs: 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108 and further comprises variable light ($V_L$) chain region selected from the group consisting of SEQ ID NOs: 109, 110, 111, 112, 113, 22, 115, 30, 117, 38, 119, 120,50, 122, 123, 62, 125, 126, 127, 128, 82, 130, 131, 94, 133, 134, 135, 311, 137, 335, 139. In some embodiments, the first binding domain that specifically bind GPRC5D comprise a variable heavy ($V_H$) chain region set forth in SEQ ID NOs: 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108 respectively paired with a variable light ($V_L$) chain region set forth in SEQ ID NOs: 109, 110, 111, 112, 113, 22, 115, 30, 117, 38, 119, 120, 50, 122, 123, 62, 125, 126, 127, 128, 82, 130, 131, 94, 133, 134, 135, 311, 137, 335, 139.

Radioactive Ligand Binding Domains

As indicated above, the second binding domain in the bispecific affinity reagent specifically binds to a radioactive ligand. The radioactive ligand can be any ligand, typically a small molecule, which is radioactive and configured for administration into a subject. The radioactive ligand can be or comprise a radioactive ion or radionuclide. In one embodiment, the radioactive ligand is or comprises a radioactive ion or radionuclide complexed with a chelator.

In certain embodiments, the second binding domain that specifically binds to a radioactive ligand comprises a $V_L$ region. For example, a $V_L$ region in the first binding domain of the present disclosure is derived from or based on a $V_L$ of a known monoclonal antibody that binds to a radioactive ligand and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds to a radioactive ligand. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds to a radioactive ligand, and provided a binding domain containing the modified $V_L$ region specifically binds its to a radioactive ligand target with an affinity similar to the reference binding domain. Similarly, in certain embodiments, the first binding domain that specifically binds to a radioactive ligand comprises a $V_H$ region. For example, a $V_H$ region in the first binding domain of the present disclosure is derived from or based on a $V_H$ of a known monoclonal antibody that binds to a radioactive ligand and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds to a radioactive ligand. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds to a radioactive ligand, and provided a binding domain containing the modified $V_H$ region specifically binds its to a radioactive ligand target with an affinity similar to the reference type binding domain.

The radionuclide can be, e.g., a beta emitter, an alpha emitter, or a low-energy electron emitter.

An exemplary chelator encompassed by the disclosure is DOTA, also known as tetraxetan. DOTA includes a central 12-membered tetraaza ring that can hold metal ions and radionuclides. DOTA is a macrocyclic chelating agent that forms stable complexes with metals that are essentially irreversible under physiological conditions. DOTA has a molecular weight of 405 Daltons, diffuses very rapidly, and exhibits rapid renal clearance. DOTA. A variant of DOTA that has a structure that differs to a certain limited extent from the structure of DOTA and that retains the ability to function (e.g., retains sufficient activity to be used for one or more of the purposes described herein) is an active variant of DOTA.

The chelated ion can be radionuclide, which confers radioactivity to the ligand. The radionuclide can be a R emitter, e.g., $^{86}$Y $^{90}$Y, $^{186}$Re, $^{188}$Re, $^{131}$I, $^{177}$Lu, or $^{67}$Cu, an a emitter, e.g., $^{213}$Bi, $^{211}$At, $^{225}$Ac, or a low-energy electron emitter, i.e., an Auger-emitter, e.g., $^{125}$I, $^{111}$In or $^{67}$Ga. In general, useful radionuclides include, for example, but are not limited to, $^{90}$Y, $^{111}$n $^{67}$Ga, $^{68}$Ga $^{177}$Lu, r$^{188}$Re, $^{223}$Ra, $^{57}$Gd, $^{64}$Cu, $^{67}$Cu, $^{89}$Zr, $^{47}$sc, $^{153}$sm, $^{166}$Tb, $^{166}$Tb, $^{166}$Ho, $^{212}$Pb, $^{212}$Bi, $^{213}$Bi, $^{225}$Ac, $^{227}$Th, $^{211}$At and $^{227}$Ac. In one embodiment, the radionuclide is Yttrium ($^{90}$Y). Thus, in some embodiments, the radioactive ligand is or comprises $^{90}$Y-DOTA.

U.S. Pat. No. 8,648,176, incorporated herein by reference in its entirety, describes in more detail exemplary second binding domains that specifically binds to a metal chelate, such as DOTA. The second binding domain, e.g., an scFv domain, that binds a metal chelate with a radionuclide, can have a sequence at least or about 70% (e.g., at least or about 75%, 80%, 85%, 90%, 95% or 98%) identical to SEQ ID NO:20, exclusive of the linker at residues 120-134. Residues 1-119 of SEQ ID NO:20 represent the variable heavy chain of the antibody designated 2D 12.5 (Corneillie et al., J. Am. Chem. Soc. 125:15039-15048, 2003); residues 120-134 represent a linker; and residues 135-244 represent the variable light chain of 2D 12.5. These embodiments of the second domain can include a mutation at a position corresponding to one or more of the following positions within SEQ ID NO:20: 29, 30, 31, 32, 33, 34, 36, 37, 47, 48, 49, 51, 54, 55, 56, 57, 58, 60, 69, 71, 73, 94, 95, 96, 97, 102, 103, 105, 106, 107, 164, 165, 166, 167, 169, 171, 172, 184, 185, 188, 189, 223, 224, 225, 226, 228, 229, 230, 231, 233, and 234. Alternatively, or in addition, the second binding domain can include a mutation at a position corresponding to one or more of the following positions within SEQ ID NO:20: 60, 61, 63, 71, 80, 88, 108, 139, 157, 165, 187, 230, and 234. Alternatively, or in addition, the second binding domain can include a mutation at a position corresponding to one or more of the following positions within SEQ ID NO:20: 100, 187, and 227. More specifically, the present second binding domain can include the sequence of residues 1-244 of mutant C8.2-1 (SEQ ID NO:21); C8.2-2 (SEQ ID NO:22); C8.2-3 (SEQ ID NO:23); C8.2-4 (SEQ ID NO:24); C8.2-5 (SEQ ID NO:25); C8.2-6 (SEQ ID NO:26); C7.3 1 (SEQ ID NO:27); C7.3 2 (SEQ ID NO:28); C7.3 3 (SEQ ID NO:29); C7.3 4 (SEQ ID NO:30); C7.3 5 (SEQ ID NO:31); C7.3 6 (SEQ ID NO:32); C7.3 7 (SEQ ID NO:33); C7.3 8 (SEQ ID NO:34); C7.3 9 (SEQ ID NO:35); or C7.3 10 (SEQ ID NO:36).

In some embodiments, the bispecific affinity reagent is a fusion protein comprising both the first binding domain and the second binding domain separated by a hinge region. As used herein, a "hinge region" or a "hinge" refers to a region that provides sufficient space and flexibility between the first and second binding domains to facilitate the binding of each binding domain to its respective specific antigen without mutual interference. Exemplary hinge domains that are encompassed by this disclosure, and detailed discussions thereof, are provided in WO 2018/151836, which is incorporated herein by reference in its entirety. In some embodiments, the hinge region can comprise (a) an immunoglobulin hinge sequence (made up of, for example, upper and core regions) or a functional fragment or variant thereof, (b) a type II C-lectin interdomain (stalk) region or a functional fragment or variant thereof, or (c) a cluster of differentiation (CD) molecule stalk region or a functional variant thereof. In some embodiments, the immunoglobulin hinge region can be a naturally occurring upper and middle hinge amino acid sequences interposed between and connecting the $CH_1$ and $CH_2$ domains (for IgG, IgA, and IgD) or interposed between and connecting the $CH_1$ and $CH_3$ domains (for IgE and IgM) found in the heavy chain of an antibody. In certain embodiments, the hinge region is human, and in particular embodiments, comprises a human IgG hinge region. In some embodiments, the IgG hinge region comprises a human IgG1 Fc hinge. In some embodiments, the IgG hinge region comprises a human IgG2 Fc hinge. In some embodiments, the IgG hinge region comprises a human IgG3 Fc hinge. In some embodiments, the IgG hinge region comprises a human IgG4 Fc hinge.

Methods of Treatment

The bispecific affinity reagents (e.g., fusion proteins with first and second binding domains) described herein are useful to pretarget cells for radiotimmunoherapy. Accordingly, in another aspect, the disclosure provides a method of treating a hematological or other applicable malignancy. The method comprises administering to the subject a therapeutically effective amount of the bispecific affinity reagent as described herein, and administering a therapeutically effective amount of a radioactive ligand.

The hematological malignancy can include any hematological hyperproliferative disorder, including hematological cancer. In some embodiments, the hematological disorder is a B cell hyperproliferative disorder or malignancy. The term B cell malignancy can include multiple myeloma (MM), a leukemia or lymphoma.

Leukemias encompassed by this disclosure include acute lymphoblastic leukemia (ALL), acute myeloid leukemia (AML), chronic lymphocytic leukemia (CLL) and chronic myeloid leukemia (CML). Subtypes of ALL include precursor B acute lymphoblastic leukemia, precursor T acute lymphoblastic leukemia, Burkitt's leukemia, and acute biphenotypic leukemia. Subtypes of CLL include B-cell prolymphocytic leukemia, which is a more aggressive disease. Subtypes of AML include acute promyelocytic leukemia, acute myeloblastic leukemia, and acute megakaryoblastic leukemia. Subtypes of CML include chronic myelomonocytic leukemia. Other types of leukemias include Hairy cell leukemia (HCL), T-cell prolymphocytic leukemia (T-PLL), large granular lymphocytic leukemia. Any of these types of leukemias are encompassed by the present disclosure to the extent that the associated transformed cells express CD38, BCMA, Muc1, GPRC5D, and/or SlamF7.

Lymphomas are any neoplasms of the lymphatic tissues. Lymphomas encompassed by this disclosure include the Hodgkin's lymphomas (HL) and the non-Hodgkin lymphomas (NHL). Subtypes of lymphomas include B cell small cell lymphoma, splenic marginal zone lymphoma, extranodal marginal zone B cell lymphoma, also called MALT lymphoma, nodal marginal zone B cell lymphoma, extranodal marginal zone B cell lymphoma, also called MALT lymphoma, follicular lymphoma, primary cutaneous follicle center lymphoma, mantle cell lymphoma, diffuse large B cell lymphoma, Epstein-Barr virus-positive DLBCL of the elderly, lymphomatoid granulomatosis, primary mediastinal (thymic) large B-cell lymphoma, intravascular large B-cell lymphoma, ALK+ large B-cell lymphoma, plasmablastic lymphoma, primary effusion lymphoma, large B-cell lymphoma arising in HHV8-associated multicentric Castleman's disease, and Burkitt lymphoma. Any of these types of lymphoma are encompassed by the present disclosure to the extent that the associated transformed cells express CD38, BCMA, Muc1, GPRC5D, and/or SlamF7.

In addition to hematolocally relevant malignancies, a person of ordinary skill in the art would understand that, while this disclosure is generally framed in the context of hematological malignancies, the disclosed compositions and methods can also be applied to other tumor and cancers, such as breast (including luminal, HER2+, and basal), ovarian, prostate, gastric, bile duct, liver, oral squamous cell carcinoma, thyroid, and pancreatic cancers. Such applications are also encompassed by the present disclosure.

The hematological malignancy and/or hyperproliferative disorder, or other relevant tumors and cancers contemplated in this aspect can be characterized by the expression of, or in some embodiments an increased expression of, at least one of CD38, BCMA, Muc1, GPRC5D, and SlamF7 in the malignant cell of the subject. The status of these other hematological malignancies and/or hyperproliferative disorders, or other relevant tumors or cancers with respect to expression of CD38, BCMA, Muc1, GPRC5D, and/or SlamF7 can be readily determined by persons of ordinary skill in the art using, e.g., immunoassays that incorporate affinity reagents with domains such as the first domains described herein.

As used herein, the term "treat" refers to medical management of a disease, disorder, or condition of a subject (e.g., a human or non-human mammal, such as a primate, horse, dog, mouse, rat, and the like). For example, an appropriate dose or treatment regimen comprising bispecific fusion protein that bind CD38, BCMA, Muc1, GPRC5D, or SlamF7 in combination administration of a corresponding radioactive moiety (e.g., in PRIT) is administered to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof. For example, the replication rate of a proportion of targeted CD38, BCMA, Muc1, GPRC5D, and/ or SlamF7 expressing cells is slowed or stopped. In other outcomes, a proportion of CD38, BCMA, Muc1, GPRC5D, and/or SlamF7 expressing cells is killed.

The bispecific affinity reagent in this aspect can encompass any bispecific affinity reagent described herein comprising a first binding domain that specifically binds to one of CD38, BCMA, Muc1, GPRC5D, and SlamF7, and a second binding domain that specifically binds a radioactive ligand.

Effective doses of the bispecific affinity reagent can be readily determined by persons of ordinary skill in the art. As described below, murine xenograft experiments utilized single injections of 2.8 nmol (210 to 420 µg) bispecific reagent for successful effect on the grafted tumors. Preferred embodiments for dosing are equivalent dosing regiments that can be readily established for human subjects adjusting for body mass. For example, doses can range from 0.05 mg/kg to 100 mg/kg, 0.1 mg/kg to 75 mg/kg, 0.1 mg/kg to 50 mg/kg, 0.1 mg/kg to 25 mg/kg, 1 mg/kg to 30 mg/kg, 2 mg/kg to 25 mg/kg, 5 mg/kg to 25 mg/kg, 10 mg/kg to 20 mg/kg, or 15 mg/kg to 20 mg/kg. Exemplary doses include 0.05 mg/kg, 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 35 mg/kg, 40 mg/kg, 50 mg/kg, 60 mg/kg, 70 mg/kg, 80 mg/kg, 90 mg/kg, and 100 mg/kg.

The radioactive ligand of this aspect is described above. In an illustrative, non-limiting embodiment, the radioactive ligand comprises yttrium-DOTA. The radioactive ligand is administered to the subject after the bispecific affinity reagent is administered. In some embodiments, the radioactive ligand is administered to the subject about 1, 2, 3, 4, 5, 6, 7, 8, 9, 10, 15, 24, 10, 35, or 40 hours after the administration of the bispecific affinity reagent. In some embodiments, the radioactive ligand is administered to the subject about 10-to about 30, about 15 to about 25 hours, or about 20 to about 25 hours after the administration of the bispecific affinity reagent.

Effective doses of the radioactive ligand can be readily determined by persons of ordinary skill in the art to provide for sufficient ligand to specifically bind cell the present cell-bound bispecific affinity reagent in the subject. As described below, murine xenograft experiments utilized single injections of about 1.2 nM (2 µg) DOTA-biotin labeled with 20 to 40 µCi (0.74-1.48 MBq) of $^{90}$Y for successful effect on the grafted tumors. Equivalent dosing regimens can be readily established for human subjects adjusting for body mass.

In some embodiments, the method further comprises administering an effective amount of a clearing agent (CA). The CA accelerates the clearance of any unbound antibody from the subject's bloodstream to reduce the likelihood that the radioactive moiety will bind to bispecific fusion protein that is not bound to CD38, BCMA, Muc1, GPRC5D, or SlamF7. Accordingly, the CA is typically administered after administering the bispecific fusion protein but before administering the radioactive moiety. In some embodiments, the CA is administered 8 hours, 7 hours, 6 hours, about 5 hours, 4 hours, 3 hours, 2 hours, 1 hour, or just prior to administration of the radioactive ligand. In some embodiments, the CA is administered between about 0.5 and 4 hours or about 1-2 hours before administration of the radioactive ligand.

Any clearing agent effective to facilitate removal of unbound bispecific affinity reagent from circulation is encompassed by the disclosure. An exemplary CA is a DOTAY-Dextran clearing agent (Orcutt KD, et al., *Molecular cancer therapeutics*. 2012; 11(6):1365-1372), incorporated herein by reference in its entirety.

Effective doses of the CA can be readily determined by persons of ordinary skill in the art to provide for at least some clearance of unbound bispecific affinity reagent. As described below, murine xenograft models utilized approximately 0.5 to 10 µg per individual mouse. Equivalent dosing regiments can be readily established for human subjects adjusting for body mass.

In some embodiments, the method further comprises administering an agent that enhances expression of the target antigen, referred to herein as an "enhancing agent."

An exemplary enhancing agent encompassed by the disclosure is all-trans retinoic acid (ATRA), which is a physiologic derivative of vitamin A (retinol) and can be represented by formula I. ATRA has been shown to increase CD38 expression levels in cells, such as target MM cells. See, e.g., Nijhof, I. S., et al., Upregulation of CD38 expression on multiple myeloma cells by all-trans retinoic acid improves the efficacy of daratumumab, Leukemia, 2015; 29(10):2039-49, incorporated herein by reference in its entirety. Considering that CD38 exhibits high surface density and uniform expression on MM and NHL cells, and relatively low expression on normal myeloid and lymphoid cells, expression enhancement induced by ATRA administration can serve to further distinguish the transformed cells from healthy cells. Furthermore, ATRA has been shown to increase GPRC5D expression levels in cells. See, e.g., Inoue, S., et al., The RAIG Family Member, GPRC5D, Is Associated with Hard-Keratinized Structures, *Journal of Investigative Dermatology*, 2004; 122(3):565-573, incorporated herein by reference in its entirety. Thus, like CD38, expression enhancement of GPRC5D induced by ATRA administration can serve to further distinguish the transformed cells from healthy cells and provide for enhanced targeting of diseased cells.

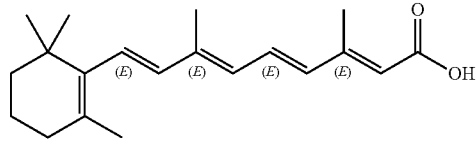

I

Functional derivatives or analogs of ATRA have also been identified to enhance CD38 or GPRC5D expression in diseased cells, such as MM cells, and can be used to similar effect as ATRA. Such derivatives or analogs are also encompassed by the present disclosure. For example, one analog is fenretinide (chemical name: (2E,4E,6E,8E)-N-(4-hydroxyphenyl)-3,7-dimethyl-9-(2,6,6-trimethylcyclohexen-1-yl)nona-2,4,6,8-tetraenamide), which is a semi-synthetic retinoid derivative and can be represented by formula I:

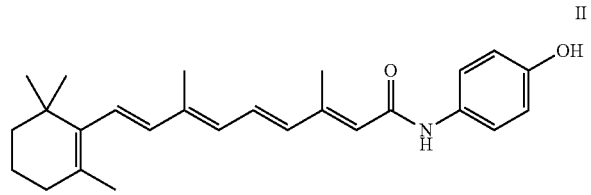 [SMILES: CC1=C(/C=C/C(C)=C/C=C/C(C)=C/C(=O)Nc2ccc(O)cc2)C(C)(C)CCC1]

II

Use of these ATRA enhancers and functional analogs or derivatives thereof can contribute to enhanced therapeutic attack of transformed CD38 or GPRC5D positive cells, including MM and NHL cells from the subject using the bispecific affinity reagent PRIT approach described herein that incorporates a first binding domain that specifically binds to CD38 or GPRC5D.

ATRA and its derivatives and analogs can be administered concurrently with prior to the bispecific affinity reagent comprising a first binding domain that specifically binds CD38 or GPRC5D. In some embodiments, the ATRA (or derivative or analog thereof) enhancing agent is administered prior to the administration of the bispecific affinity reagent comprising a first binding domain that specifically binds CD38 or GPRC5D. For example, the ATRA (or derivative or analog thereof) enhancing agent can be administered between about 1 hour to about 3 days prior to the administration of the bispecific affinity reagent comprising a first binding domain that specifically binds CD38 or GPRC5D, such as about 2, 5, 10, 15, 20, 24 hours before the administration of the bispecific affinity reagent comprising a first binding domain that specifically binds CD38 or GPRC5D. In other embodiments, the ATRA (or derivative or analog thereof) enhancing agent is administered about 0.75, 1, 1.25, 1.5, 1.75, 2, 2.25, 2.5, 2.75, 3, or 3.5 days prior to the administration of the bispecific affinity reagent comprising a first binding domain that specifically binds CD38 or GPRC5D.

The ATRA (or derivative or analog thereof) can be formulated for any form of administration, such as systemic (e.g., I.V., parenteral) or oral administration (e.g., in a solid matrix or liquid solution suitable for ingestion). In some embodiments, the ATRA (or derivative or analog thereof) is formulated in liposomal form, which has provided advantages for delivery, bioavailability, and reducing toxicity. See, e.g., WO2001074384A1, Grace, V. M., et al, Liposome encapsulated all trans retinoic acid (ATRA) has enhanced immunomodulatory and inflammation reducing activities in mice model, *Anticancer Agents Med Chem.* 2015; 15(2): 196-205; Ozpolat, B. and Lopez-Berestein, G., Liposomal-all-trans-retinoic acid in treatment of acute promyelocytic leukemia, *Leuk Lymphoma.* 2002 May; 43(5):933-41; and Ozpolat, B. and Lopez-Berestein, G., Pharmacokinetics of intravenously administered liposomal all-trans-retinoic acid (ATRA) and orally administered ATRA in healthy volunteers, *J Pharm Pharmaceut Sci,* 6(2):292-301, 2003, each of which is incorporated herein by reference in its entirety.

The ATRA (or derivative or analog thereof) can be administered at any dose effective to induce upregulation of CD38 or GPRC5D in target cells (e.g., MM cells). Exemplary, non-limiting doses are between 1 mg/m$^2$ to about 400 mg/m$^2$, such as about 1 mg/m$^2$, about 5 mg/m$^2$, about 10 mg/m$^2$, about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 55 mg/m$^2$, about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 225 mg/m$^2$, about 250 mg/m$^2$, about 275 mg/m$^2$, about 300 mg/m$^2$, about 350 mg/m$^2$, or about 400 mg/m$^2$.

Another exemplary enhancing agent encompassed by the disclosure is a γ-secretase inhibitor (GSI). Administration of GSIs is associated with enhanced expression of surface BCMA and Muc1 antigens on hematological cells, such as MM cells. By preventing the cleavage of BCMA and Muc1 from the cell surface, less soluble antigen is present to serve as a decoy for the bispecific agent. GSIs are described in more detail in WO 2018/151836, which is incorporated herein by reference in its entirety. Exemplary γ-secretase inhibitors (GSIs) include small molecules, peptidomimetic compounds or γ-secretase-specific binding proteins. A GSI can target any one or more of the γ-secretase complex proteins, including presenilin 1 (PS1), presenilin 2 (PS2), nicastrin (NCT), anterior pharynx-defective 1 (APH-1), and presenilin enhancer 2 (PEN-2), provided that the γ-secretase cleavage activity is reduced compared to uninhibited γ-secretase. In certain embodiments, the γ-secretase activity is reduced at least about 50%, at least about 60%, at least about 70%, at least about 75%, at least about 80%, at least about 85%, at least about 90%, at least about 95%, or 100%. Assays for measuring γ-secretase activity are known in the art (see, e.g., Laurent et al., 2015). For example, the level of soluble BCMA can be a surrogate measure for γ-secretase activity. Representative small molecule GSIs, for use with a BCMA-targeted immunotherapy to treat a proliferative or autoimmune disease or disorder, include avagacestat, DAPT, BMS-906024, BMS-986115, LY411575, LY3039478, MK-0752, PF-03084014, RO4929097, semagacestat, YO-01027, and any combination thereof. Other GSIs are γ-secretase-specific binding proteins, such as antibodies or antigen binding portions thereof that a γ-secretase complex or a γ-secretase complex protein, such as presenilin 1 (PS1), presenilin 2 (PS2), nicastrin (NCT), anterior pharynx-defective 1 (APH-1), and presenilin enhancer 2 (PEN-2). An exemplary γ-secretase-specific binding protein is a nicastrin-specific binding protein, such as antibodies scFvG9, A5226A, 2H6, 10C11, and antigen binding fragments thereof. This can contribute to enhanced therapeutic attack of transformed BCMA positive and/or Muc1 positive cells, including MM cells from the subject using the bispecific affinity reagent PRIT approach described herein that incorporates a first binding domain that specifically binds to BCMA and/or Muc1.

GSI can be administered concurrently with or prior to the bispecific affinity reagent. In some embodiments, the bispecific affinity reagent comprises a first binding domain that specifically binds BCMA. In other embodiments, the bispecific affinity reagent comprises a first binding domain that specifically binds Muc1. In some embodiments, the GSI enhancing agent is administered prior to the administration of the bispecific affinity reagent comprising a first binding domain that specifically binds BCMA or Muc1. For example, the GSI enhancing agent can be administered between about 1 hour to about 3 days prior to the administration of the bispecific affinity reagent comprising a first binding domain that specifically binds BCMA or Muc1, such as about 2, 5, 10, 15, 20, 24 hours before the administration of the bispecific affinity reagent comprising a first binding domain that specifically binds BCMA or Muc1. In other embodiments, the GSI enhancing agent is administered about 0.75, 1, 1.25, 1.5, 1.75, 2, 2.25, 2.5, 2.75, 3, or 3.5 days prior to the administration of the bispecific affinity reagent comprising a first binding domain that specifically binds BCMA or Muc1.

GSI can be formulated for any appropriate routes of administration. In some embodiments, the GSI is administered orally, intravenously, parentally, and the like.

The GSI can be administered at any dose effective to induce upregulation of BCMA or Muc1 in target cells (e.g., MM cells). Exemplary, non-limiting doses include about 1 mg/kg to about 200 mg/kg, for example about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 125 mg/kg, about 150 mg/kg, about 175 mg/kg, or about 200 mg/kg.

In another embodiment, the enhancing agent can be a corticosteroid, such as dextramethasone.

To illustrate the general sequence of administration steps for certain embodiments, non-limiting embodiments for administration in the disclosed method include administering an enhancing agent, followed within about 24 hours (e.g., 6 to 30 hours) with administration of the bispecific affinity reagent, followed within about 24 hours (e.g., 6 to 48 hours) of administration of the CA, followed within about 2 hours (e.g., 30 minutes to about 3 hours) of the administration of the radioactive ligand.

Combination Therapies

The disclosure also encompasses methods that incorporate administration of two or more bispecific affinity reagents to target the hematological malignant or hyperproliferative cells in a subject for treatment by specifically targeting multiple cellular antigens.

The therapeutic strategies and affinity reagents described above can be combined together (or with a bispecific affinity reagent that can specifically bind CD20) to utilize (e.g., administer) two or more of the described bispecific affinity reagents in combination with separate administration of at least one radioactive ligand. The combination strategies can optionally include administering at least one clearing agent prior to administering the at least one radioactive ligand, as described in more detail above. The combination strategies can also optionally include administering at least one enhancing agent to increase the expression of the target antigen in the malignant or hyperproliferative cells, as described in more detail above.

Accordingly, the disclosure provides a method of treating a hematological malignancy in a subject. The method comprises administering to the subject a therapeutically effective amount of a first bispecific affinity reagent and a therapeutically effective amount of a second bispecific affinity reagent. Thereafter, the method further comprises administering to the subject a therapeutically effective amount of a radioactive ligand. The first bispecific affinity reagent and the second bispecific affinity reagent each comprises a first binding domain that specifically binds to an antigen and a second binding domain that specifically binds to the radioactive ligand. The antigen can be associated with a cancer or hyperproliferative disorder, such as a hematological malignancy or hyperproliferative disease as described herein. The first binding domain of the first bispecific affinity reagent and the first binding domain of the second bispecific affinity reagent specifically bind to different antigens selected from CD38, BCMA, Muc1, GPRC5D, SlamF7, and CD20, as described herein.

CD20 is a B cell specific surface antigen found on several transformed hematological cells, such as in non-Hodgkin lymphoma cells, and can serve as an additional target in combination therapies addressing hematological malignancies as described herein. CD20 is also known as B1; MS4A1; S7; Bp35; CVID5; MS4A2; and LEU-16. CD20 remains an appealing antigen, however, due to its extensive clinical record as a successful immunotherapy target, as demonstrated in trials using rituximab, a monoclonal antibody targeting CD20 (Coiffier et al., N Engl J Med 2002; 346(4):235-42; Lenz et al., J Clin Oncol 2005; 23(9):1984-92; Marcus R, et al., J Clin Oncol 2008; 26(28):4579-86; Pfreundschuh et al., Lancet Oncol 2011; 12(11):1013-22).

The anti-CD20 bispecific affinity reagent of this aspect has the same structural design as the other bispecific affinity reagents, as described in more detail above. Briefly, the first binding domain can comprise any antibody or a fragment or derivative thereof that binds CD20. The anti-CD20 bispecific affinity reagent also comprises a second binding domain that specifically binds a radioactive ligand, as described in more detail above. Finally, the first and the second binding domains can be linked by a hinge region, as described above.

In some embodiments, the CD20 is a human CD20, such as represented by GenBank Gene ID: 931).

In certain embodiments, the first binding domain that specifically binds CD20 comprises a $V_L$ region. For example, a $V_L$ region in the first binding domain of the present disclosure is derived from or based on a $V_L$ of a known monoclonal antibody that binds CD20 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds CD20. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds CD20, and provided a binding domain containing the modified $V_L$ region specifically binds its CD20 target with an affinity similar to the wild type binding domain. Similarly, in certain embodiments, the first binding domain that specifically binds CD20 comprises a $V_H$ region. For example, a $V_H$ region in the first binding domain of the present disclosure is derived from or based on a $V_H$ of a known monoclonal antibody that binds CD20 and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds CD20. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds CD20, and provided a binding domain containing the modified $V_H$ region specifically binds its CD20 target with an affinity similar to the wild type binding domain.

Anti-CD20 antibodies, or functional fragments or derivatives thereof can serve as the first binding domain. Exemplary anti-CD20 antibodies suitable for use in the therapeutic methods described herein include 2H7, 1.5.3, 1F5, Leu16, rituximab, ofatumumab, veltuzumab, and ocrelizumab.

In certain embodiments, a binding domain comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region ($V_L$); e.g., to a $V_L$ from 1.5.3 (SEQ ID NO.:39), 1F5 (SEQ ID NO.:41), Leu16 (SEQ ID NO.:40), rituximab, ofatumumab, veltuzumab, or ocrelizumab.

In further embodiments, a binding domain comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a heavy chain variable region ($V_H$); e.g., to a $V_H$ from 1.5.3 (SEQ ID NO.:42), 1F5 (SEQ ID NO.:44), Leu16 (SEQ ID NO.:43), rituximab, ofatumumab, veltuzumab, or ocrelizumab.

In still further embodiments, a binding domain comprises (a) an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a $V_L$; e.g., to a $V_L$ from 1.5.3 (SEQ ID NO.:39), 1F5 (SEQ ID NO.:42), Leu16 (SEQ ID NO.:40), rituximab, ofatumumab, veltuzumab, or ocrelizumab; and (b) an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a $V_H$; e.g., to a $V_H$ from 1.5.3 (SEQ ID NO.:42), 1F5 (SEQ ID NO.:44), Leu16 (SEQ ID NO.: 43), rituximab, ofatumumab, veltuzumab, or ocrelizumab. In any of the aforementioned embodiments, each CDR of the $V_L$, $V_H$, or both comprises zero changes or at most one, two, three, four, five or six changes, as compared to a parent monoclonal antibody or fragment or derivative thereof that specifically binds to CD20, provided that a binding domain containing the modified $V_L$, $V_H$, or both region specifically binds CD20 with an affinity similar to the wild type binding domain.

In certain embodiments, a binding domain comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a scFv, e.g., a scFv from an antibody of 1.5.3 (SEQ ID NO.:56), 1F5 (SEQ ID NO.:58), Leu16 (SEQ ID NO.:57), rituximab, ofatumumab, veltuzumab, or ocrelizumab, wherein each CDR of the scFv comprises zero changes or at most one, two, three, four, five or six changes, as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody.

In certain embodiments, a binding domain is encoded by a polynucleotide that is at least 60%, at least 70%, at least 75%, at least 80%, at least 85%, at least 90%, at least 95%, or 100% identical to a polynucleotide sequence encoding a light chain variable region ($V_L$); e.g., to a $V_L$-encoding polynucleotide from 1.5.3 (SEQ ID NO.:48), 1F5 (SEQ ID NO.:50), Leu16 (SEQ ID NO.:49), rituximab, ofatumumab, veltuzumab, or ocrelizumab.

In further embodiments, a binding domain comprises a polynucleotide that is at least 60%, at least 70%, at least 75%, at least 80%, at least 85%, at least 90%, at least 95%, or 100% identical to a polynucleotide sequence encoding a heavy chain variable region ($V_H$); e.g., to a $V_H$-encoding polynucleotide from 1.5.3 (SEQ ID NO.:51), 1F5 (SEQ ID NO.:53), Leu16 (SEQ ID NO.:52), rituximab, ofatumumab, veltuzumab, or ocrelizumab.

In still further embodiments, a binding domain comprises (a) a polynucleotide that is at least 60%, at least 70%, at least 75%, at least 80%, at least 85%, at least 90%, at least 95%, or 100% identical to a polynucleotide sequence encoding a $V_L$; e.g., to a $V_L$-encoding polynucleotide from 1.5.3 (SEQ ID NO.:48), 1F5 (SEQ ID NO.:50), Leu16 (SEQ ID NO.: 49), rituximab, ofatumumab, veltuzumab, or ocrelizumab; and (b) a polynucleotide that is at least 60%, at least 70%, at least 75%, at least 80%, at least 85%, at least 90%, at least 95%, or 100% identical to a polynucleotide sequence encoding a $V_H$; e.g., to a $V_H$-encoding polynucleotide from 1.5.3 (SEQ ID NO.:51), 1F5 (SEQ ID NO.:53), Leu16 (SEQ ID NO.:52), rituximab, ofatumumab, veltuzumab, or ocrelizumab. In any of the aforementioned embodiments, polynucleotides encoding each CDR of the $V_L$, $V_H$, or both comprises zero changes or at most one to six nucleotide changes, as compared to a polynucleotide encoding a parent monoclonal antibody or fragment or derivative thereof that specifically binds to CD20, provided that a binding domain containing the modified $V_L$, $V_H$, or both regions specifically binds CD20 with an affinity similar to the wild type binding domain.

In certain embodiments, a binding domain comprises a polynucleotide that is at least 60%, at least 70%, at least 75%, at least 80%, at least 85%, at least 90%, at least 95%, or 100% identical to a polynucleotide sequence encoding a scFv, e.g., an encoded scFv comprising variable domains from an antibody of 1.5.3 (SEQ ID NO.:45), 1F5 (SEQ ID NO.:47), Leu16 (SEQ ID NO.:46), rituximab, ofatumumab, veltuzumab or ocrelizumab. In each of the aforementioned embodiments, polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody.

In any of the embodiments described herein, a binding domain may consist, comprise, be based on or be derived from a $V_H$, a $V_L$, or both, from rituximab (see, e.g., US 2014/0004037), ocrelizumab (see, e.g., U.S. Pat. No. 8,679, 767), ofatumumab (see, e.g., US 2009/0169550), or veltuzumab (see, e.g., US 2009/0169550), the nucleotide and amino acid sequences of which are herein incorporated by reference in their entirety. Additionally, in any of the methods described herein, a CD20 binding molecule may comprise rituximab, ofatumumab, veltuzumab, or ocrelizumab, or any combination thereof.

For purposes of illustration only, a non-limiting example includes the anti-human CD20 antibody 2H7, or antigen binding domains thereof, as described in more detail in Green, D. J., et al., Comparative Analysis of Bispecific Antibody and Streptavidin-Targeted Radioimmunotherapy for B-cell Cancers, Cancer Res 2016 76(22):6669-6679, incorporated herein by reference in its entirety. In some embodiments, the bispecific affinity reagent that specifically binds CD20 (via the first binding domain) is a fusion protein described in Green, D. J., et al., Cancer Res 2016.

Exemplary domains that bind to CD20 that can serve as (or part of) the first (anti-CD20) binding domain of the anti-CD20 bispecific affinity reagent have at least 80% sequence identity (e.g., about 80%, 85%, 90%, 91%, 92%, 93%, 94%, 95%, 96%, 97%, 98%, 99%, or 100% sequence identity) to a CD20 binding domain included in an amino acid sequence of a bispecific affinity reagent as set forth in one of SEQ ID NO:12 and 14 (which are encoded by the nucleic acid sequences set forth in SEQ ID NOs:11 and 13, respectively).

In some embodiments, the anti-CD20 bispecific affinity reagent comprises an amino acid sequence as set forth in SEQ ID NOs:12 or 14 or comprises an amino acid sequence with at least about 80% identity (e.g., about 80%, 85%, 90%, 91%, 92%, 93%, 94%, 95%, 96%, 97%, 98%, 99%, or 100% sequence identity) to an amino acid sequence of as set forth in one of SEQ ID NO: 12 and 14. In some embodiments, the bispecific affinity reagent consists of or consists essentially of an amino acid sequence as set forth in SEQ ID NOs:12 or 14.

The first and second bispecific affinity reagents can be administered together in a single formulation or separately in individual formulations. If administered separately, the first and second bispecific affinity reagents are typically administered within about 1, 2, 3, 4, 5, 6, 7, 8, 9, 10, 15, or 24 hours of each other. Dosing and formulations are described above.

The method can further comprise administering an effective amount of a clearing agent (CA) after administering the bispecific affinity reagents and before administering the radioactive ligand. The CA is described herein. The selection of CA should be appropriate for the type of bispecific affinity reagent used in the first administration step such that the bispecific affinity reagents unbound to target cellular antigens are removed from circulation before the radioactive ligand is administered.

The at least one radioactive ligand is described above. In some embodiments, the second domains of the first and second bispecific affinity reagents each specifically bind the same radioactive ligand and, thus, only the single radioactive ligand is administered in a sufficient amount to allow the different cell-bound affinity reagents to bind radioactive ligand. In other embodiments, the second binding domains of the first and second bispecific affinity reagents each specifically bind distinct radioactive ligands, in which embodiments both radioactive ligands are administered together or separately, but each in an amount such that each of the respective cell-bound first and second bispecific affinity reagents can also bind a radioactive ligand.

The hematological malignancy in this aspect directed to combination therapies can be a B cell malignancy or other B cell hyperproliferative disorder, such as MM, a lymphoma, or a leukemia. See discussion above, which applies to this aspect.

All pairwise combinations of anti-CD38, anti-BCMA, anti-Muc1, anti-GPRC5D, anti-SlamF7, and anti-CD20 bispecific affinity reagents are contemplated in this aspect of the disclosure.

In one embodiment of the method, the first binding domain of the first bispecific affinity reagent specifically binds CD38 and the first binding domain of the second bispecific affinity reagent specifically binds BCMA. In another embodiment, the first binding domain of the first bispecific affinity reagent specifically binds CD38 and the first binding domain of the second bispecific affinity reagent specifically binds Muc1. In another embodiment, the first binding domain of the first bispecific affinity reagent specifically binds CD38 and the first binding domain of the second bispecific affinity reagent specifically binds SlamF7. In another embodiment, the first binding domain of the first bispecific affinity reagent specifically binds CD38 and the first binding domain of the second bispecific affinity reagent specifically binds GPRC5D. In another embodiment, the first binding domain of the first bispecific affinity reagent specifically binds CD38 and the first binding domain of the second bispecific affinity reagent specifically binds CD20. In a further embodiment, where the first binding domain of the first bispecific affinity reagent specifically binds CD38 and the first binding domain of the second bispecific affinity reagent specifically binds CD20, the hematological malignancy is a lymphoma. In a further embodiment, the lymphoma is an NHL.

In any of the above embodiments, wherein the first binding domain of the first bispecific affinity reagent specifically binds CD38, the method can also further comprise administering ATRA or a functional analog or derivative thereof in an amount sufficient to upregulate expression of CD38 in the malignant cells. More detailed descriptions of the ATRA enhancer, or functional analogs or derivatives thereof, and their use in connection with the steps of the method, are provided above and are equally applicable in these embodiments of the combination method aspect. For example, in some instances, the ATRA or functional analog or derivative thereof can be in liposomal formulation and/or can be administered prior to administration of the two bispecific affinity reagents.

In one embodiment of the method, the first binding domain of the first bispecific affinity reagent specifically binds BCMA and the first binding domain of the second bispecific affinity reagent specifically binds Muc1. In another embodiment, the first binding domain of the first bispecific affinity reagent specifically binds BCMA and the first binding domain of the second bispecific affinity reagent specifically binds SlamF7. In another embodiment, the first binding domain of the first bispecific affinity reagent specifically binds BCMA and the first binding domain of the second bispecific affinity reagent specifically binds GPRC5D. In another embodiment, the first binding domain of the first bispecific affinity reagent specifically binds BCMA and the first binding domain of the second bispecific affinity reagent specifically binds CD20.

In one embodiment of the method, the first binding domain of the first bispecific affinity reagent specifically binds Muc1 and the first binding domain of the second bispecific affinity reagent specifically binds SlamF7. In another embodiment, the first binding domain of the first bispecific affinity reagent specifically binds Muc1 and the first binding domain of the second bispecific affinity reagent specifically binds GPRC5D. In another embodiment, the first binding domain of the first bispecific affinity reagent specifically binds Muc1 and the first binding domain of the second bispecific affinity reagent specifically binds CD20.

In any of the above embodiments, wherein the first binding domain of the first bispecific affinity reagent specifically binds BCMA or Muc1, the method can also further comprise administering a GSI in an amount sufficient to upregulate expression of the BCMA or Muc1 in the malignant cells. More detailed descriptions of the GSI enhancer and its use in connection with the steps of the method, are provided above and are equally applicable in these embodiments of the combination method aspect.

In one embodiment, the first binding domain of the first bispecific affinity reagent specifically binds SlamF7 and the first binding domain of the second bispecific affinity reagent specifically binds CD20. In another embodiment, the first binding domain of the first bispecific affinity reagent specifically binds SlamF7 and the first binding domain of the second bispecific affinity reagent specifically binds GPRC5D.

Exemplary Therapeutic Combinations

Illustrative, non-limiting embodiments of methods of this disclosure are described. Further definition for various elements is provided above.

In one embodiment, the disclosure provides a method of treating a malignancy characterized by expression of CD38. The method comprises administering to the subject an amount of all trans retinoic acid (ATRA), or functional derivatives or analogs thereof, sufficient to upregulate expression of CD38 in the malignant cells, as described above. The method also comprises administering to the subject a therapeutically effective amount of a bispecific affinity reagent comprising a first binding domain that specifically binds to CD38 and a second binding domain that specifically binds to a radioactive ligand. After administering the bispecific affinity reagent, the method comprises administering to the subject a therapeutically effective amount of a corresponding radioactive ligand.

In another embodiment, the disclosure provides a method of treating a malignancy characterized by expression of GPRC5D. The method comprises administering to the subject an amount of ATRA, or functional derivatives or analogs thereof, sufficient to upregulate expression of GPRC5D in the malignant cells, as described above. The method also comprises administering to the subject a therapeutically effective amount of a bispecific affinity reagent comprising a first binding domain that specifically binds to GPRC5D and a second binding domain that specifically binds to a radioactive ligand. After administering the bispecific affinity reagent, the method comprises administering to the subject a therapeutically effective amount of a corresponding radioactive ligand.

The ATRA or functional derivatives or analogs thereof for the above embodiments can be administered before or concurrently with the bispecific affinity reagent. In some embodiments, the ATRA or functional derivatives or analogs thereof is administered prior to the bispecific affinity reagent by about 24 hours or less. In further embodiments, the ATRA or functional derivatives or subunits thereof are administered in a liposomal formulation.

In another embodiment, the disclosure provides a method of treating a malignancy characterized by expression of BCMA. The method comprises administering to the subject an amount of gamma secretase inhibitor (GSI) sufficient to upregulate expression of BCMA in the malignant cells, as described above. The method also comprises administering to the subject a therapeutically effective amount of a bispecific affinity reagent comprising a first binding domain that specifically binds to BCMA and a second binding domain that specifically binds to a radioactive ligand. The method comprises thereafter administering to the subject a therapeutically effective amount of a radioactive ligand.

The GSI can be administered before, concurrently with, or closely after (within up to 3 hours after) the bispecific affinity reagent. In some embodiments, the GSI is administered prior to the bispecific affinity reagent by about 24 hours or less.

In another embodiment, the disclosure provides a method of treating a malignancy characterized by expression of Muc1. The method comprises administering to the subject an amount of gamma secretase inhibitor (GSI) sufficient to upregulate expression of Muc1 in the malignant cells, as described above. The method also comprises administering to the subject a therapeutically effective amount of a bispecific affinity reagent comprising a first binding domain that specifically binds to Muc1 and a second binding domain that specifically binds to a radioactive ligand. The method comprises thereafter administering to the subject a therapeutically effective amount of a radioactive ligand.

In any of these illustrative embodiments, the methods can further comprise administering an effective amount of a clearing agent (CA) after administering the bispecific affinity reagent and before administering the radioactive ligand.

In any of these illustrative embodiments, the radioactive moiety comprises yttrium DOTA.

In any of these illustrative embodiments, the affinity reagent is a fusion protein and the first binding domain and the second binding domain are separated by a hinge region. The hinge region can comprise a construct selected from an IgG1 Fc fragment, an IgG2 Fc fragment, and IgG3 Fc fragment, and an IgG4 Fc fragment. One or both of the first binding domain and the second binding domain can be an antibody, a functional antibody fragment, functional antibody derivative, as described above. In some embodiments, one or both of the first binding domain and the second binding domain comprise a variable light chain domain and variable heavy chain domain. The variable light chain and variable heavy chain of the binding domain and/or the second binding are separated by a linker domain. In specific embodiments, one or both of the first binding domain and the second binding domain is an scFv. In some embodiments, the scFv is humanized.

Unless specifically defined herein, all terms used herein have the same meaning as they would to one skilled in the art of the present invention. Practitioners are particularly directed to Sambrook J., et al. (eds.) *Molecular Cloning: A Laboratory Manual*, 3rd ed., Cold Spring Harbor Press, Plainsview, New York (2001); Ausubel, F. M., et al. (eds.), *Current Protocols in Molecular Biology*, John Wiley & Sons, New York (2010); and Coligan, J. E., et al. (eds.), *Current Protocols in Immunology*, John Wiley & Sons, New York (2010) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Unless stated otherwise, the term "about" implies minor variation around the stated value of no more than 10% (above or below), such as up to 10% variation above or below the reference sequence, up to 9% variation above or below the reference sequence, up to 8% variation above or below the reference sequence, up to 7% variation above or below the reference sequence, up to 6% variation above or below the reference sequence, up to 5% variation above or below the reference sequence, up to 4% variation above or below the reference sequence, up to 3% variation above or below the reference sequence, up to 2% variation above or below the reference sequence, or up to 1% variation above or below the reference sequence.

Disclosed are materials and compositions that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are provided for the purpose of illustrating, not limiting, the disclosure.

Example 1

This Example describes the production and characterization of a new anti-CD38 bispecific protein that entirely removes biotin binding and SA from PRIT, while maintaining high CD38 binding affinity and high avidity for the radiolabeled second step. We also directly compare therapeutic efficacy of the new CD38-bispecific with the CD38-SA approach. Several PRIT technologies have been developed to facilitate avidity of the radiolabeled second step reagent for the pretargeted tumor-bound antibody. These include the streptavidin-biotin and bispecific antibody approaches used here; complementary hybridization (Watson-Crick pairing) of phosphorodiamaidate morpholino DNA oligomers; and cyclooctene-modified Abs binding to radiolabeled tetrazine ligands. While prior studies show that all PRIT methods are superior to single-step RIT, no head-to-head comparisons have examined which PRIT method is most promising for clinical development of CD38 targeting. We present a comparative analysis of the biodistribution and therapeutic efficacy of the two most popular PRIT strategies. Our findings demonstrate that efficacy, reduced immunogenicity, and absence of interference from endogenous biotin all make anti-CD38 bispecific PR IT an excellent candidate for clinical translation.

Methods

Construction of Anti-CD38 Bispecific Ab and DOTAY-Dextran Clearing Agent

Methods detailing the construction of the 028-Fc-C825 bispecific (anti-CD38 x anti-Y-DOTA) fusion gene, isolation of CHO cell clones stably expressing the 028-Fc-C825 bispecific Ab, purification of the bispecific Ab, and synthesis of the DOTAY-Dextran (DYD) clearing agent (CA) are described herein. Construction of the control, 2H7-Fc-C825 (anti-CD20 x anti-Y-DOTA) bispecific was described previously in Green DJ, et al. Comparative Analysis of Bispecific Antibody and Streptavidin-Targeted Radioimmunotherapy for B-cell Cancers. *Cancer Res.* 76(22):6669-6679, 2016, incorporated herein by reference in its entirety.

1) Construction of the 028-Fc-C825 bispecific (Anti-CD38 x anti-Y-DOTA) fusion gene A plasmid harboring a C825 ds-scFv gene, an affinity-improved 2D12.5 antibody, was generated (Orcutt KD, et al. Engineering an antibody with picomolar affinity to DOTA chelates of multiple radionuclides for pretargeted radioimmunotherapy and imaging. *Nucl Med Biol.* 2011; 38(2):223-233; and Orcutt KD, et al. Effect of small-molecule-binding affinity on tumor uptake in vivo: a systematic study using a pretargeted bispecific antibody. *Mol Cancer Ther.* 2012; 11(6):1365-1372). Fragments of an anti-CD38 human antibody (028) variable regions (Vl and Vh) were obtained by PCR using a set of overlapped oligonucleotides designed based on published data by GenMab (Copenhagen, DK) (de weers MW, T.; et al., Antibodies against human CD38. In: Office UPaT ed. USPTO. Vol. US 2013/0209355 A1. United States: GENMAB A/S; 2013.). The fragments were assembled using an scFv containing a 25-mer Gly4Ser linker between Vl and Vh to generated a plasmid Q100-3. The 028 scFv fragment (HindIII-XhoI) was prepared by PCR from Q100-3 using oligos YL835 (AGACCCAAGCTTGCCGC-CATGGATTTTCAAGTGCAGATTT) (SEQ ID NO:37) and YL827 (TTTGGGCTCGAGTGAAGAGACGGTGAC-CATTGTCCC) (SEQ ID NO:38) followed by restrictions with HindIII and XhoI. The fragment (HindIII-XhoI) was cloned into the expression vector 089-1-6 at the same sites resulting in an R6-1 construct carrying the 028-Fc-C825 bispecific anti-CD38 and the anti-Y-DOTA fusion gene.

2) Isolation of CHO cell clones stably expressing the 028-Fc-C825 bispecific Ab

R6-1 plasmid DNA was prepared using an endotoxin-free maxi preparation kit (#12362, QIAGEN). The plasmid DNA (250 µg) was linearized with the AscI restriction enzyme at the 5' nonessential region of the CMV promoter. The DNA was purified by phenol extraction and NaOAc/ethanol precipitation. The linearized DNA was re-suspended in 400 µL and maintained in logarithmic growth in Excell 302® complete medium (CM) supplemented with glutamine (4 mM), pyruvate, recombinant insulin (#12585-014, Invitrogen) and penicillin-streptomycin including 1×HT supplement (#11067-030, Invitrogen). For each transfection $2 \times 10^7$ cells were harvested and resuspended in 400 µL complete medium with HT supplement. The AscI-linearized DNA was added to CHO cells in a total volume of 0.8 mL and transferred into a cuvette (4 mm gap) for electroporation using the Gene Pulser Xcell™ transfection apparatus (Bio-Rad) at 280 volts, 950 microFarads. Transfected cells were incubated in non-selective media overnight and plated in 96-well flat bottom plates (Costar) at various dilutions. 50 nM methotrexate (#045K1335, Sigma) without HT supplement. Plated cells were fed every five days until colonies appeared Culture supernatants from master wells were screened for expression of fusion protein using an anti-human Fc sandwich ELISA. Clones with the highest expression of the bispecific fusion protein were expanded using progressively increasing concentrations of methotrexate, from 50-500 nM. Supernatants were measured for Fc fusion protein expression using sandwich ELISA assay.

3) Expression and purification of 028-Fc-C825 bispecific Ab

Cells ($10^7$) of a high expressing clone, 38G11/500, were thawed, washed with RPMI-10% FBS medium, re-suspended in 10 mL Excell 302© CM containing 50 nM MTX (CM+MTX) in a T25 flask, and incubated at 37° C. with 5% $CO_2$ overnight. Cells were pelleted and transferred to a T75 flask containing 30 mL CM+MTX, then expanded by passaging every 3-4 days in T175 flasks with 100 mL CM+MTX. Expanded cells were diluted into 40 T175 flasks with 100 mL per flask CM+MTX at a density of $1 \times 10^5$ cells/mL and incubated 14 days. Supernatants were collected and filtered through 0.22 µm Millipore PES membrane filter units. The pH of the supernatant was adjusted to 8.0 with 1M $Na_2CO_3$ and sodium azide was added to a final concentration of 0.1%. Conditioned supernatant was loaded on a 12-mL protein A-agarose (IPA 400HC crosslinked agarose) column (#10-2500-03, RepliGen Bio Processing) and washed with 10-column volumes of PBS (~120 mL) by gravity flow. The 028-Fc-C825 fusion protein was eluted with 0.1M sodium citrate buffer at pH 3.6. Concentration of the eluted protein in each fraction (~1 mL size) was measured at 280 nm using a Nanodrop spectrometer. Fractions containing the fusion protein were pooled and dialyzed against PBS overnight at room temperature. The final fusion protein was sterile filtered through 0.1 µm PVDF filter units and stored at 4° C.

4) Synthesis of a DOTAY-Dextran (DYD) clearing agent (CA) for the 028-Fc-C825 bispecific Ab Amino dextran 500kD, 30.5 mg, (Life Technologies) was reacted with 6.1 mg of DOTA-SCN (mw=697) in 6 mL DMSO with 11.4 µL of triethylamine overnight at room temperature, as previously described (Orcutt KD, et al., *Mol Cancer Ther.*, 2012; 11(6):1365-1372). The mixture was then diluted with 84 mL 0.4 M sodium acetate pH 5.2, and 100 eq of yttrium nitrate (336 mgMW 383.01) was added and incubated overnight at 37° C. with gentle tumbling, then concentrated in a Vivaspin 20 unit. The mixture was placed in a Slide-a-Lyzer and dialyzed against 2L of water for 3 days before drying on a Biotage evaporator. The dried material was dissolved in 2 mL PBS and passed over a BioRad EconoPak 10DG column, then again reduced to 2 mL on the evaporator and run over another 10 DG column in PBS. Dextran fractions were combined, dialyzed against water for 9 buffer changes over 5 days, again dried on the evaporator and exposed to high vacuum overnight (23 mg). The dried compound was weighed, re-suspended in saline at 4 mg/mL and sterile filtered.

Streptavidin-Biotin Pretargeting Reagents

Conjugates of the OKT10 anti-CD38 monoclonal antibody and streptavidin were synthesized, purified and characterized as previously published. See, e.g., Press OW, et al., A comparative evaluation of conventional and pretargeted radioimmunotherapy of CD20-expressing lymphoma xenografts. *Blood.* 2001; 98(8):2535-2543; and Pagel JM, et al. Comparison of anti-CD20 and anti-CD45 antibodies for conventional and pretargeted radioimmunotherapy of B-cell lymphomas. Blood. 2003; 101(6):2340-2348. A synthetic, dendrimeric CA containing 16 N-acetylgalactosamine residues and a single biotin residue per molecule (NAGB) was obtained from Aletheon Pharmaceuticals (Seattle, WA) for use with the OKT10-SA conjugate.

Radiolabeling of DOTA-Biotin with Yttrium-90

$^{90}$Y (PerkinElmer, Seattle, WA) labeling of DOTA-Biotin was performed using 12 mg/mL DOTA-Biotin, 500 mmol/L ammonium acetate pH 5.3 and $^{90}$Y heated for 60 minutes at 84° C. After cooling to room temperature, 100 mmol/L DTPA was added and labeling efficiency determined using avidin-agarose beads (Press OW, et al., *Blood.* 2001).

Cell Culture

The human multiple myeloma cell lines H929, U266Bland RPMI-8226 were obtained from the American Type Culture Collection (ATCC, Manassas, VA). These lines and the CD38+, CD20-human Burkitt lymphoma (BL) cell line Namalwa were authenticated by DNA profiling (ATCC kit 135-XV), tested for mycoplasma, and maintained in log-phase growth at >95% viability (trypan-blue exclusion) in RPMI 1640 media supplemented with 10% fetal bovine serum, 50 U/mL penicillin G, and 50 µg/mL streptomycin sulfate, for no more than 6 weeks after thawing.

Flow Cytometry-Based Bifunctional Binding Assay

Log-phase growth H929 cells ($0.5 \times 10^6$/group) were harvested and washed once with 1 mL of HBSS-2% FBS (HBSS) buffer. For CD38 blocking groups, cells were resuspended in 40 µL of HBSS buffer containing 40 µg of daratumumab (Janssen R&D, Raritan, NJ) and incubated at 4° C. for 30 min. Then 2 µg of bispecific fusion protein and 1 µg of Y-DOTA-biotin were added to all groups and cells incubated at 4° C. for 30 min, followed by two washes. Recovered cells were resuspended in 40 μL of HBSS buffer containing 2 μL of PE-labeled streptavidin (#60669, AnaSpec Inc., Fremont CA), incubated at 4° C. for 30 min, washed three times, resuspended in 500 μL of PBS buffer containing 1% formaldehyde and analyzed on a Guava Easycyte™ mini cytometer.

Mouse Xenograft Models

Female FoxN1Nu athymic nude mice (Envigo, Hayward, CA) were maintained under standard protocols approved by the FHCRC Institutional Animal Care and Use Committee (JACUC). CD38+ tumor cells ($10^7$) were injected subcutaneously in the right flank 7-11 days prior to experiments to produce 50-80 $mm^3$ tumor xenografts. To attenuate tumor rejection due to natural killer cell activity, mice were injected intraperitoneally with anti-asialoGM1 antibody (986-10001, Wako, Richmond, VA) 1 day prior to tumor implantation, 5 days later and weekly thereafter. All mice were placed on a biotin-deficient diet (23979, TestDiet, Richmond, IN) 7 days prior to PRIT studies.

Blood Clearance and Biodistribution Studies

Groups of 3-5 mice bearing H929 flank tumors were injected via the tail vein (i.v.) with 2.8 nmol (210 to 420 μg) of 028-Fc-C825 (CD38 bispecific) or 2H7-Fc-C825 (CD20 control bispecific). Optimal Ab dosing was determined in prior experiments. Green DJ, et al. A preclinical model of CD38-pretargeted radioimmunotherapy for plasma cell malignancies. Cancer Res. 2014; 74(4):1179-1189; Green DJ, et al. Comparative Analysis of Bispecific Antibody and Streptavidin-Targeted Radioimmunotherapy for B-cell Cancers. Cancer Res. 76(22):6669-6679, 2016. Twenty-three hours later mice were injected with 5 μg of DYD CA, followed 1 hour later by 1.2 nM (2 μg) DOTA-biotin labeled with 20 to 40 μCi (0.74-1.48 MBq) of $^{90}Y$. For blood clearance studies, retro-orbital blood sampling was performed at serial time points up to 24 hours after $^{90}Y$ injection. For biodistribution studies, blood samples, tumors, and body organs were harvested at 6 to 120 hrs. $^{90}Y$ dose in each tissue sample was counted on a gamma counter and the percent of injected dose per gram (% ID/g) calculated. Hui TE, et al. A mouse model for calculating cross-organ beta doses from yttrium-90-labeled immunoconjugates. Cancer. 1994;73(3 Suppl):951-957.

Dosimetry: Estimating Absorbed Doses of Radioactivity in Tissues

Mean absorbed doses to organs and tissues were calculated from the activity over time curves generated in biodistribution experiments. The calculations estimate organ self-dose plus cross-organ dose by accounting for organ mass, specific absorbed energy fraction, the emission spectrum of the radionuclides, and the beta particle absorbed fractions for small organs (Hui TE, et al., Cancer 3(3 suppl):951-957, 1994). The results were expressed as radiation absorbed dose (gray) per unit administered activity (per millicurie).

Therapy Studies

Therapeutic efficacy of CD38 bispecific and CD38-SA PRIT were assessed in groups of 8-10 mice (sample size determined by power analysis) bearing flank H929 or Namalwa xenografts. Mice were randomized into groups with equivalent mean tumor volumes, and treatments administered as in biodistribution studies (above), with the addition of a CD38-SA (OKT10-SA) Ab treatment group that received 50 μg of NAGB as CA. All groups received second step DOTA-biotin labeled at 600, 1000 or 1200 μCi of $^{90}Y$ (22.2, 37 or 44.4 MBq). Tumor size and body weight were measured three times a week following treatment. Mice were euthanized when they experienced excessive weight loss, hind limb paralysis, or exceeded tumor volume limits per IACUC requirements.

Statistical Analyses

In murine xenograft studies, treatment effects on tumor growth rate were determined by first calculating tumor growth rate for each mouse as area under the curve (AUC) of tumor volume over time, standardized for number of days the mouse was alive. Treatment effects on standardized tumor AUC were then determined using analysis of variance. Treatment effects on mouse survival were determined by log-rank comparisons of Kaplan-Meier survival functions. Analyses were performed using JMP 12.2.0 (SAS Institute, Cary, NC) and GraphPad Prism 7 (GraphPad software, La Jolla, CA).

Results

Figure 1B:
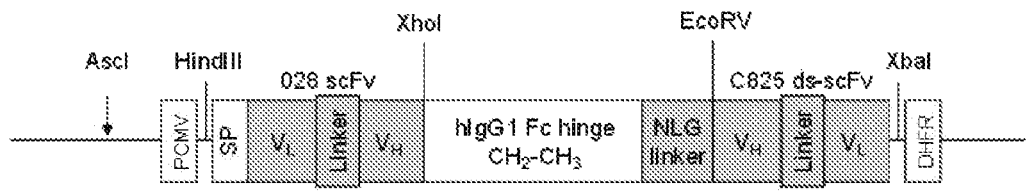
Figure 1B:
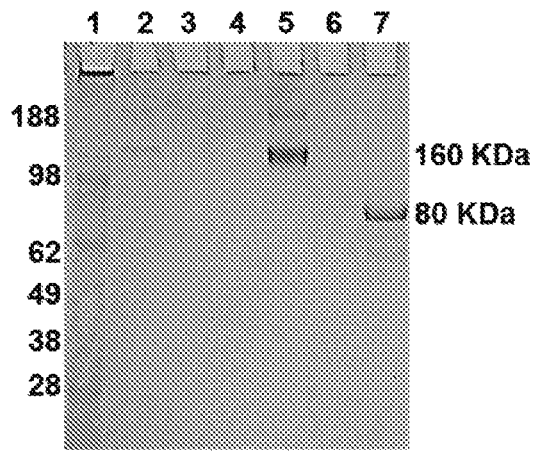
Figure 1C:
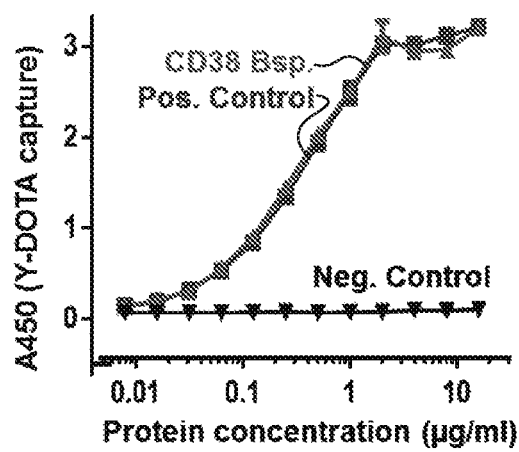
Figure 1D:
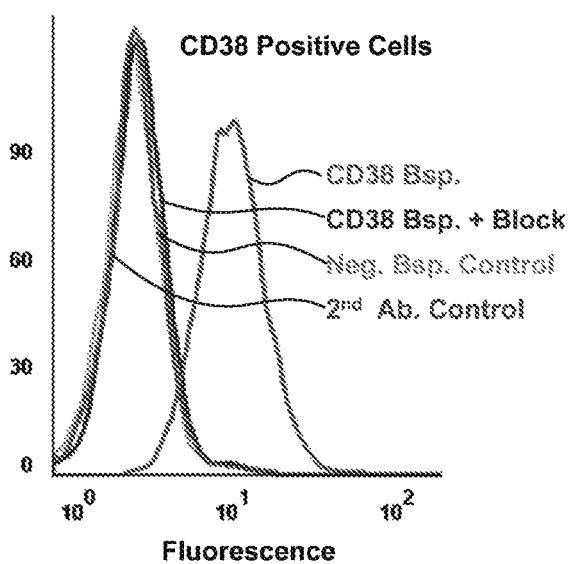
Figure 1E:
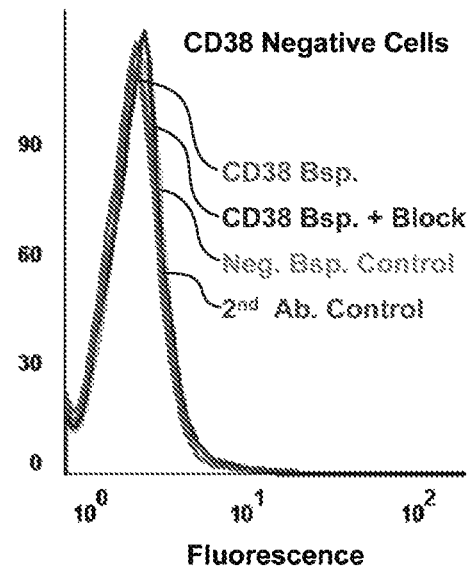

Engineering, Expression, Purification and In Vitro Testing of the Anti-CD38, 028-Fc-C825 Bispecific Protein The 028-Fc-C825 bispecific antibody fusion protein, designed to recognize the CD38 surface antigen and the yttrium-DOTA ligand, was constructed by fusing DNA fragments encoding scFv of the 028 anti-CD38 human antibody and the ds-scFv of the affinity-enhanced C825 antibody to both sides of a human IgG1 Fc containing a NLG linker (FIG. 1A). CHO-DG44 cells were transfected with the fusion construct DNA and high-expressing clones were selected using methotrexate. The monomeric bispecific protein spontaneously dimerized to form a 160-KDa molecule, which was purified from culture supernatants by affinity chromatography and characterized by SDS-PAGE (FIG. 1B) ELISA showed that the bispecific captured the Y-DOTA ligand in a concentration-dependent fashion (FIG. 1C). Bifunctional flow cytometry analysis demonstrated that the bispecific bound only to cells expressing CD38, that binding was blocked by unmodified anti-CD38 monoclonal antibody (mAb) binding the same epitope, and that the bispecific captured the Y-DOTA ligand (FIGS. 1D, 1E). The anti CD38 mAb OKT10 did not block cell binding of the CD38 bispecific, indicating that the binding epitopes did not overlap (FIG. 8).

Figure 2:
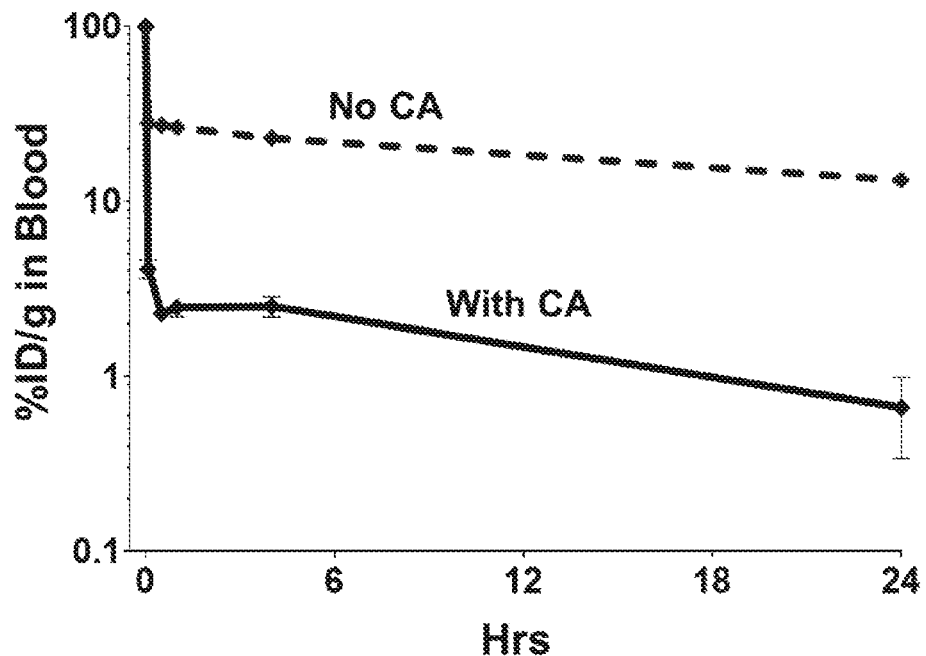
FIG. 2. DOTAY-Dextran clearing agent (CA) effectively clears circulating CD38 bispecific protein from the bloodstream. Athymic nude mice (n=3-5 per group) were injected at −24 hrs with 1.4 nM CD38 bispecific protein (028-C825), then at −1 hr with 5 μg CA, and at 0 hrs with $^{90}$Y-DOTA-Biotin. Controls received no CA. Percent injected dose per gram (% ID/g) was determined from retro-orbital venous samples taken at serial time points starting 5 min after the $^{90}$Y-DOTA-Biotin injection. Error bars=1 SEM.

In Vivo Pharmacokinetics (PK) and Blood Clearance of the CD38 Bispecific Protein PK analysis of the CD38 bispecific protein required our standard, 2-step PRIT protocol, because direct radioiodination of the bispecific protein impaired binding. For PRIT, mice were injected first with the unlabeled protein, followed 23 hours later with CA, then one hour later with $^{90}Y$-DOTA-Biotin. Blood samples were taken at 5 min, 30 min, and 1, 4 and 24 hrs after the $^{90}Y$ injection. FIG. 2 demonstrates that without CA, blood clearance of $^{90}Y$ was 72.8% ID/g after 30 min and 86.8% after 24 hr. With 5 μg CA, clearance was 97.8% ID/g at 30 min and 99.3% after 24 hr. We additionally tested increasing doses of CA; all doses produced virtually identical results (e.g., clearance using 32 μg CA was 98.2% IG/g at 30 min and 99.8% after 24 hr, data not shown). We therefore used the 5 μg dose for further experiments.

Figure 3A:
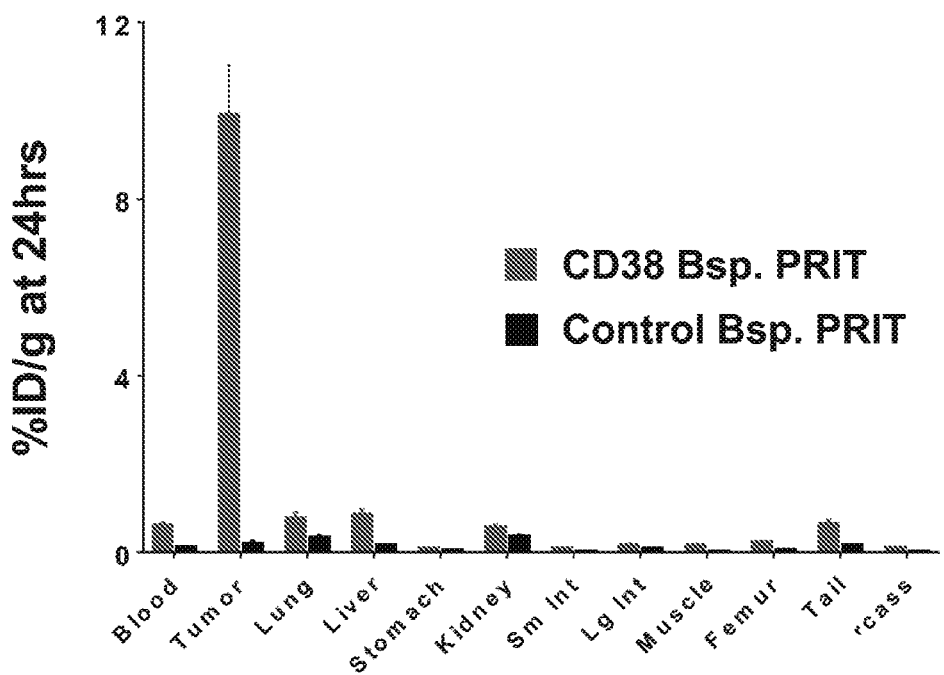
FIGS. 3A-3C. Biodistribution and pharmacokinetics of $^{90}$Y-DOTA-Biotin using CD38-Bispecific PRIT. Athymic nude mice (n=5 per group) bearing H929 (MM) xenografts ($10^7$ cells injected in the right flank) were injected at −24 hrs with 2.8 nM pretargeting Ab (either CD38 bispecific=028-C825, or control bispecific [targeting CD20]=2H7-C825), then at −1 hr with CA, and at 0 hrs with 90Y-DOTA-Biotin. (3A) Blood, tumor and normal organ specimens were taken 24 hrs after radioactivity injections. (3B) and (3C) Comprehensive tissue biodistributions were obtained at sequential time-points 6, 24, 48 and 120 hrs after $^{90}$Y-DOTA-Biotin injection, using (3B) CD38 or (3C) control bispecific PRIT. Legend (3C) also applies to non-target tissues in (3B). Error bars=1 SEM.
Figure 3B:
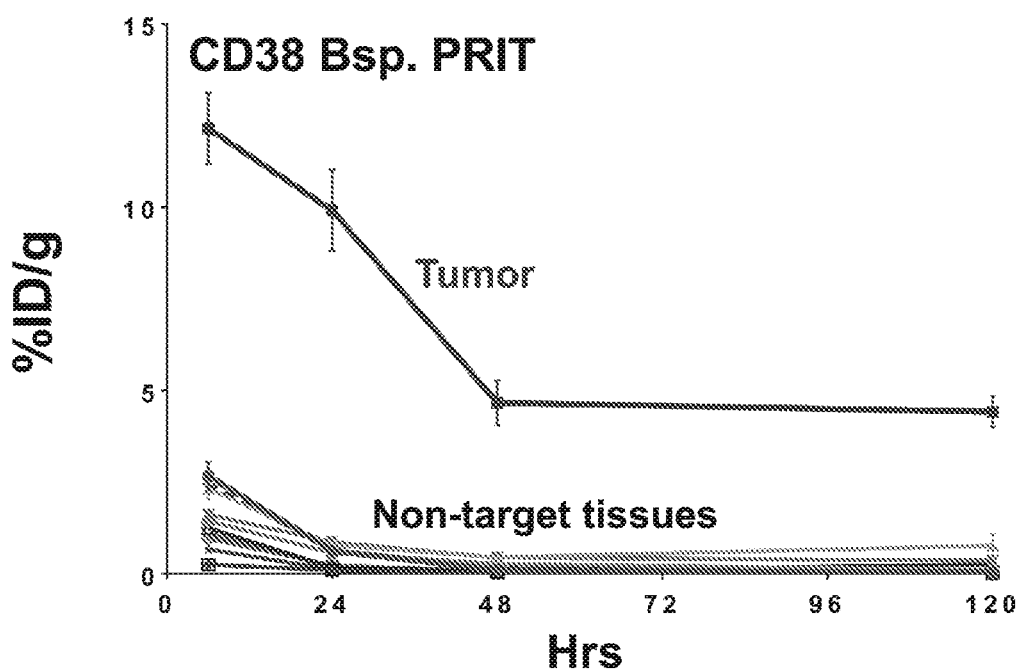
Figure 3C:
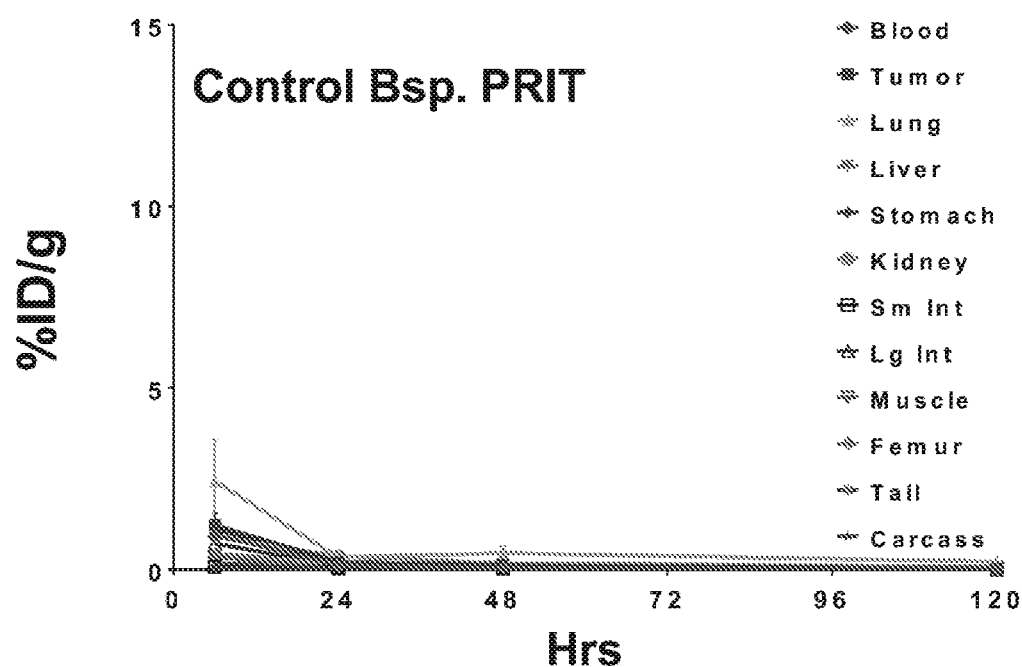

In Vivo Biodistributions of Radioactivity Demonstrate Favorable Tumor Targeting and Retention Using CD38 Bispecific PRIT Biodistributions of radioactivity in blood, tumors (H929 xenografts), and normal organs were compared between CD38 bispecific PRIT and control (CD20-targeted) bispecific PRIT (FIG. 3A). Tumor bearing mice were injected at −24 hr with unlabeled protein, at −1 hr with CA, then at 0 hr with $^{90}Y$-DOTA-Biotin. Assessed 24 hrs after $^{90}Y$-DOTA-Biotin injection, tumor-to-normal tissue ratios of absorbed radiation were 16:1 for blood, 14:1 for lung, 12:1 for liver and 19:1 for kidney for the CD38 bispecific group (FIG. 3A). For the control bispecific group, ratios were <2:1 for the same tissues (FIG. 3A). We also evaluated radioactivity biodistributions over time, taking tissues 6, 24, 48 and 120 hrs after $^{90}$Y-DOTA-Biotin injections. These studies confirmed the tumor specificity of CD38 bispecific PRIT, and further demonstrated high retention of radiation in tumors over time (FIG. 3B). Control bispecific PRIT showed no tumor targeting or retention (FIG. 3C).

Dosimetry

Figure 4:
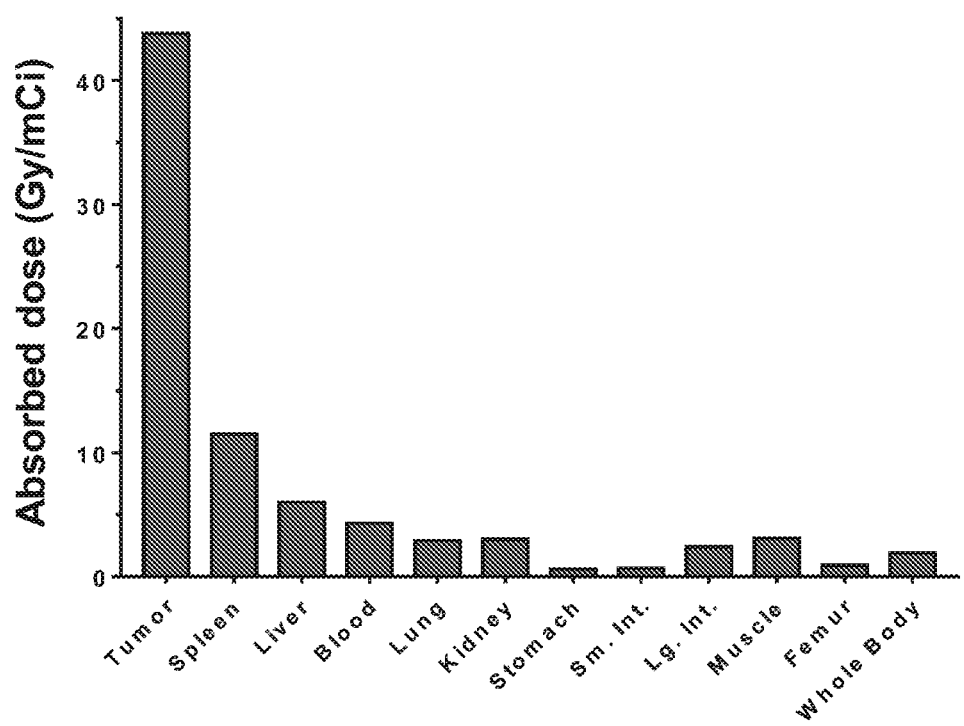
FIG. 4. Dosimetry of $^{90}$Y-DOTA-Biotin using CD38-Bispecific PRIT. Dosimetry, absorbed radiation dose per unit administered activity (Gy/mCi), was calculated for tumor and normal organs during the first 120 hrs after radioactivity injections (tissues per FIG. 3B). Dosimetry includes organ self-dose absorbed fraction plus beta particle cross-organ absorbed fraction 46. Absorbed radiation dose to tumor was 44 Gy/mCi, in contrast to 6, 3, and 3 Gy/mCi for liver, lung and kidney, respectively.

We estimated radiation-absorbed doses to tumors, whole body, and 10 normal tissues from time-activity curves generated in CD38 bispecific biodistribution experiments, using a dosimetry method that calculates both organ self-dose absorbed fractions and 0-particle cross-organ dose contributions, per unit of administered activity (FIGS. 3B and 4) (see, e.g., Hui TE, et al. Cancer 3(3 suppl):951-957, 1994). Absorbed radiation dose to tumor was 43.8 Gy/mCi, and tumor-to-normal organ ratios of absorbed dose were 51:1 for the femur, 23:1 for the whole body, 15.4:1 for the lung, 15:1 for the kidneys, 10:1 for the blood, and 7.4:1 for the liver (FIG. 4).

Therapy Studies

Figure 5A:
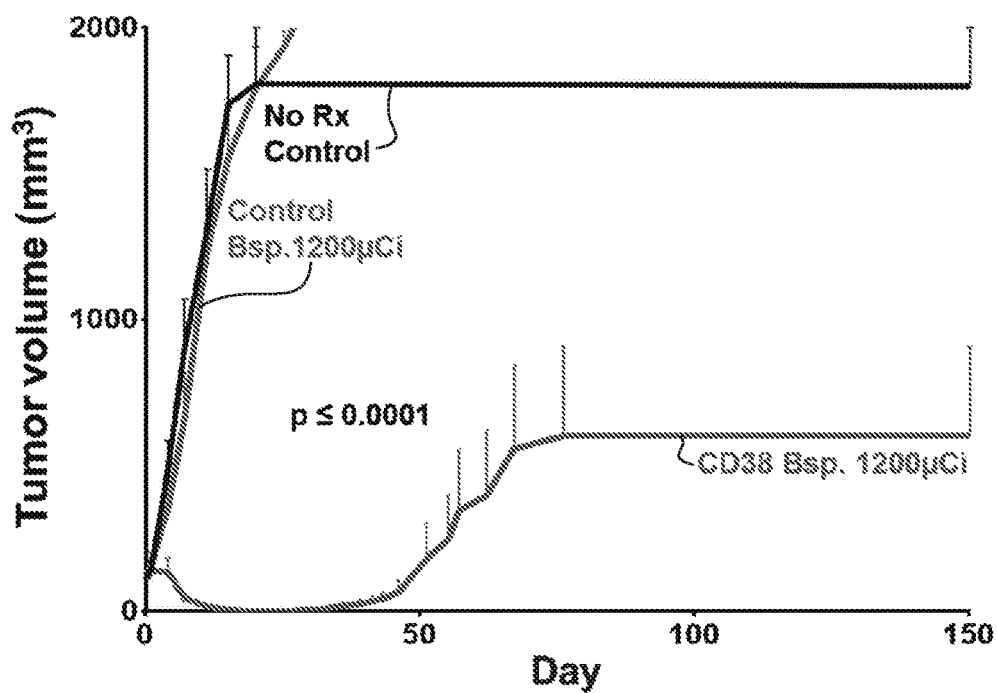
FIGS. 5A and 5B. Effect of CD38 bispecific PRIT on tumor growth rate and survival of mice bearing H929 (MM) xenografts. Athymic nude mice (n=10 per group) with H929 xenografts were injected at −24 hrs with a pretargeting protein (CD38 bispecific or control [anti-CD20] bispecific), then at −1 hr with CA, and at 0 hrs with 1200 μCi $^{90}$Y-DOTA-Biotin. Tumor volume was monitored three times weekly and mice euthanized when tumor size reached IACUC mandated limits. For tumor volume graphics, data from euthanized mice were retained until all mice in a group died. (5A) Treatment with CD38 bispecific PRIT resulted in 100% CRs during days 15-30 and 80% long-term CRs. This contrasted with control mice, where 90% of untreated and 100% of control bispecific groups died of tumor progression by day 27 ($p \le 0.0001$, CD38 bispecific vs. either control group, error bars=1 SEM). One untreated mouse exhibited spontaneous tumor remission. (5B) Kaplan-Meier analysis indicates that CD38 bispecific PRIT significantly improved survival over controls ($p \le 0.0001$), curing 80% of mice. Cure defined as no sign of tumor recurrence at day 150.
Figure 5B:
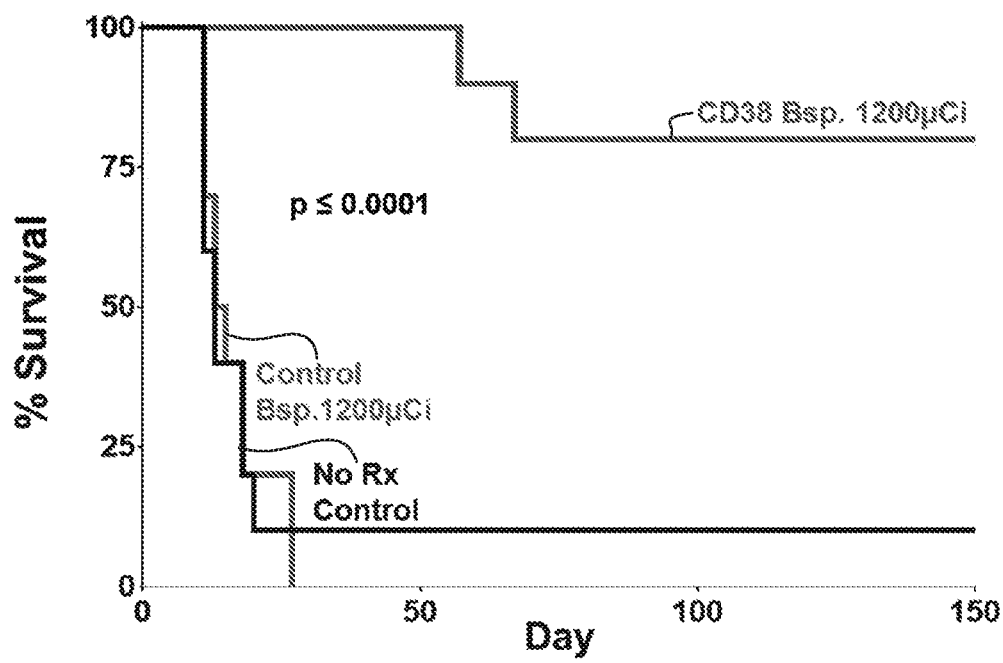
Figure 6A:
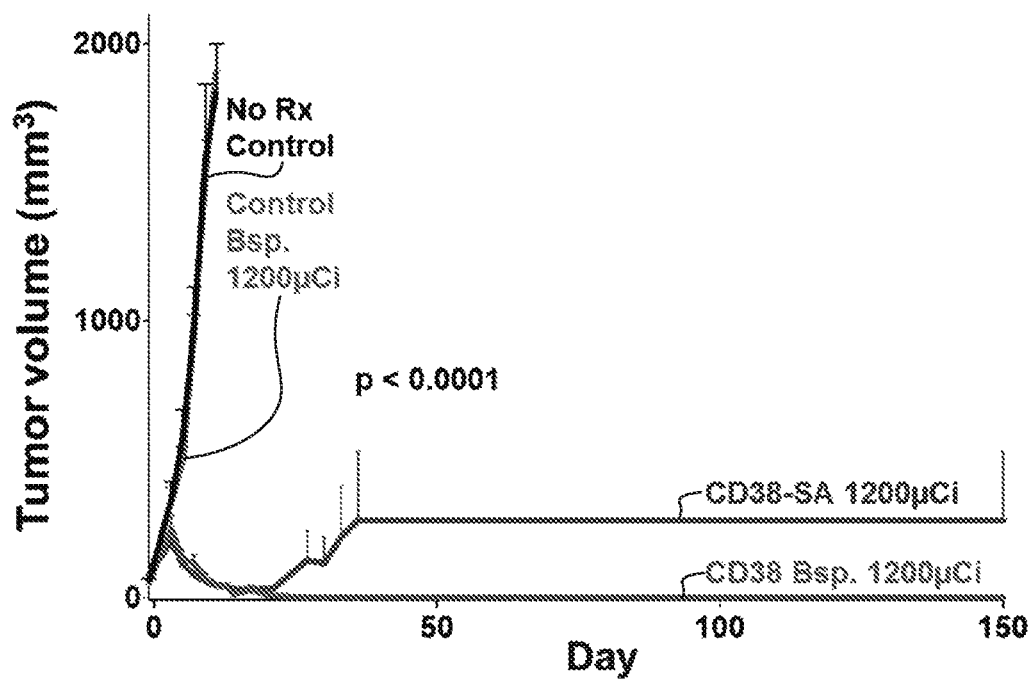
FIGS. 6A and 6B. Comparative effects of CD38 bispecific PRIT and CD38-SA PRIT on tumor growth and survival of mice bearing Namalwa (CD38+BL) xenografts. Athymic nude mice (n=8 per group) with Namalwa xenografts were injected at −24 hrs with a pretargeting protein (CD38 bispecific, CD38-SA, or control [anti-CD20] bispecific), then at −1 hr with CA, and at 0 hrs with 1200 μCi $^{90}$Y-DOTA-Biotin. Tumor volumes were monitored three times weekly and mice euthanized when tumor size reached IACUC mandated limits. For tumor volume graphics, data for euthanized mice were retained until all mice in a group died. (6A) CD38 bispecific PRIT and CD38-SA PRIT each reduced tumor volumes to undetectable levels by day 21, followed by a single tumor recurrence in the CD38-SA group and no recurrences in the CD38 bispecific group. ($p<0.0001$, either CD38 PRIT group vs. either control group, error bars=1 SEM). (6B) Kaplan-Meier survival analysis. CD38 bispecific PRIT cured 75% of mice (all mortality due to early weight loss), while CD38-SA PRIT cured 88% of mice (all mortality due to tumor progression), demonstrating that at this 1200 μCi dose the two CD38 treatments each benefitted survival with high and equivalent efficacy ($p<0.0001$ for either CD38 treatment vs. either control, $p=0.48$ for CD38 bispecific vs. CD38-SA). Cure defined as the absence of tumor recurrence through day 150.
Figure 6B:
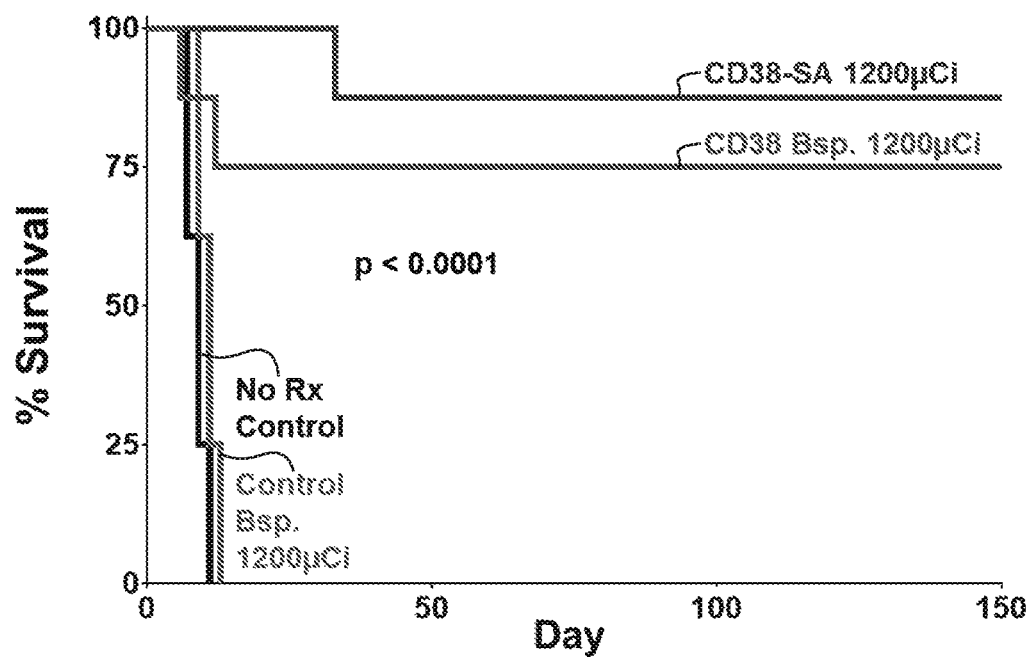

We studied the efficacy of CD38 bispecific PRIT in two xenograft models, and found that optimized PRIT dosing cured at least 75% of mice in every experiment. Athymic mice (n=8-10 per group) bearing H929 MM or Namalwa NHL xenografts were injected first with cold Ab, then 23 hrs later with CA, and then in one more hour with $^{90}$Y-DOTA-Biotin. Previous PRIT studies by our group indicated that 1200 µCi of $^{90}$Y provides the most favorable therapeutic ratio, and we first examined efficacy of the CD38 bispecific Ab at 1200 µCi. In the H929 model, treatment with CD38 bispecific PRIT dramatically reduced tumor growth (FIG. 5A) and increased survival (FIG. 5B) relative to treatment with bispecific control PRIT (1200 µCi) and untreated control groups (p≤0.0002, CD38 bispecific vs. either control). In total, 19 of 20 mice in the 2 control groups died of tumor progression within 30 days (1 untreated mouse showed spontaneous tumor regression), while in the CD38 bispecific group 8 mice sustained complete remissions through the end of the study (150 days) and 2 died of tumor progression, both after day 50. In a second CD38+ tumor xenograft model (Namalwa), we added head-to-head comparisons of the CD38 bispecific Ab versus the CD38-SA (OKT10-SA) Ab, each labeled with 1200 µCi of $^{90}$Y. In this experiment, both CD38 treatments resulted in 100% CRs by day 21, followed by one subsequent relapse in the CD38-SA group and zero relapses in the CD38 bispecific group (FIGS. 6A and 6B). Thus at this dose the two CD38 treatments reduced tumor growth and increased survival with high and equivalent efficacy (p<0.0001 for either CD38 treatment vs. either control, p=0.48 for CD38 bispecific vs. CD38-SA). To further characterize the dose-response relationship of CD38 PRIT, we also evaluated 600 and 1000 µCi of $^{90}$Y pretargeted to xenograft tumors. These reduced dose experiments compared CD38 bispecific PRIT versus CD38-SA PRIT, and both anti-CD38 systems reduced tumor growth (FIG. 7A) while improving survival (FIG. 7B) in a marginally dose dependent manner (p<0.062, PRIT 600 µCi vs. PRIT 1000 p Ci). Importantly, at these reduced doses the CD38 bispecific Ab strongly outperformed CD38-SA, resulting in long-term survival of 61% versus 22%, respectively, with 600 µCi, and 78% versus 47%, respectively, with 1000 µCi (p<0.004, CD38 bispecific vs. CD38-SA). In contrast, all controls, including mice treated with cold (no radiolabel) CD38 bispecific, cold CD38-SA, or control bispecific at 1000 µCi, died of tumor progression by day 15 (FIGS. 7A and 7B, p<0.0001, any CD38 PRIT group vs. any control group).

Toxicity

PRIT using all Abs was well tolerated, with minimal weight loss and recovery to starting weight within 14 days of treatment (FIGS. 9A-9C). Over all studies (FIGS. 5A-7B), 2 of 18 mice treated with CD38 bispecific at 1200uCi and 2 of 18 treated with CD38 bispecific at 1000 uCi died due to low body weight before day 18. All other deaths in all groups resulted from tumor progression. Anecdotal data suggests that early weight loss and mortality may be ameliorated as follows. Between our final two studies we implemented husbandry changes to reduce external radiation exposure from cage mates and bedding; mortality before the changes was 2 of 8 mice and mortality after was 0 of 10 mice for 1000 uCi CD38 bispecific treatments (groups combined in FIGS. 7A and 7B).

DISCUSSION

Combinations of immunomodulatory and proteasome inhibitor based therapies frequently induce remission in MM patients, but relapse is nearly inevitable and the need for development of potentially curative treatments remains critical. Our results demonstrate 75-88% cure rates using PRIT in two CD38 expressing murine xenograft tumor models. These results are consistent with the steep dose-response relationship between radiation and hematologic malignancies. In MM, external beam radiation can cure isolated plasmacytomas and provide sustained local disease control in 98% of lesions receiving >10 Gy and in follicular non-Hodgkin lymphoma, another generally incurable B cell malignancy, external beam radiation can also eradicate disease that is limited to a single site of involvement.

RIT offers a delivery model designed to parlay the unique anti-tumor potency of radiation demonstrated in localized disease to a broader population of patients with multi-focal disease by sparing healthy tissues while delivering a targeted radiation payload directly to malignant cells. Single-step RIT has demonstrated some promise in MM, yet clinical applications have been very limited. Similar to CD20 single-step RIT, enthusiasm may be limited by low tumor-to-normal ratios (e.g. <2.4:1 for kidney, lung and liver in NHL). PRIT methods can greatly improve these therapeutic ratios. In MM models, we previously demonstrated that CD38-SA PRIT provides tumor-to-normal tissue dosimetry ratios of 6:1 for kidney, lung, and liver, and here show that CD38 bispecific PRIT provides ratios of 15:1 for kidney and lung and 7:1 for liver. To our knowledge, we have performed the only studies of PRIT in MM.

Recent clinical successes with unmodified anti-CD38 Mab therapy in MM have motivated ongoing clinical studies of this therapy in B-cell NHL. High density CD38 expression is a common feature of malignant B cells and the predictable growth kinetics associated with NHL cell lines have led to their frequent use in research models for the development of CD38 targeted MM therapy. Despite advances in the management of NHL, nearly 30% of these patients die of progressive disease within 5 years of diagnosis. As in MM, treatment-refractory NHL typically retains sensitivity to radiation, making CD38 PRIT a potentially effective treatment for such patients as well. Beyond tumors that share a common B-cell lineage, CD38 is expressed in most natural killer (NK)/T-cell lymphomas, where 50% of patients die within 5 years and overexpression of CD38 predicts poor outcomes for NK/T-cell lymphoma patients, presenting another potential translational application for CD38 PRIT. A broad range of potential indications for CD38 PRIT increases the probability of successful translation into a commercially viable radioimmunotherapeutic. To further evaluate CD38 as a target for RIT, we are conducting a clinical trial using a CD38 mAb directly conjugated to the alpha-emitter astatine-211 (single-step RIT). We are also developing bispecific fusion protein constructs for alpha emitter delivery which will facilitate head-to-head comparisons of alpha and beta emitter PRIT.

While the preclinical efficacy of PRIT appears clear, concerns have been raised regarding clinical translation. SA is a bacterial protein, and PRIT using SA results in immunogenicity and thus limits the ability to administer multiple cycles of therapy, although two factors may mitigate this concern. First, the immunocompromised status of many patients with hematological malignancies limits immunogenic responses, and second, PRIT is designed to be efficacious following a single dose, as demonstrated in both this manuscript and our previous studies. To reduce these concerns, several methods of modifying SA have been developed, but approaches that eliminate SA would obviate the issue entirely. To achieve this we developed the CD38 bispecific fusion protein, which exploits the same principles as the SA-biotin system, but replaces SA with a humanized yttrium-DOTA capturing C825 disulfide-stabilized scFv (FIG. 1A). A bispecific construct harboring the same anti-yttrium-DOTA (C825) in an immunocompetent murine model (Orozco J J. et al, unpublished) has demonstrated no evidence of toxicity. Reduced immunogenicity may allow for repeat dosing of CD38 bispecific PRIT, and fractionation may offer the opportunity to improve the therapeutic ratio in clinical settings. Our data here however suggest that PRIT is effective and well tolerated as a single-dose therapeutic.

A second concern for SA-PRIT is the potential for endogenous biotin in patient blood and tissues to occupy and block SA binding sites, preventing subsequent binding of the second-step radio-DOTA-biotin reagents. The bispecific approach obviates this concern, as binding of the C825 portion of the bispecific to the DOTA portion of the second-step reagent precludes any possible interference from endogenous biotin.

Figure 7A:
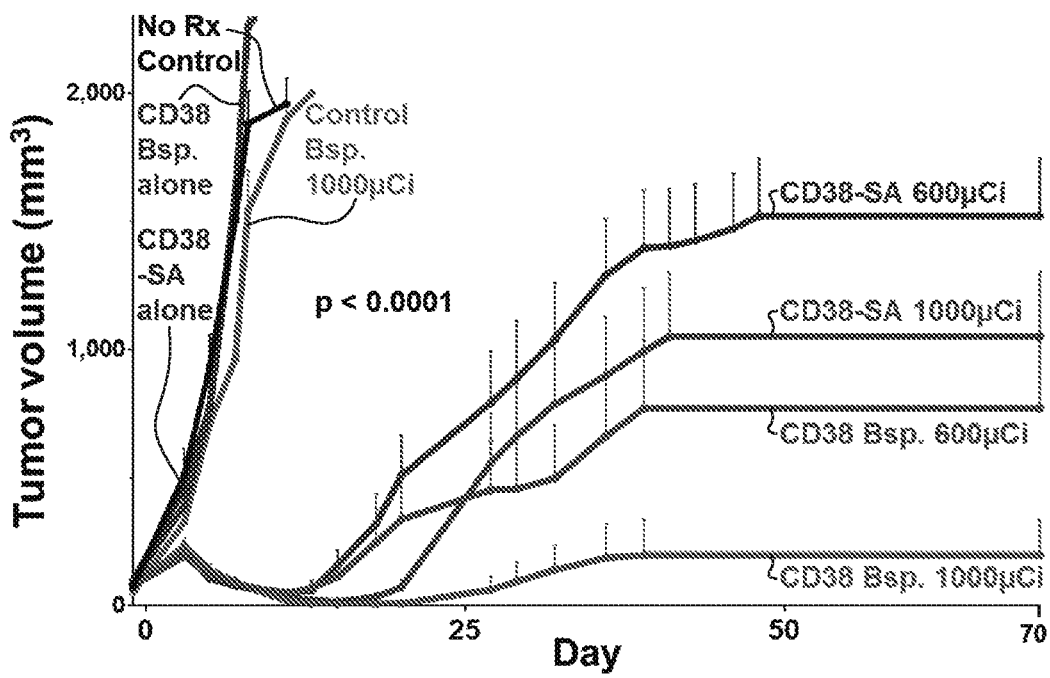
FIGS. 7A and 7B. Comparative dose-response effects of CD38 bispecific PRIT versus CD38-SA PRIT on tumor growth and survival of mice bearing CD38+BL xenografts. These figures present data from two replicate experiments, each using 8-10 athymic nude mice per group. In total, n=18 mice per treatment were injected at −24 hrs with a pretargeting protein (CD38 bispecific, CD38-SA, or control [anti-CD20] bispecific), then at −1 hr with CA, and at 0 hrs with 600 or 1000 μCi $^{90}$Y-DOTA-Biotin. An additional n=10 mice per group received only pretargeting protein (CD38 bispecific or CD38-SA) and CA, with no $^{90}$Y-DOTA-Biotin. (7A) All control mice including untreated, pretargeting protein without $^{90}$Y, and control bispecific 1000 μCi groups, experienced rapid tumor progression and died by day 14. All CD38 PRIT mice showed CR by day 11, and subsequent strongly reduced tumor progression relative to controls (p<0.0001, any CD38 PRIT group vs. any control group). However, CD38 bispecific PRIT outperformed CD38-SA PRIT, the former showing later and fewer tumor progressions in the 600 and 1000 μCi treatment groups (p<0.003, CD38 bispecific vs. CD38-SA). (7B) Kaplan-Meier survival analyses reflect the tumor volume results, showing greatly improved survival in each CD38 PRIT group relative to each control (p<0.0001), and improved survival of CD38 bispecific PRIT mice relative to CD38-SA PRIT mice, across 600 and 1000 μCi levels (p<0.004, CD38 bispecific vs. CD38-SA).
Figure 7B:
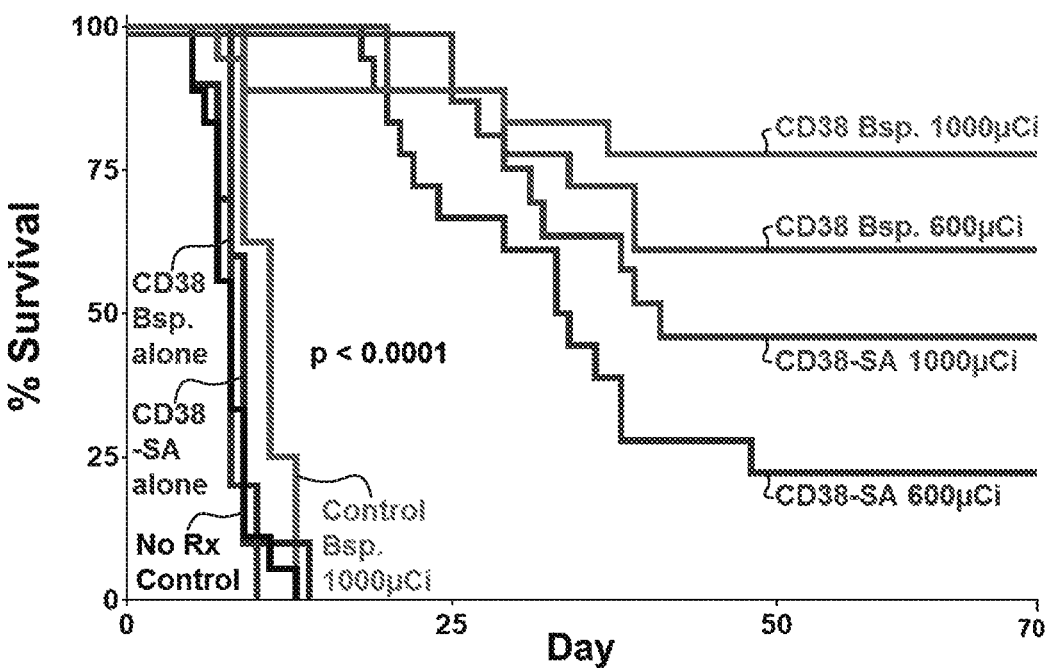

Our data suggest that bispecific PRIT has superior efficacy when compared with CD38-SA PRIT (FIGS. 7A and 7B). The anti-CD38 region of the bispecific protein binds a different epitope of CD38 than the OKT10-SA protein, as demonstrated by the absence of OKT10 mAb blocking of the bispecific CD38 in cell binding assays (FIG. 8). The binding of separate epitopes raises the possibility that the first step CD38 targeting constructs have differing therapeutic effects, but we demonstrated that neither construct has anti-tumor efficacy when administered without radiolabeling (FIGS. 7A and 7B). Alternatively the therapeutic differences may be a consequence of differing in vivo binding efficiencies. The bispecific and SA treatments were designed such that all mice received an equivalent injected protein dose carrying an identical radiolabel dose, but subsequent tumor binding might differ for two reasons. First, it is feasible that CD38-SA binding, and thus PRIT efficacy, was reduced by very low level blocking by residual endogenous biotin in mouse tissues, despite institution of a biotin-free diet. Second, differences in antibody-ligand interaction may be a function of each construct's avidity for its respective epitope, resulting in kinetics that may favor the bispecific.

In conclusion, we have characterized a new CD38 bispecific targeting protein for PRIT of MM and NHL. The bispecific Ab is relatively easy to produce, exhibits excellent blood clearance using an inexpensive clearing agent, and shows excellent tumor-to-normal organ ratios of absorbed activity reflected by favorable dosimetry in murine models. Moreover, the CD38 bispecific rapidly reduced disease burden, and at optimal doses ultimately cured 75-80% of mice in each of two xenograft models with minimal toxicity. CD38-SA was equally effective at the highest radiation dose, but the bispecific's superiority over a range of doses, combined with its reduced risk of immunogenicity and lack of endogenous biotin interference, make the CD38 bispecific a prime candidate for clinical translation.

Example 2

This Example describes an expansion of the findings of Example 1 with the development of a bispecific protein that uses an alternative cancer marker, B cell maturation antigen (BCMA) as the targeting antigen.

As described above, multiple myeloma (MM) is generally incurable and autologous stem cell transplantation (ASCT) remains a standard or care approach to disease management, yet no modification to ASCT conditioning has substantively improved transplant outcome in over 25 years. In Example 1, development of an anti-CD38 bispecific fusion protein is described that resulted in 100% complete remissions (CR) by day 12 in preclinical MM xenograft models, ultimately curing 80% of mice at optimal doses. The high efficacy of bispecific PRIT, combined with its reduced risk of immunogenicity and endogenous biotin interference, make this bispecific approach a very attractive candidate for clinical translation in both transplant, and ultimately non-transplant settings. This Example addresses development of additional bi-specific compositions useful for PRIT that target other cancer antigens to optimize the bispecific PRIT strategy for MM. The project is intended to (1) optimize a B cell maturation antigen (BCMA) Bi-specific FP construct, evaluate biodistribution and therapeutic efficacy in a mouse model, and demonstrate that upregulation of the target further enhances the efficacy of the BCMA FP.

BACKGROUND

The vast majority of the 130,000 patients in the United States living with multiple myeloma (MM) will ultimately die of progressive disease despite high rates of initial response to novel agents. Disease recurrence is presumably a function of malignant plasma cell clones that persist in spite of available therapies. Novel anti-myeloma agents introduced over the past decade have made complete response (CR) possible in a significant subset of patients. Unfortunately, almost all of these individuals ultimately relapse. High dose chemotherapy followed by ASCT increases CR rates and prolongs disease free survival, but relapse remains virtually inevitable and recurrence remains a major shortcoming of all available treatment strategies. The development of bispecific pretargeted radioimmunotherapy to improve outcomes after high dose therapy and ASCT represents an entirely novel approach to the management of MM. ASCT is a standard of care for eligible MM patients, yet over the past two decades there has been no modification to high dose therapy conditioning regimens that has improved post-transplant outcome. Despite the widespread administration of "novel agents", the numbers of ASCTs for MM continues to increase every year, emphasizing the importance of transplantation. The radiosensitivity of malignant plasma cells outside of the bone marrow has been well documented in clinical settings. Local recurrence of solitary extramedullary plasmacytomas occurs in less than 10% of cases after external beam radiation alone. Radiation therapy is also effective as a palliative measure in patients experiencing pain or other sequelae resulting from MM-induced osteolysis. Sustained local disease control and durable symptom relief has been reported for 98% of lesions receiving >10Gy. Steep dose response relationships have been demonstrated for most hematological malignancies, and the impact of radiation dose escalation may be of particular importance in the case of MM. Further, the poor prognosis associated with high risk bone marrow cytogenetics in active MM are not predictive of a decrement in the very high rates of local control and cure after external beam radiation therapy is used to treat solitary extramedullary plasmacytomas with the same cytogenetic derangements. This suggests that the unique attributes associated with the targeted delivery of radiation may augur clinical efficacy even among patients classified as "high risk". Radioimmunotherapy (RIT) selectively delivers radiation to target cells at multifocal disease sites and facilitates escalation to radiation doses not achievable through external beam therapy. The efficacy of RIT in the treatment of hematologic malignancies is well established. RIT has successfully been integrated into stem cell transplant conditioning regimens with a significant improvement in PFS and OS among patients with B cell lymphoma and acute myelogenous leukemia. A limited number of radionuclide based therapies have been explored in the clinical treatment of MM. While each of these radionuclide based approaches has theoretical promise, none have directly targeted radiation to the CD38 antigen on MM cells. We have demonstrated striking therapeutic efficacy with anti-CD38 (OKT10) pretargeted radioimmunotherapy (PRIT) using the β-emitter 90Y directed against MM cells. Objective remissions were observed within 7 days in 100% of the mice treated with 800 µCi to 1200 µCi of anti-CD38 pretargeted 90Y-DOTA-biotin, including 100% complete remissions (no detectable tumor in treated mice compared to tumors that were 2982±1002% of initial tumor volume in control animals) by day 23. Furthermore, 100% of animals bearing H929 MM tumor xenografts achieved longterm myeloma-free survival (>70 days) after an optimal radiation dose, compared to none (0%) of the control animals.

As described in Example 1, a new PRIT approach was developed for the treatment of MM. Specifically an anti-CD38 bispecific fusion protein was developed that eliminates endogenous biotin interference and immunogenic elements. In murine xenograft models of MM, the CD38 bispecific construct demonstrated excellent blood clearance and tumor targeting. In therapy studies, CD38 bispecific PRIT resulted in 100% complete remissions (CR) by day 12 in MM and NHL xenograft models, ultimately curing 80% of mice at optimal doses. In direct comparisons, efficacy of the CD38 bispecific proved equal or superior to streptavidin (SA)-biotin-based CD38-SA PRIT. Each approach cured at least 75% of mice at the highest radiation dose tested (1200 µCi), while at 600 and 1000 µCi doses the bispecific outperformed the SA approach, curing 35% more mice overall (p<0.004). The high efficacy of bispecific PRIT, combined with its reduced risk of immunogenicity and endogenous biotin interference, make the CD38 bispecific an attractive candidate for clinical translation. Critically, CD38 PRIT may benefit patients with unresponsive, high-risk disease, because refractory disease typically retains radiation sensitivity. We posit that PRIT might not only prolong survival, but possibly cure MM. Moreover, we have demonstrated that the anti-CD38 bispecific fusion protein is very effective in eliminating disease in non-Hodgkin lymphoma (NHL) tumor models and commercialization of this approach offers potential therapeutic application in the management of NHL. The bispecific CD38 construct has been vetted in our preclinical models and is ready for comprehensive characterization and scale up to support IND submission.

Approach

To provide an alternative target for therapeutic application of the bispecific PRIT approach, another bispecific fusion molecule was generated that targeted B cell maturation antigen (BCMA) instead of CD38. Exemplary proteins that specifically bind to BCMA, their active binding sites, and representative polynucleotides encoding the BCMA-specific binding proteins are described in more detail in U.S. Provisional Application No. 62/460,612, incorporated herein by reference in its entirety.

Pre-clinical data using BCMA bispecific construct demonstrates efficacy and represents an alternative path to commercialization. Both BCMA and CD38 agents hold significant translational promise. Whereas the restricted nature of BCMA expression allows theoretical advantage for commercial translation specifically in MM, the CD38 bispecific molecule may have broader application in other B cell malignancies.

Antigen Targeting in Multiple Myeloma

An extensive analysis of potential MM surface antigen targets for RIT led to the selection of CD38 and BCMA based consistency of expression on clonal plasma cells and other favorable features. We evaluated BCMA expression in bone marrow obtained from 50 consecutive MM patients at various times prior to, during, and following therapy. We detected variable levels of BMCA on MM cells in 100% of cases, a finding confirmed by others. As described above, several PRIT methods have been developed, each has been shown to be markedly superior to conventional RIT with directly radiolabeled antibodies. All of these strategies administer a derivatized tumor-reactive antibody in a non-radioactive form, allowing it to localize to tumor sites and accumulate without subjecting the rest of the body to nonspecific irradiation. After maximal accumulation of antibody in the tumor, a low molecular weight radioactive moiety with a high affinity for the derivatized tumor-reactive antibody is administered. The small size of the second reagent facilitates rapid tumor penetration, capture and retention by the pre-targeted antibody. Unbound molecules of the radioactive second reagent are so small that they are rapidly cleared from the blood and excreted in the urine. In some PRIT approaches, a "clearing agent" (CA) is injected shortly before the radiolabeled small molecule to accelerate removal of residual unbound antibody from the bloodstream, preventing it from complexing with the radiolabeled second step reagent. Our findings to date suggest biodistribution of radioactivity favors the bispecific antibody approach. We have demonstrated that both streptavidin-biotin and bispecific antibody based PRIT methods are capable of curing 70-100% of animals bearing tumor xenografts when used under optimal conditions, but the expected reduced immunogenicity and absence of potential interference from endogenous biotin-blocking argue in favor of the bispecific antibody approach over SA-biotin PRIT for future clinical trials. In addition, we have demonstrated that the bispecific antibody construct appears to produce less hematologic toxicity than SA-biotin PRIT when studied in a lymphoma model.

Results

Construction of bispecific 028-Fc-C825 (Anti-CD38 x anti-Y-DOTA) and C11-Fc-C825 (Anti-BCMA x anti-Y-DOTA) fusion genes pDG mammalian expression vectors containing anti-CD38 028-hIgG1-hRNase and anti-BCMA C11-hIgG1-hRNase genes under the control of CMV promoters were generated. A plasmid harboring a C825 ds-scFv gene, an affinity-improved 2D12.5 antibody, was generated in the Wittrup lab (MIT). (Orcutt KD, et al. Engineering an antibody with picomolar affinity to DOTA chelates of multiple radionuclides for pretargeted radioimmunotherapy and imaging. *Nuclear medicine and biology.* 2011; 38(2):223-233; and Orcutt KD, et al., Effect of small-molecule-binding affinity on tumor uptake in vivo: a systematic study using a pretargeted bispecific antibody. *Molecular cancer therapeutics.* 2012; 11(6):1365-1372, both incorporated herein by reference in their entireties). A C825 ds-scFv fragment was obtained by PCR from its template plasmid and cloned into a TOPO TA vector (Invitrogen) to generate the 086-2 plasmid. An EcoRV-XbaI fragment was excised from the plasmid 086-2 containing the C825 ds-scFv gene and cloned into the plasmid 022-3-9 at EcoRI-XbaI sites resulting in an 089-1-6 construct carrying either the 028-Fc-C825 bispecific anti-CD38 or C11-Fc-C825 bispecific anti-BCMA (encoding the amino acid sequence set forth in SEQ ID NO:19) and the anti-Y-DOTA Fc-fusion gene (FIG. 1A).

Cell Binding Analysis of Antibody Constructs

Figure 10A:
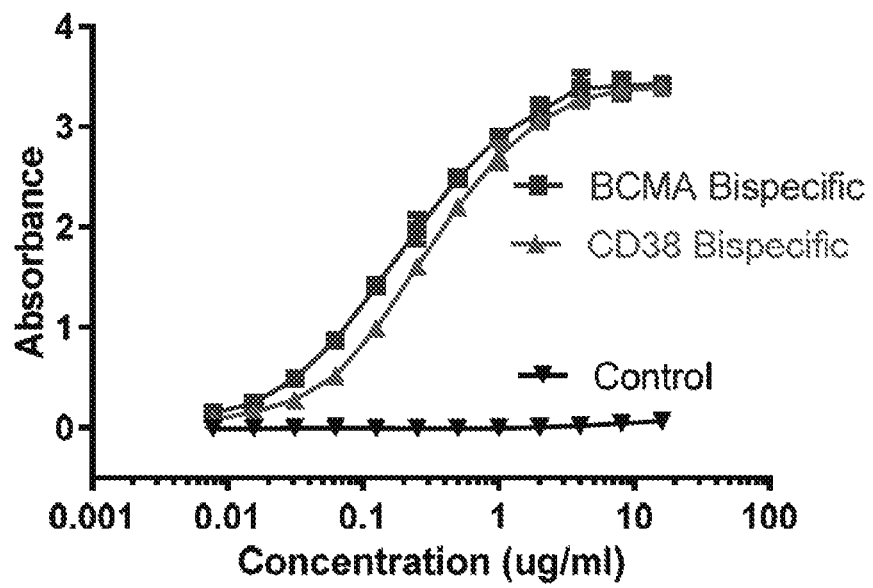
Figure 10B:
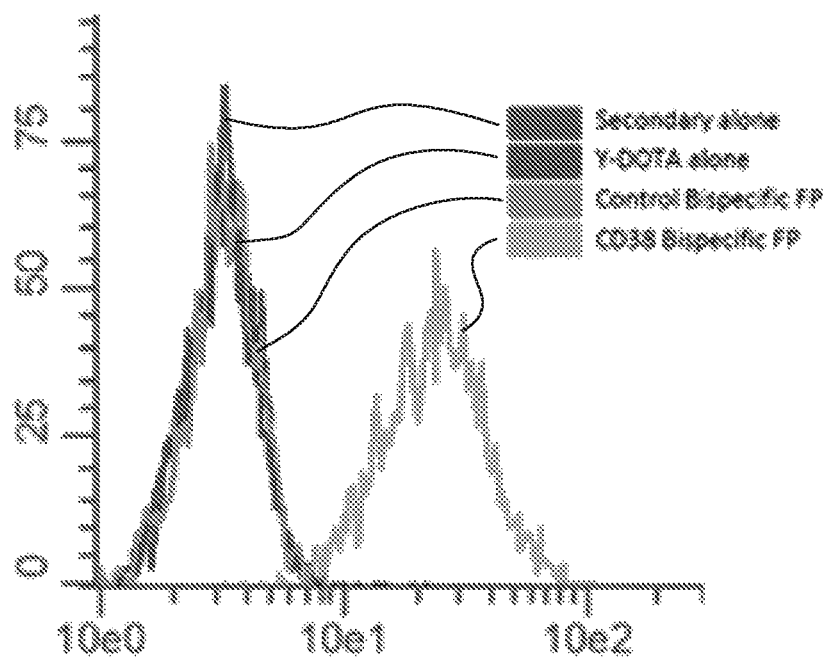
Figure 10C:
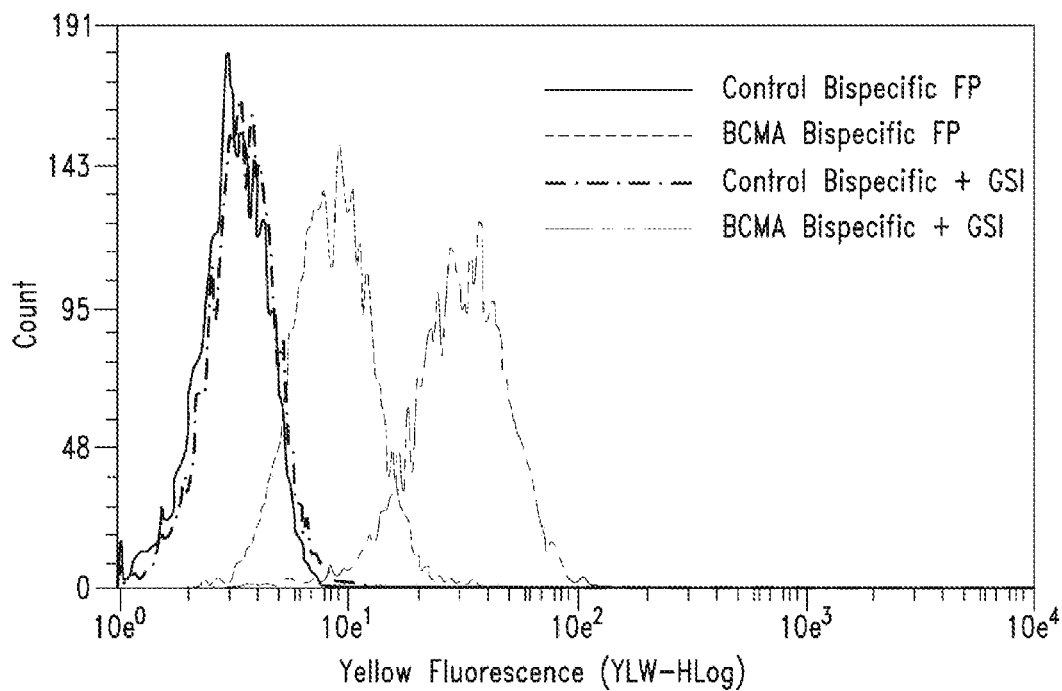

H929 cells ($0.5 \times 10^6$ each) were incubated in 100 µl of HBSS buffer containing 2% FBS and treated with 1.8 µg of the bispecific FP for 30 min at 4° C. After washing, the cells were mixed with 2 µl of PE-anti-human Fc antibody in 40 µl of HBSS-2% FBS buffer for 30 min at 4° C. Washed, resuspended and analyzed on a Guava® cytometer (FIGS. 10B and 10C). $^{90}$Y-DOTA capture by C825 binding domain was demonstrated using a sandwich ELISA assay in which a 96-well plate was coated with 70 µl of the BSA-Y-DOTA conjugate (1 µg/mL in PBS) and then blocked with 200 µl of 2% BSA in PBS buffer. After washing, the wells were treated with 100 µl of fusion proteins at a concentration of 16 µg/mL followed by serial dilution as indicated. The plate was further treated with HRP-anti-human Fc antibody followed by TMB. A control fusion protein shows no binding to Y-DOTA (FIG. 10A).

Therapy Studies

Figure 10D:
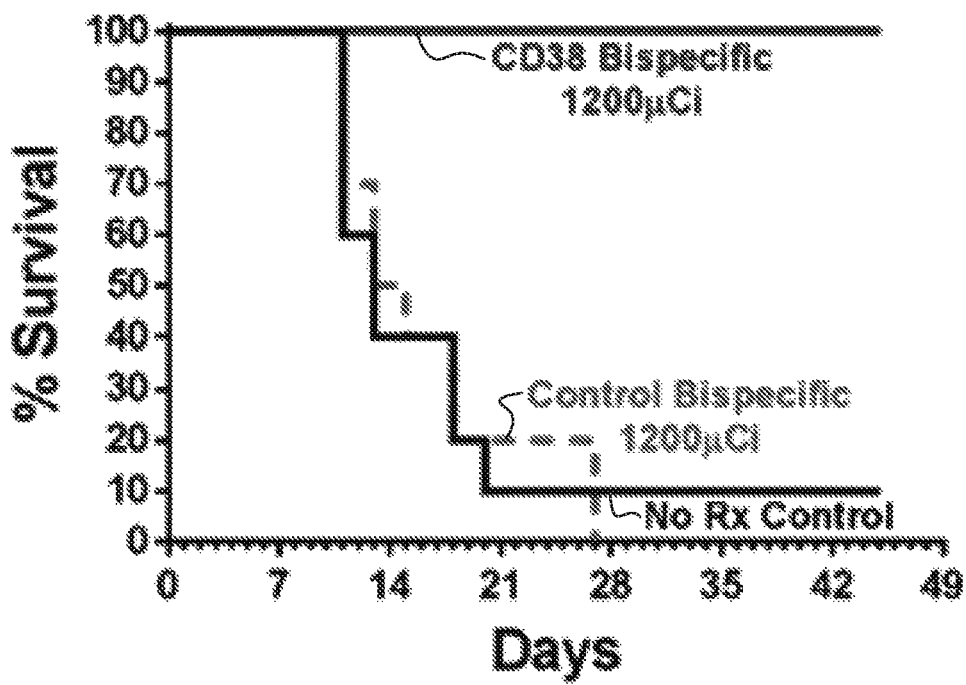

We have assessed the therapeutic efficacy of $^{90}$Y-PRIT using bispecific PRIT methods, groups of 10 mice bearing flank H929 MM xenograft tumors received 2.8 nmol of 028-Fc-C825 or the nonbinding, negative control 2H7-FC-C825 followed by 5 µg DYD 23 hours later. A single dose of 1.2 nmol of DOTA-biotin labeled with 1200 µCi $^{90}$Y was administered 1 hour after the CA. Mice were assessed every 2 days for tumor volume measurements, weight changes, and general appearance. Mice were euthanized if xenografts exceeded 1200 mm$^3$, caused obvious discomfort or impaired ambulation, or if mice lost more than 30% of their baseline body weight. The treatment was very well tolerated and the efficacy of the bispecific approach is evident (FIG. 10D).

Figure 11A:
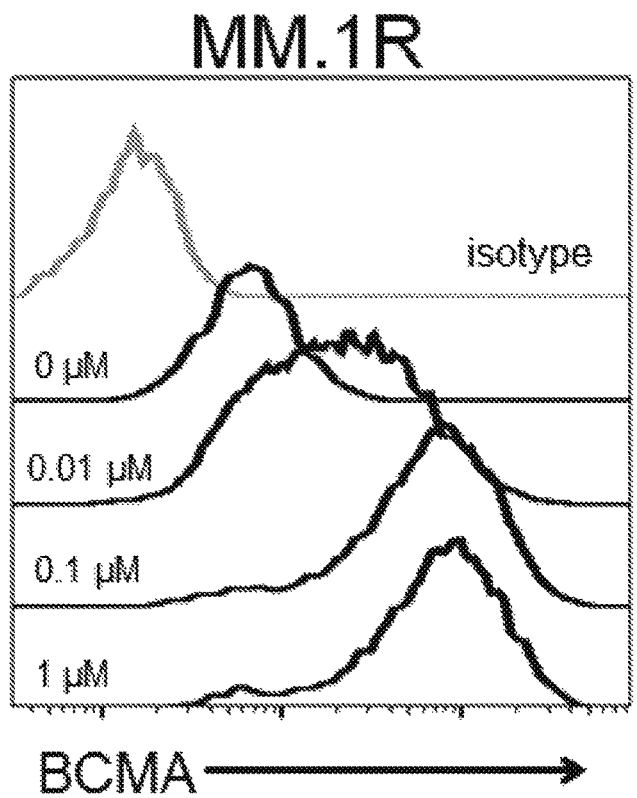
Figure 11B:
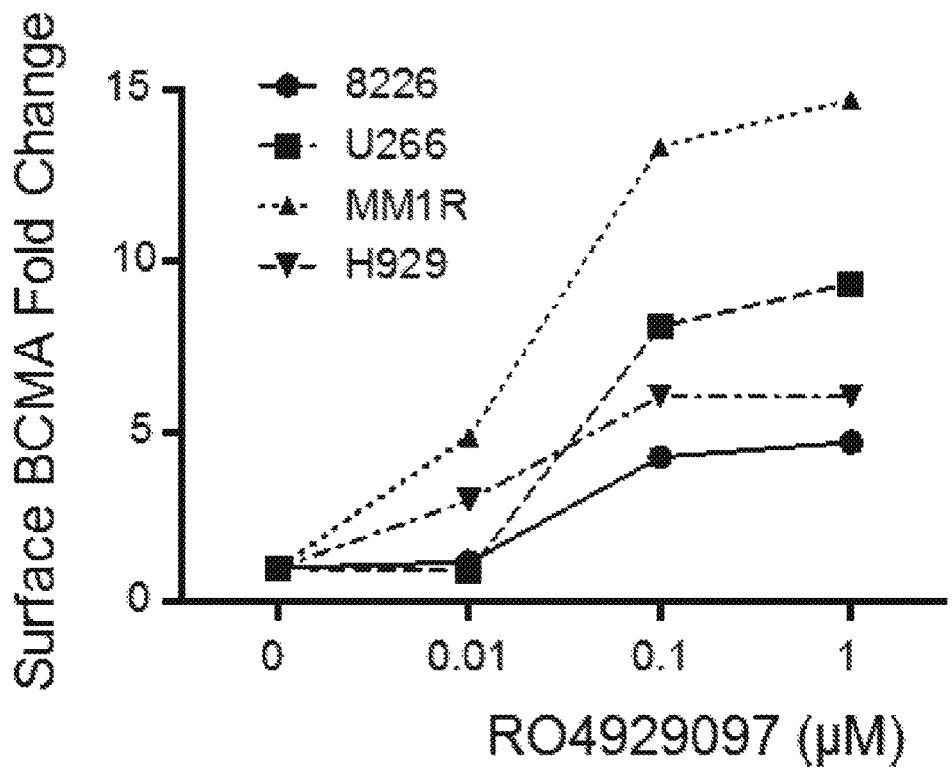
Figure 11C:
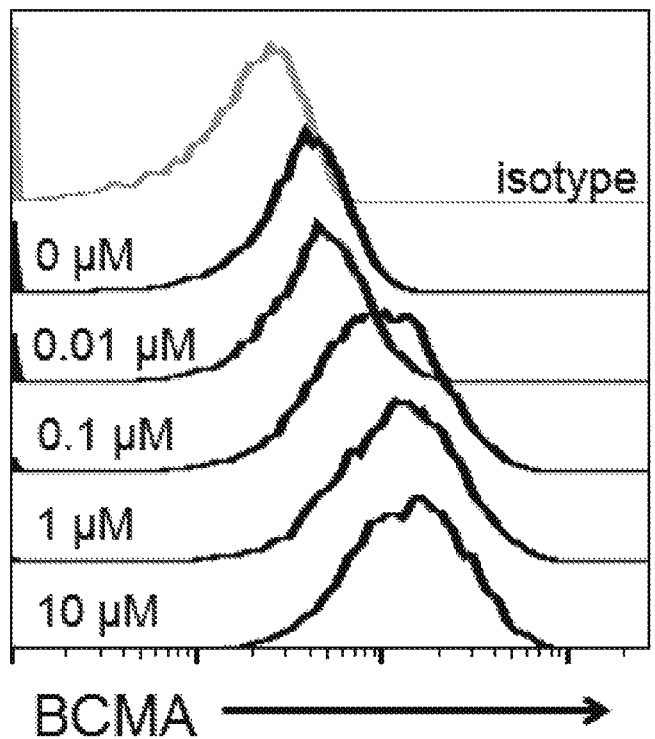
Figure 11D:
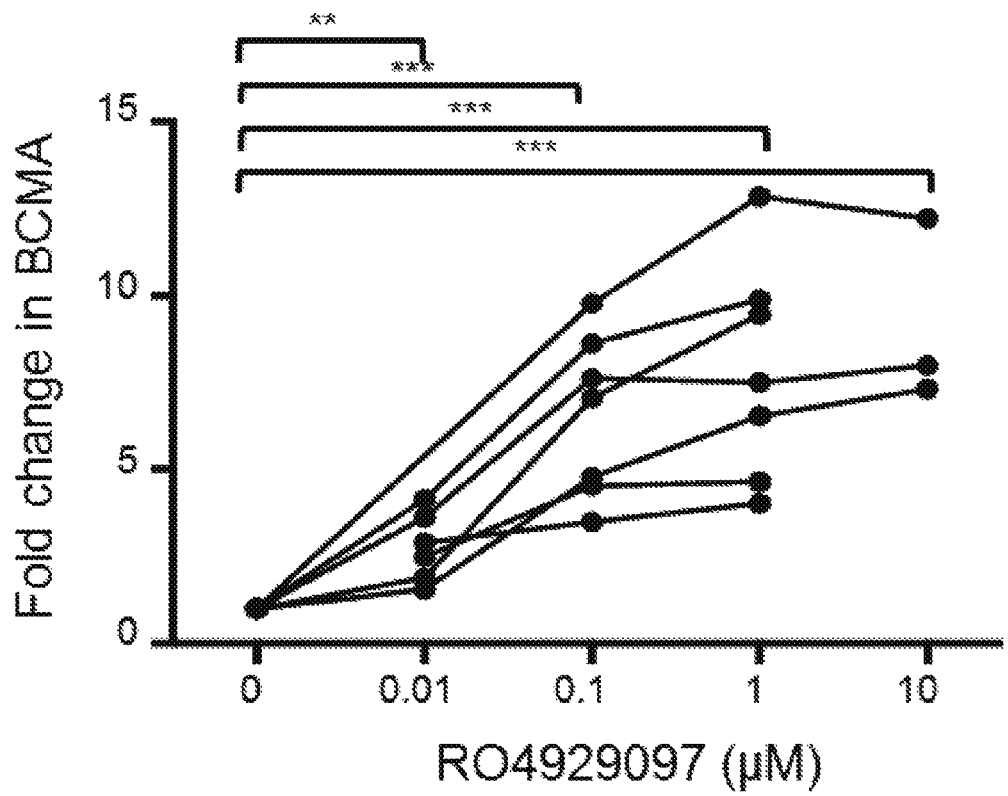

Gamma Secretase Inhibitors (GSI) upregulate BCMA expression on malignant plasma cells The effect of GSI on BCMA expression was evaluated by incubating four MM cell lines (RPMI8226, U266B1, MM1.R, and H929) and primary MM samples in media containing 0 (DMSO), 0.01, 0.1, and 1.0 µM of GSI and measuring surface BCMA at 5 hr. Exposure to the drug at these concentrations did not affect cell viability and we observed a marked increase in the MFI of BCMA staining maximal at the 1.0 µM concentration in all 4 cell lines (FIGS. 11A and 11B) and in primary MM cells (FIGS. 11C and 11D). These concentrations are 3-30 fold below the serum levels that are achieved by well tolerated oral dosing regimens of GSI in phase 1 trials in cancer patients. A time course revealed upregulation of BCMA occurred within 1 hr of GSI exposure with the peak MFI of BCMA staining at 5 to 24 hrs. Consistent with the upregulation of surface BCMA, we also observed a decline in soluble BCMA levels at 0.1 and 1.0 µM of GIS.

Methods and Strategies for Additional Studies

Biodistribution Studies

Groups of 3-5 mice with similar-sized tumors receive 2.8 nmol of C11-Fc-C825 or 2H7-Fc-C825 (isotype control) reagents. Twenty-three hours later, mice receive 5 µg of DYD CA, followed 1 hour later by 1.2 nmol DOTA-biotin labeled with 20 to 40 µCi (0.74-1.48 MBq) of $^{90}$Y. Blood samples, tumors, and body organs are obtained and $^{90}$Y activity are measured using a calibrated system and demonstrate the specificity of the approach.

In Vivo Targeting of MM Xenografts

Biodistribution studies are conducted in xenografted mice to compare the BCMA bispecific construct with CD38 bispecific PRIT. Mice are injected IV with saline, anti-CD38 bispecific FPs, or control bispecific reagents. After 20 h, clearing agent (CA) is administered at optimal doses for each construct (Table 1), followed 2 h later by the appropriate radiolabeled metal chelate (e.g., $^{90}$Y-DOTA or $^{90}$Y-DOTA-biotin). A DOTAY-Dextran clearing agent is used instead (Orcutt KD, et al., *Molecular cancer therapeutics.* 2012; 11(6):1365-1372, incorporated herein by reference in its entirety). First-step reagents are trace-labeled with 125I to assess their content in tumors and organs independent of the 90Y-chelate using a double label method (Pressman D. *Radiolabeled antibodies.* Ann NY Acad Sci. 1957; 69:644-650, incorporated herein by reference in its entirety). Groups of 5 mice each are bled from the retro-orbital venous plexus 1, 4, 24, 48, and 120 h after $^{90}$Y-ligand administration, euthanized, and tumors and normal organs excised, weighed, and y counted for 125I and $^{90}$Y (correcting for $^{90}$Y crossover into the 125I channel). Each experiment is optimally performed at least 3 times (using H929, L363 and RPMI 8226).

Pharmacokinetics

PK data are analyzed and best-fit curves plotted using Win-NonLin (Pharsight) to determine serum $t_{1/2}$, volume of distribution, blood clearance, etc. The modeling capabilities of Win-NonLin guide decisions to modulate reagent doses and time intervals, if deemed advisable.

Radiation Dosimetry

Absorbed doses to organs and tumors are estimated for 400, 800, and 1200 µCi of administered $^{90}$Y activity are calculated for each preselected organ or tissue and time-activity curves are constructed for serially sacrificed mice to determine the total number of nuclear transformations to infinity (proportional to the area under the biodistribution curves). (Fisher DR, et al. Energy Distribution and the Relative Biological Effects of Internal Alpha Emitters. *Rad Prot Dosimetry.* 1985; 13:223-227; Humm J L, et al. Internal dosimetry using data derived from autoradiographs. *Journal of nuclear medicine.* 1993; 34(10):1811-1817; Sgouros G, et al. MIRD Pamphlet No. 22 (abridged): radiobiology and dosimetry of alphaparticle emitters for targeted radionuclide therapy. *J Nucl Med.* 2010; 51(2):311-328; Sgouros G, et al. Modelling and dosimetry for alpha-particle therapy. *Current radiopharmaceuticals.* 2011; 4(3):261-265; each of which is incorporated herein by reference in its entirety). The mathematical approach β-emitter dosimetry in animal tissues is well established. Fisher DR, et al. *Rad Prot Dosimetry.* 1985; 13:223-227; Fisher D R and Harty R. The microdosimetry of lymphocytes irradiated by alpha-particles. *Int J Radiat Biol Relat Stud Phys Chem Med.* 1982; 41(3):315-324; Fisher D R. The Microdosimetry of Monoclonal Antibodies Labeled with Alpha Emitters. Oak Ridge, Tennessee: Oak Ridge Associated Universities; 1986; each of which is incorporated herein by reference in its entirety), β-particle or γ-ray Monte Carlo dosimetry [MCNP]) is used to calculate the dose to specific target tissues (Fisher DRaX-MCT. MCNP—A general Monte Carlo N-particle transport code, version 5, volume I: overview and theory LA-UR-03-1987. Los Alamos, New Mexico: Los Alamos National Laboratory; 2005; incorporated herein by reference in its entirety).

Therapy Experiments

Therapy experiments can use the bispecific constructs followed by 400, 800, or 1200 μCi of $^{90}$Y-labeled ligand in groups of 10 xenograft-bearing mice (Table 1). At least 3 experiments are conducted with different myeloma cell lines. Because some investigators criticize subcutaneous xenograft MM tumors in athymic mouse models, disseminated MM tumors in a NRG mouse model can also be addressed.

TABLE 1

Groups for Biodistribution and Therapy Experiments with Bispecific Antibodies (see FIG. 1 for construct)

| Group | 1st step (1.4, 2.8 nmol) | Clearing Agent | 2nd step Radiolabeled Ligand (1-2 nmol) | Times of eval.* |
|---|---|---|---|---|
| 1 | none (control) | NONE | $^{90}$Y-DOTA or $^{90}$Y-DOTA-biotin | 1, 4, 24, 48, 120 h |
| 2 | $^{125}$I-Control Bispecific × C825 | DOTAY-Dextran | $^{90}$Y-DOTA | 1, 4, 24, 48, 120 h |
| 3 | $^{125}$I-Anti-BCMA × C825 (bispecific BCMA)-construct in FIG. 1 | DOTAY-Dextran | $^{90}$Y-DOTA | 1, 4, 24, 48, 120 h |
| 4 | Anti-CD38 × C825 (bispecific CD38)** | DOTAY-Dextran | $^{90}$Y-DOTA | N/A |

*Biodistribution studies
**Therapy studies only

Discussion

The restricted nature of BCMA expression in MM is a theoretical advantage for commercial translation. BCMA targeting is also being explored as a target in B cell malignancies. If those findings remain promising, the results could extend potential application of our approach to patients with non-Hodgkin lymphoma (NHL). A broader role for CD38 bispecific PRIT is also feasible and we have already demonstrated efficacy using this agent in preclinical models of NHL. As in MM, treatment-refractory NHL typically retains sensitivity to radiation, making CD38 PRIT a potentially effective treatment for such patients as well. Beyond tumors that share a common B-cell lineage, CD38 is expressed in most natural killer (NK)/T-cell lymphomas, where 50% of patients die within 5 years 55 and overexpression of CD38 predicts poor outcomes for NK/T-cell lymphoma patients, presenting another potential translational application for CD38 PRIT. Despite impressive efficacy and safety profiles that led to FDA approval of two radioimmunoconjuages for the treatment of B cell lymphoma ($^{131}$I-tositumomab and $^{90}$y-ibritumumab tiuxitan), these agents have rarely been incorporated into clinical care. RIT targeting CD20 remains in the National Comprehensive Cancer Network Guidelines (NCCN) as a first-line therapy for elderly or infirm patients with follicular lymphoma and as a recommended approach to consolidation or second-line therapy for follicular NHL. Nonetheless, overall utilization remains low and RIT is administered disproportionately within the confines of academic centers. Limited use is likely a consequence of multiple factors which include the availability and ease of administration associated with other novel targeting agents and concerns about radiation toxicity, particularly to the bone marrow. Concerns regarding reimbursement to community oncologists cannot be trivialized, however the absolute cost of RIT for consolidation is lower than the cost of maintenance rituximab ($46,000; and $54,000 to $72,000 [12-16 courses]) respectively. RIT may also offer a quality of life advantage to patients because administration involves a single patient infusion visit as compared to frequent infusions during rituximab maintenance.

Innovations that improve targeting, diminish toxicity and highlight the unique favorable attributes associated with RIT will help to overcome a history of limited adoption. We have demonstrated that bispecific antibodies targeting CD38 on myeloma cells work as well as the CD20 antibodies published in Cancer Research and that BCMA is a viable alternative target for the bispecific PRIT approach. Ultimately, superior efficacy provides the most compelling argument for the adoption of PRIT.

While illustrative embodiments have been illustrated and described, it will be appreciated that various changes can be made therein without departing from the spirit and scope of the invention.

The embodiments of the invention in which an exclusive property or privilege is claimed are defined as follows:

1. A bispecific affinity reagent, comprising:
   a first binding domain that binds to a CD38 antigen or a B cell maturation antigen (BCMA), wherein the first binding domain that binds to the CD38 antigen comprises an amino acid sequence included in an amino acid sequence of the bispecific affinity reagent as set forth in any one of SEQ ID NOs: 2, 4, or 6, and wherein the first binding domain that binds the BCMA comprises an amino acid sequence included in an amino acid sequence of the bispecific affinity reagent as set forth in any one of SEQ ID NOs: 8 or 10; and
   a second binding domain that binds to a yttrium-DOTA (Y-DOTA) ligand, wherein the second binding domain that binds to the Y-DOTA ligand comprises an amino acid sequence as set forth in any one of SEQ ID NOs: 20-36.

2. The bispecific affinity reagent of claim 1, wherein the affinity reagent is a fusion protein and the first binding domain and the second binding domain are separated by a hinge region.

3. A method of treating a hematological malignancy expressing a CD38 antigen and/or a BCMA in a subject, the method comprising:
   administering to the subject a therapeutically effective amount of the bispecific affinity reagent of claim 1, and thereafter;
   administering to the subject a therapeutically effective amount of the Y-DOTA ligand.

4. The method of claim 3, further comprising administering an effective amount of a clearing agent (CA) after administering the bispecific affinity reagent and before administering the Y-DOTA ligand.

5. The method of claim 3, further comprising administering to the subject an amount of a gamma secretase inhibitor (GSI) sufficient to upregulate expression of BCMA in the malignant cells.

6. A method of treating a hematological malignancy expressing a CD38 antigen and/or a B cell maturation antigen (BCMA) in a subject, the method comprising:
   administering to the subject a therapeutically effective amount of a first bispecific affinity reagent, wherein the first bispecific affinity reagent comprises a first binding domain that binds to a CD38 antigen, and wherein the first binding domain comprises an amino acid sequence included in an amino acid sequence of the bispecific affinity reagent as set forth in any one of SEQ ID NOs: 2, 4, or 6, and a second binding domain that binds to a yttrium-DOTA (Y-DOTA) ligand, wherein the second binding domain that binds to the Y-DOTA ligand comprises an amino acid sequence as set forth in any one of SEQ ID NOs: 20-36;

administering to the subject a therapeutically effective amount of a second bispecific affinity reagent, wherein the second bispecific affinity reagent comprises a first binding domain that binds to the BCMA, and wherein the second binding domain comprises an amino acid sequence as set forth in any one of SEQ ID NOs: 8 or 10, and a second binding domain that binds to a Y-DOTA ligand, wherein the second binding domain that binds to the Y-DOTA ligand comprises an amino acid sequence as set forth in any one of SEQ ID NOs: 20-36 and thereafter; and administering to the subject a therapeutically effective amount of the Y-DOTA ligand.

7. The method of claim 6, further comprising administering an effective amount of a clearing agent (CA) after administering the bispecific affinity reagent and before administering the Y-DOTA ligand.

* * * * *

SEQUENCE LISTING

```
<160> NUMBER OF SEQ ID NOS: 139

<210> SEQ ID NO 1
<211> LENGTH: 2343
<212> TYPE: DNA
<213> ORGANISM: Artificial sequence
<220> FEATURE:
<223> OTHER INFORMATION: Synthetic

<400> SEQUENCE: 1
aagcttgccg ccatggattt tcaagtgcag attttcagct tcctgctaat cagtgcttca      60
gtcataatgt ccagaggaga catccagatg acccagtctc catcctcact gtctgcatct     120
gtaggagaca gagtcaccat cacttgtcgg gcgagtcagg gtattcgcag ctggttagcc     180
```

```
tggtatcagc agaaaccaga gaaagcccct aagtccctga tctatgctgc atccagtttg    240
caaagtgggg tcccatcaag gttcagcggc agtggatctg ggacagattt cactctcacc    300
atcagcagcc tgcagcctga agattttgca acttattact gccaacagta taatagttac    360
ccgctcactt tcggcggagg gaccaaggtg gagatcaaga tctctggtgg cggtggctcg    420
ggcggtggtg ggtcgggtgg cggtggctcg ggcggtggtg ggtcgggcgg cggcggttcg    480
agccaggtcc aactggtgca gtctggggct gaggtgaaga agcctgggtc ctcggtgaag    540
gtctcctgca aggcttttgg aggcaccttc agcagctacg ctatcagctg ggtgcgacag    600
gcccctggac aagggcttga gtggatggga aggatcatcc gtttccttgg tatagcaaac    660
tacgcacaga gttccaggg cagagtcacg cttatcgcgg acaaatccac gaacacagcc    720
tacatggagc tgagcagcct gagatctgag gacacggccg tttattactg tgcgggggaa    780
cctggggagc gggaccccga tgctgttgat atctgggggcc aagggacaat ggtcaccgtc    840
tcttcactcg agcccaaatc ttctgacaaa actcacacat gtccaccgtg cccagcacct    900
gaactcctgg gggaccgtc agtcttcctc ttccccccaa acccaagga caccctcatg    960 atctcccgga cccctgaggt cacatgcgtg gtggtggacg tgagccacga agaccctgag   1020
gtcaagttca actggtacgt ggacggcgtg gaggtgcata atgccaagac aaagccgcgg   1080
gaggagcagt acaacagcac gtaccgtgtg gtcagcgtcc tcaccgtcct gcaccaggac   1140
tggctgaatg gcaaggagta caagtgcaag gtctccaaca agccctccc agccccatc    1200 gagaaaacca tctccaaagc caagggcag ccccgagaac cacaggtgta caccctgccc   1260
ccatcccggg atgagctgac caagaaccag gtcagcctga cctgcctggt caaaggcttc   1320
tatcccagcg acatcgccgt ggagtgggag agcaatgggc agccggagaa caactacaag   1380
accacgcctc ccgtgctgga ctccgacggc tccttcttcc tctacagcaa gctcaccgtg   1440
gacaagagca ggtggcagca ggggaacgtc ttctcatgct ccgtgatgca tgagggtctg   1500
cacaaccact acacgcagaa gagcctctct ctgtctccgg gtaaagtcga cggtgctagc   1560
agccatgtga atgtgagcag ccctagcgtg caggatatcc acgttaagtt gcaagaatct   1620
ggtccaggtt tggttcagcc atctcaatct ttgtctctta cttgtactgt ttctggttc   1680 tcttttgactg attatggtgt tcattgggtt agacaatctc caggtaaagg tttggaatgg   1740
ttgggtgtta tttggtctgg tggaggtact gcttataata ctgctttgat ttctaggttg   1800
aatatttatc gagataattc taaaaatcaa gttttttcttg aaatgaattc tttgcaagct   1860
gaagatactg ctatgtatta ttgtgctaga agaggttctt atccatataa ttatttttgat   1920 gcttggggtt gtggtactac tgttactgtt tcttctggag gcggcggatc tggcggtgga   1980
ggttctggcg gcggcggatc tcaagctgtt gttattcaag aatctgcttt gactactcct   2040
ccaggtgaaa ccgttacttt gacttgtgga tcttctactg gtgctgttac tgcttctaat   2100
tatgctaatt gggttcaaga aaaaccagat cattgcttta ctggtttgat tggtggtcat   2160
aataatagac caccaggtgt tccggctaga ttttctggtt ctttgattgg tgataaagct   2220
gctttgacta ttgctggtac tcaaactgaa gatgaagcta tttatttttg tgctttgtgg   2280
tattctgatc attgggttat tggtggtggt actagattga ctgtttttggg ctaataatct   2340 aga                                                                 2343
```

<210> SEQ ID NO 2
<211> LENGTH: 751
<212> TYPE: PRT

<213> ORGANISM: Artificial sequence
<220> FEATURE:
<223> OTHER INFORMATION: Synthetic

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Ile Ser Gly Gly Gly
            100                 105                 110

Gly Ser Gly Gly Gly Gly Ser Gly Gly Gly Ser Gly Gly Gly Gly
        115                 120                 125

Ser Gly Gly Gly Gly Ser Ser Gln Val Gln Leu Val Gln Ser Gly Ala
    130                 135                 140

Glu Val Lys Lys Pro Gly Ser Ser Val Lys Val Ser Cys Lys Ala Phe
145                 150                 155                 160

Gly Gly Thr Phe Ser Ser Tyr Ala Ile Ser Trp Val Arg Gln Ala Pro
                165                 170                 175

Gly Gln Gly Leu Glu Trp Met Gly Arg Ile Ile Arg Phe Leu Gly Ile
            180                 185                 190

Ala Asn Tyr Ala Gln Lys Phe Gln Gly Arg Val Thr Leu Ile Ala Asp
        195                 200                 205

Lys Ser Thr Asn Thr Ala Tyr Met Glu Leu Ser Ser Leu Arg Ser Glu
    210                 215                 220

Asp Thr Ala Val Tyr Tyr Cys Ala Gly Glu Pro Gly Glu Arg Asp Pro
225                 230                 235                 240

Asp Ala Val Asp Ile Trp Gly Gln Gly Thr Met Val Thr Val Ser Ser
                245                 250                 255

Leu Glu Pro Lys Ser Ser Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu

```
                385                 390                 395                 400
        Thr Lys Asn Gln Val Ser Leu Thr Cys Leu Val Lys Gly Phe Tyr Pro
                        405                 410                 415

Ser Asp Ile Ala Val Glu Trp Glu Ser Asn Gly Gln Pro Glu Asn Asn
                        420                 425                 430

Tyr Lys Thr Thr Pro Pro Val Leu Asp Ser Asp Gly Ser Phe Phe Leu
                        435                 440                 445

Tyr Ser Lys Leu Thr Val Asp Lys Ser Arg Trp Gln Gln Gly Asn Val
                    450                 455                 460

Phe Ser Cys Ser Val Met His Glu Gly Leu His Asn His Tyr Thr Gln
        465                 470                 475                 480

Lys Ser Leu Ser Leu Ser Pro Gly Lys Val Asp Gly Ala Ser Ser His
                        485                 490                 495

Val Asn Val Ser Ser Pro Ser Val Gln Asp Ile His Val Lys Leu Gln
                        500                 505                 510

Glu Ser Gly Pro Gly Leu Val Gln Pro Ser Gln Ser Leu Ser Leu Thr
                        515                 520                 525

Cys Thr Val Ser Gly Phe Ser Leu Thr Asp Tyr Gly Val His Trp Val
                        530                 535                 540

Arg Gln Ser Pro Gly Lys Gly Leu Glu Trp Leu Gly Val Ile Trp Ser
        545                 550                 555                 560

Gly Gly Gly Thr Ala Tyr Asn Thr Ala Leu Ile Ser Arg Leu Asn Ile
                        565                 570                 575

Tyr Arg Asp Asn Ser Lys Asn Gln Val Phe Leu Glu Met Asn Ser Leu
                        580                 585                 590

Gln Ala Glu Asp Thr Ala Met Tyr Tyr Cys Ala Arg Arg Gly Ser Tyr
                        595                 600                 605

Pro Tyr Asn Tyr Phe Asp Ala Trp Gly Cys Gly Thr Thr Val Thr Val
                        610                 615                 620

Ser Ser Gly Gly Gly Gly Ser Gly Gly Gly Gly Ser Gly Gly Gly Gly
        625                 630                 635                 640

Ser Gln Ala Val Val Ile Gln Glu Ser Ala Leu Thr Thr Pro Pro Gly
                        645                 650                 655

Glu Thr Val Thr Leu Thr Cys Gly Ser Ser Thr Gly Ala Val Thr Ala
                        660                 665                 670

Ser Asn Tyr Ala Asn Trp Val Gln Glu Lys Pro Asp His Cys Phe Thr
                        675                 680                 685

Gly Leu Ile Gly Gly His Asn Asn Arg Pro Pro Gly Val Pro Ala Arg
                        690                 695                 700

Phe Ser Gly Ser Leu Ile Gly Asp Lys Ala Ala Leu Thr Ile Ala Gly
        705                 710                 715                 720

Thr Gln Thr Glu Asp Glu Ala Ile Tyr Phe Cys Ala Leu Trp Tyr Ser
                        725                 730                 735

Asp His Trp Val Ile Gly Gly Thr Arg Leu Thr Val Leu Gly
                        740                 745                 750

<210> SEQ ID NO 3
<211> LENGTH: 2346
<212> TYPE: DNA
<213> ORGANISM: Artificial sequence
<220> FEATURE:
<223> OTHER INFORMATION: Synthetic

<400> SEQUENCE: 3
aagcttgccg ccatggactt ccaggtgcag atcttctcct tcctgctgat ctccgcctcc    60
```

```
gtgatcatgt ccaggggcga gatcgtgctg acccagtccc ccgccaccct gtccctgtcc    120
cccggcgaga gggccaccct gtcctgcagg gcctcccagt ccgtgtcctc ctacctggcc    180
tggtaccagc agaagcccgg ccagcccccc aggctgctga tctacgacgc ctccaacagg    240
gccaccggca tccccgccag gttctccggc tccggctccg gcaccgactt caccctgacc    300
atctcctccc tggagcccga ggacttcgcc gtgtactact gccagcagag gtccaactgg    360
ccccccacct tcggccaggg caccaaggtg gagatcaaga tctccggcgg cggcggctcc    420
ggcggcggcg gaagcggagg aggaggaagc ggcggcggcg gctccggcgg cggcggctcc    480
tccgaggtgc agctgctgga gtccggcggc ggcctggtgc agcccggcgg ctccctgagg    540
ctgtcctgcg ccgtgtccgg cttcaccttc aactccttcg ccatgtcctg ggtgaggcag    600
gcccccggca agggcctgga gtgggtgtcc gccatctccg gctccggcgg cggcacctac    660
tacgccgact ccgtgaaggg caggttcacc atctccaggg acaactccaa gaacaccctg    720
tacctgcaga tgaactccct gagggccgag gacaccgccg tgtacttctg cgccaaggac    780
aagatcctgt ggttcggcga gcccgtgttc gactactggg gccagggcac cctggtgacc    840
gtgtcctccc tcgagcccaa atcttctgac aaaactcaca catgtccacc gtgcccagca    900
cctgaactcc tggggggacc gtcagtcttc ctcttccccc caaaacccaa ggacaccctc    960
atgatctccc ggacccctga ggtcacatgc gtggtggtgg acgtgagcca cgaagaccct    1020
gaggtcaagt tcaactggta cgtggacggc gtggaggtgc ataatgccaa gacaaagccg    1080
cgggaggagc agtacaacag cacgtaccgt gtggtcagcg tcctcaccgt cctgcaccag    1140
gactggctga atggcaagga gtacaagtgc aaggtctcca acaaagccct cccagccccc    1200
atcgagaaaa ccatctccaa agccaaaggg cagccccgag aaccacaggt gtacaccctg    1260
cccccatccc gggatgagct gaccaagaac caggtcagcc tgacctgcct ggtcaaaggc    1320
ttctatccca gcgacatcgc cgtggagtgg gagagcaatg ggcagccgga gaacaactac    1380
aagaccacgc ctcccgtgct ggactccgac ggctccttct tcctctacag caagctcacc    1440
gtggacaaga gcaggtggca gcaggggaac gtcttctcat gctccgtgat gcatgagggt    1500
ctgcacaacc actacacgca gaagagcctc tctctgtctc cgggtaaagt cgacggtgct    1560
agcagccatg tgaatgtgag cagccctagc gtgcaggata tccacgttaa gttgcaagaa    1620
tctggtccag gtttggttca gccatctcaa tctttgtctc ttacttgtac tgtttctggt    1680
ttctctttga ctgattatgg tgttcattgg gttagacaat ctccaggtaa aggtttggaa    1740
tggttgggtg ttatttggtc tggtggaggt actgcttata atactgcttt gatttctagg    1800
ttgaatattt atcgagataa ttctaaaaat caagtttttc ttgaaatgaa ttctttgcaa    1860
gctgaagata ctgctatgta ttattgtgct agaagaggtt cttatccata taattatttt    1920
gatgcttggg gttgtggtac tactgttact gtttcttctg aggcggcgg atctggcggt    1980 ggaggttctg gcgcggcgg atctcaagct gttgttattc aagaatctgc tttgactact    2040
cctccaggtg aaaccgttac tttgacttgt ggatcttcta ctggtgctgt tactgcttct    2100
aattatgcta attgggttca agaaaaacca gatcattgct ttactggttt gattggtggt    2160
cataataata gaccaccagg tgttccggct agatttctg gttctttgat tggtgataaa    2220
gctgctttga ctattgctgg tactcaaact gaagatgaag ctatttattt ttgtgctttg    2280
tggtattctg atcattgggt tattggtggt ggtactagat tgactgtttt gggctaataa    2340
tctaga                                                              2346
```

<210> SEQ ID NO 4
<211> LENGTH: 752
<212> TYPE: PRT
<213> ORGANISM: Artificial sequence
<220> FEATURE:
<223> OTHER INFORMATION: Synthetic

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Ile Ser Gly Gly Gly
            100                 105                 110

Gly Ser Gly Gly Gly Gly Ser Gly Gly Gly Ser Gly Gly Gly
        115                 120                 125

Ser Gly Gly Gly Gly Ser Ser Glu Val Gln Leu Leu Glu Ser Gly Gly
130                 135                 140

Gly Leu Val Gln Pro Gly Gly Ser Leu Arg Leu Ser Cys Ala Val Ser
145                 150                 155                 160

Gly Phe Thr Phe Asn Ser Phe Ala Met Ser Trp Val Arg Gln Ala Pro
                165                 170                 175

Gly Lys Gly Leu Glu Trp Val Ser Ala Ile Ser Gly Ser Gly Gly Gly
            180                 185                 190

Thr Tyr Tyr Ala Asp Ser Val Lys Gly Arg Phe Thr Ile Ser Arg Asp
        195                 200                 205

Asn Ser Lys Asn Thr Leu Tyr Leu Gln Met Asn Ser Leu Arg Ala Glu
210                 215                 220

Asp Thr Ala Val Tyr Phe Cys Ala Lys Asp Lys Ile Leu Trp Phe Gly
225                 230                 235                 240

Glu Pro Val Phe Asp Tyr Trp Gly Gln Gly Thr Leu Val Thr Val Ser
                245                 250                 255

Ser Leu Glu Pro Lys Ser Ser Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365
```

```
Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
450                 455                 460

Val Phe Ser Cys Ser Val Met His Glu Gly Leu His Asn His Tyr Thr
465                 470                 475                 480

Gln Lys Ser Leu Ser Leu Ser Pro Gly Lys Val Asp Gly Ala Ser Ser
                485                 490                 495

His Val Asn Val Ser Ser Pro Ser Val Gln Asp Ile His Val Lys Leu
            500                 505                 510

Gln Glu Ser Gly Pro Gly Leu Val Gln Pro Ser Gln Ser Leu Ser Leu
        515                 520                 525

Thr Cys Thr Val Ser Gly Phe Ser Leu Thr Asp Tyr Gly Val His Trp
    530                 535                 540

Val Arg Gln Ser Pro Gly Lys Gly Leu Glu Trp Leu Gly Val Ile Trp
545                 550                 555                 560

Ser Gly Gly Gly Thr Ala Tyr Asn Thr Ala Leu Ile Ser Arg Leu Asn
                565                 570                 575

Ile Tyr Arg Asp Asn Ser Lys Asn Gln Val Phe Leu Glu Met Asn Ser
            580                 585                 590

Leu Gln Ala Glu Asp Thr Ala Met Tyr Tyr Cys Ala Arg Arg Gly Ser
        595                 600                 605

Tyr Pro Tyr Asn Tyr Phe Asp Ala Trp Gly Cys Gly Thr Thr Val Thr
    610                 615                 620

Val Ser Ser Gly Gly Gly Gly Ser Gly Gly Gly Gly Ser Gly Gly Gly
625                 630                 635                 640

Gly Ser Gln Ala Val Val Ile Gln Glu Ser Ala Leu Thr Thr Pro Pro
                645                 650                 655

Gly Glu Thr Val Thr Leu Thr Cys Gly Ser Ser Thr Gly Ala Val Thr
            660                 665                 670

Ala Ser Asn Tyr Ala Asn Trp Val Gln Glu Lys Pro Asp His Cys Phe
        675                 680                 685

Thr Gly Leu Ile Gly Gly His Asn Asn Arg Pro Pro Gly Val Pro Ala
    690                 695                 700

Arg Phe Ser Gly Ser Leu Ile Gly Asp Lys Ala Ala Leu Thr Ile Ala
705                 710                 715                 720

Gly Thr Gln Thr Glu Asp Glu Ala Ile Tyr Phe Cys Ala Leu Trp Tyr
                725                 730                 735

Ser Asp His Trp Val Ile Gly Gly Thr Arg Leu Thr Val Leu Gly
            740                 745                 750
```

<210> SEQ ID NO 5
<211> LENGTH: 2322
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (798)..(798)
<223> OTHER INFORMATION: n is a, c, g, or t

<400> SEQUENCE: 5

```
aagcttgccg ccatggagac agacacactc ctgctatggg tgctgctgct ctgggttcca      60
ggttccacag gtgacatcgt gatgacccag tctccaaaaa tcatgcccac atcagtggga     120
gacagggtca gcgtcacctg caaggccagt caaaatgtgg atactaatgt agcctggtat     180
caacagaaac caggacagtc tcctaaagca ctgatttact cggcatccta ccgatacagt     240
ggagtccctg atcgcttcac aggcagtgga tctgggacag atttcactct caccatcacc     300
aatgtgcagt ctgaggactt ggcagagtat ttctgtcagc aatatgacag ctatcctctc     360
acgttcggtg ctgggaccaa gctggacctg aagatctctg gtggcggtgg ctcgggcggt     420
ggtgggtcgg gtggcggcgg ctcgggtggt ggtgggtcgg gcggcggcgg ctctagcgag     480
gtgaagctgc aggagtcagg acctagcctg gtgcagcctg aggatccct gaaactctcc      540
tgtgcagcct caggattcga ttttagtaga tcctggatga attgggtccg gcaggctcca     600
ggaaaagggc tagaatggat tggagaaatt aatccagata gcagtacgat aaactatacg     660
acatctctaa aggataaatt catcatctcc agagacaacg ccaaaaatac gctgtacctg     720
caaatgacca agtgagatc tgaggacaca gcccttatt actgtgcaag atatggtaac     780
tggtttcctt attggggnca agggactctg gtcactgtga gttctctcga gcccaaatct     840
tctgacaaaa ctcacacatg tccaccgtgc ccagcacctg aactcctggg gggaccgtca     900
gtcttcctct tccccccaaa acccaaggac accctcatga tctcccggac ccctgaggtc     960
acatgcgtgg tggtggacgt gagccacgaa gaccctgagg tcaagttcaa ctggtacgtg    1020
gacggcgtgg aggtgcataa tgccaagaca aagccgcggg aggagcagta caacagcacg    1080
taccgtgtgg tcagcgtcct caccgtcctg caccaggact ggctgaatgg caaggagtac    1140
aagtgcaagg tctccaacaa agccctccca gcccccatcg agaaaaccat ctccaaagcc    1200
aaagggcagc cccgagaacc acaggtgtac accctgcccc catcccggga tgagctgacc    1260
aagaaccagg tcagcctgac ctgcctggtc aaaggcttct atcccagcga catcgccgtg    1320
gagtgggaga gcaatgggca gccggagaac aactacaaga ccacgcctcc cgtgctggac    1380
tccgacggct ccttcttcct ctacagcaag ctcaccgtgg acaagagcag gtggcagcag    1440
gggaacgtct tctcatgctc cgtgatgcat gagggtctgc acaaccacta cacgcagaag    1500
agcctctctc tgtctccggg taaagtcgac ggtgctagca gccatgtgaa tgtgagcagc    1560
cctagcgtgc aggatatcca cgttaagttg caagaatctg gtccaggttt ggttcagcca    1620
tctcaatctt tgtctcttac ttgtactgtt tctggtttct ctttgactga ttatggtgtt    1680
cattgggtta gacaatctcc aggtaaaggt ttggaatggt tgggtgttat tggtctggt    1740
ggaggtactc cttataatac tgctttgatt tctaggttga atatttatcg agataattct    1800
aaaaatcaag ttttcttga aatgaattct ttgcaagctg aagatactgc tatgtattat    1860
tgtgctagaa gaggttctta tccatataat tatttgatg cttggggttg tggtactact    1920
gttactgttt cttctggagg cggcggatct ggcggtggag gttctggcgg cggcggatct    1980
caagctgttg ttattcaaga atctgctttg actactcctc caggtgaaac cgttactttg    2040
acttgtggat cttctactgg tgctgttact gcttctaatt atgctaattg ggttcaagaa    2100
aaaccagatc attgctttac tggtttgatt ggtggtcata ataatagacc accaggtgtt    2160
```

```
ccggctagat tttctggttc tttgattggt gataaagctg ctttgactat tgctggtact    2220
caaactgaag atgaagctat ttatttttgt gctttgtggt attctgatca ttgggttatt    2280
ggtggtggta ctagattgac tgttttgggc taataatcta ga                      2322
```

<210> SEQ ID NO 6
<211> LENGTH: 746
<212> TYPE: PRT
<213> ORGANISM: Artificial sequence
<220> FEATURE:
<223> OTHER INFORMATION: Synthetic

<400> SEQUENCE: 6

```
Asp Ile Val Met Thr Gln Ser Pro Lys Ile Met Pro Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asp Ser Tyr Pro Leu
                85                  90                  95

Thr Phe Gly Ala Gly Thr Lys Leu Asp Leu Lys Ile Ser Gly Gly Gly
            100                 105                 110

Gly Ser Gly Gly Gly Gly Ser Gly Gly Gly Ser Gly Gly Gly Gly
        115                 120                 125

Ser Gly Gly Gly Gly Ser Ser Glu Val Lys Leu Gln Glu Ser Gly Pro
    130                 135                 140

Ser Leu Val Gln Pro Gly Gly Ser Leu Lys Leu Ser Cys Ala Ala Ser
145                 150                 155                 160

Gly Phe Asp Phe Ser Arg Ser Trp Met Asn Trp Val Arg Gln Ala Pro
                165                 170                 175

Gly Lys Gly Leu Glu Trp Ile Gly Glu Ile Asn Pro Ser Ser Thr
            180                 185                 190

Ile Asn Tyr Thr Thr Ser Leu Lys Asp Lys Phe Ile Ile Ser Arg Asp
        195                 200                 205

Asn Ala Lys Asn Thr Leu Tyr Leu Gln Met Thr Lys Val Arg Ser Glu
    210                 215                 220

Asp Thr Ala Leu Tyr Tyr Cys Ala Arg Tyr Gly Asn Trp Phe Pro Tyr
225                 230                 235                 240

Trp Gly Gln Gly Thr Leu Val Thr Val Ser Ser Leu Glu Pro Lys Ser
                245                 250                 255

Ser Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335
```

-continued

```
Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
355                 360                 365

Ile Glu Lys Thr Ile Ser Lys Ala Lys Gly Gln Pro Arg Glu Pro Gln
        370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
450                 455                 460

Met His Glu Gly Leu His Asn His Tyr Thr Gln Lys Ser Leu Ser Leu
465                 470                 475                 480

Ser Pro Gly Lys Val Asp Gly Ala Ser Ser His Val Asn Val Ser Ser
                485                 490                 495

Pro Ser Val Gln Asp Ile His Val Lys Leu Gln Glu Ser Gly Pro Gly
            500                 505                 510

Leu Val Gln Pro Ser Gln Ser Leu Ser Leu Thr Cys Thr Val Ser Gly
        515                 520                 525

Phe Ser Leu Thr Asp Tyr Gly Val His Trp Val Arg Gln Ser Pro Gly
530                 535                 540

Lys Gly Leu Glu Trp Leu Gly Val Ile Trp Ser Gly Gly Thr Ala
545                 550                 555                 560

Tyr Asn Thr Ala Leu Ile Ser Arg Leu Asn Ile Tyr Arg Asp Asn Ser
                565                 570                 575

Lys Asn Gln Val Phe Leu Glu Met Asn Ser Leu Gln Ala Glu Asp Thr
            580                 585                 590

Ala Met Tyr Tyr Cys Ala Arg Arg Gly Ser Tyr Pro Tyr Asn Tyr Phe
        595                 600                 605

Asp Ala Trp Gly Cys Gly Thr Thr Val Thr Val Ser Ser Gly Gly Gly
610                 615                 620

Gly Ser Gly Gly Gly Gly Ser Gly Gly Gly Gly Ser Gln Ala Val Val
625                 630                 635                 640

Ile Gln Glu Ser Ala Leu Thr Thr Pro Pro Gly Glu Thr Val Thr Leu
                645                 650                 655

Thr Cys Gly Ser Ser Thr Gly Ala Val Thr Ala Ser Asn Tyr Ala Asn
            660                 665                 670

Trp Val Gln Glu Lys Pro Asp His Cys Phe Thr Gly Leu Ile Gly Gly
        675                 680                 685

His Asn Asn Arg Pro Pro Gly Val Pro Ala Arg Phe Ser Gly Ser Leu
690                 695                 700

Ile Gly Asp Lys Ala Ala Leu Thr Ile Ala Gly Thr Gln Thr Glu Asp
705                 710                 715                 720

Glu Ala Ile Tyr Phe Cys Ala Leu Trp Tyr Ser Asp His Trp Val Ile
                725                 730                 735

Gly Gly Gly Thr Arg Leu Thr Val Leu Gly
            740                 745
```

<210> SEQ ID NO 7
<211> LENGTH: 2343
<212> TYPE: DNA
<213> ORGANISM: Artificial sequence
<220> FEATURE:
<223> OTHER INFORMATION: Synthetic

<400> SEQUENCE: 7

| | | | | | |
|---|---|---|---|---|---|
| aagcttgccg | ccatggactt | ccaggtgcag | atcttctcct | tcctgctgat | ctccgcctcc | 60 |
| gtgatcatgt | ccaggggcga | catccagatg | acccagtccc | cctcctccct | gtccgcctcc | 120 |
| gtgggcgaca | gggtgaccat | cacctgctcc | gcctcccagg | acatctccaa | ctacctgaac | 180 |
| tggtaccagc | agaagcccgg | caaggccccc | aagctgctga | tctactacac | ctccaacctg | 240 |
| cactccggcg | tgccctccag | gttctccggc | tccggctccg | gcaccgactt | caccctgacc | 300 |
| atctcctccc | tgcagcccga | ggacttcgcc | acctactact | gccagcagta | caggaagctg | 360 |
| ccctggacct | tcggccaggg | caccaagctg | gagatcaaga | ggtccggcgg | cggcggcagc | 420 |
| ggaggaggag | aagcggaggc | ggcggctccg | gcggcggcg | ctccggcgg | cggcggctcc | 480 |
| tcccaggtgc | agctggtgca | gtccggcgcc | gaggtgaaga | agcccggctc | ctccgtgaag | 540 |
| gtgtcctgca | aggcctccgg | cggcaccttc | tccaactact | ggatgcactg | ggtgaggcag | 600 |
| gcccccggcc | agggcctgga | gtggatgggc | gccacctaca | ggggccactc | cgacacctac | 660 |
| tacaaccaga | agttcaaggg | cagggtgacc | atcaccgccg | acaagtccac | ctccaccgcc | 720 |
| tacatggagc | tgtcctccct | gaggtccgag | gacaccgccg | tgtactactg | cgccaggggc | 780 |
| gccatctacg | acggctacga | cgtgctggac | aactggggcc | agggcaccct | ggtgaccgtg | 840 |
| tcctcccctcg | agcccaaatc | ttctgacaaa | actcacacat | gtccaccgtg | cccagcacct | 900 |
| gaactcctgg | ggggaccgtc | agtcttcctc | ttccccccaa | aacccaagga | caccctcatg | 960 |
| atctcccgga | cccctgaggt | cacatgcgtg | gtggtggacg | tgagccacga | agaccctgag | 1020 |
| gtcaagttca | actggtacgt | ggacggcgtg | gaggtgcata | atgccaagac | aaagccgcgg | 1080 |
| gaggagcagt | acaacagcac | gtaccgtgtg | gtcagcgtcc | tcaccgtcct | gcaccaggac | 1140 |
| tggctgaatg | gcaaggagta | caagtgcaag | gtctccaaca | aagccctccc | agcccccatc | 1200 |
| gagaaaacca | tctccaaagc | caaagggcag | ccccgagaac | cacaggtgta | caccctgccc | 1260 |
| ccatcccggg | atgagctgac | caagaaccag | gtcagcctga | cctgcctggt | caaaggcttc | 1320 |
| tatcccagcg | acatcgccgt | ggagtgggag | agcaatgggc | agccggagaa | caactacaag | 1380 |
| accacgcctc | ccgtgctgga | ctccgacggc | tccttcttcc | tctacagcaa | gctcaccgtg | 1440 |
| gacaagagca | ggtggcagca | ggggaacgtc | ttctcatgct | ccgtgatgca | tgagggtctg | 1500 |
| cacaaccact | acacgcagaa | gagcctctct | ctgtctccgg | gtaaagtcga | cggtgctagc | 1560 |
| agccatgtga | atgtgagcag | ccctagcgtg | caggatatcc | acgttaagtt | gcaagaatct | 1620 |
| ggtccaggtt | tggttcagcc | atctcaatct | ttgtctctta | cttgtactgt | ttctggtttc | 1680 |
| tctttgactg | attatggtgt | tcattgggtt | agacaatctc | caggtaaagg | tttggaatgg | 1740 |
| ttgggtgtta | tttggtctgg | tggaggtact | gcttataata | ctgctttgat | ttctaggttg | 1800 |
| aatatttatc | gagataattc | taaaaatcaa | gttttcttg | aaatgaattc | tttgcaagct | 1860 |
| gaagatactg | ctatgtatta | ttgtgctaga | agaggttctt | atccatataa | ttattttgat | 1920 |
| gcttggggtt | gtggtactac | tgttactgtt | tcttctggag | gcggcggatc | tggcggtgga | 1980 |
| ggttctggcg | gcggcggatc | tcaagctgtt | gttattcaag | aatctgcttt | gactactcct | 2040 |
| ccaggtgaaa | ccgttacttt | gacttgtgga | tcttctactg | gtgctgttac | tgcttctaat | 2100 |

```
tatgctaatt gggttcaaga aaaaccagat cattgcttta ctggtttgat tggtggtcat    2160
aataatagac caccaggtgt tccggctaga ttttctggtt ctttgattgg tgataaagct    2220
gctttgacta ttgctggtac tcaaactgaa gatgaagcta tttattttg tgctttgtgg    2280 tattctgatc attgggttat tggtggtggt actagattga ctgttttggg ctaataatct    2340
aga                                                                  2343
```

<210> SEQ ID NO 8
<211> LENGTH: 751
<212> TYPE: PRT
<213> ORGANISM: Artificial sequence
<220> FEATURE:
<223> OTHER INFORMATION: Synthetic

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Ser Gly Gly Gly
            100                 105                 110

Gly Ser Gly Gly Gly Gly Ser Gly Gly Gly Ser Gly Gly Gly Gly
        115                 120                 125

Ser Gly Gly Gly Gly Ser Ser Gln Val Gln Leu Val Gln Ser Gly Ala
    130                 135                 140

Glu Val Lys Lys Pro Gly Ser Ser Val Lys Val Ser Cys Lys Ala Ser
145                 150                 155                 160

Gly Gly Thr Phe Ser Asn Tyr Trp Met His Trp Val Arg Gln Ala Pro
                165                 170                 175

Gly Gln Gly Leu Glu Trp Met Gly Ala Thr Tyr Arg Gly His Ser Asp
            180                 185                 190

Thr Tyr Tyr Asn Gln Lys Phe Lys Gly Arg Val Thr Ile Thr Ala Asp
        195                 200                 205

Lys Ser Thr Ser Thr Ala Tyr Met Glu Leu Ser Ser Leu Arg Ser Glu
    210                 215                 220

Asp Thr Ala Val Tyr Tyr Cys Ala Arg Gly Ala Ile Tyr Asp Gly Tyr
225                 230                 235                 240

Asp Val Leu Asp Asn Trp Gly Gln Gly Thr Leu Val Thr Val Ser Ser
                245                 250                 255

Leu Glu Pro Lys Ser Ser Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320
```

-continued

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
450                 455                 460

Phe Ser Cys Ser Val Met His Glu Gly Leu His Asn His Tyr Thr Gln
465                 470                 475                 480

Lys Ser Leu Ser Leu Ser Pro Gly Lys Val Asp Gly Ala Ser Ser His
            485                 490                 495

Val Asn Val Ser Ser Pro Ser Val Gln Asp Ile His Val Lys Leu Gln
            500                 505                 510

Glu Ser Gly Pro Gly Leu Val Gln Pro Ser Gln Ser Leu Ser Leu Thr
            515                 520                 525

Cys Thr Val Ser Gly Phe Ser Leu Thr Asp Tyr Gly Val His Trp Val
530                 535                 540

Arg Gln Ser Pro Gly Lys Gly Leu Glu Trp Leu Gly Val Ile Trp Ser
545                 550                 555                 560

Gly Gly Gly Thr Ala Tyr Asn Thr Ala Leu Ile Ser Arg Leu Asn Ile
            565                 570                 575

Tyr Arg Asp Asn Ser Lys Asn Gln Val Phe Leu Glu Met Asn Ser Leu
            580                 585                 590

Gln Ala Glu Asp Thr Ala Met Tyr Tyr Cys Ala Arg Arg Gly Ser Tyr
            595                 600                 605

Pro Tyr Asn Tyr Phe Asp Ala Trp Gly Cys Gly Thr Thr Val Thr Val
            610                 615                 620

Ser Ser Gly Gly Gly Gly Ser Gly Gly Gly Gly Ser Gly Gly Gly Gly
625                 630                 635                 640

Ser Gln Ala Val Val Ile Gln Glu Ser Ala Leu Thr Thr Pro Pro Gly
            645                 650                 655

Glu Thr Val Thr Leu Thr Cys Gly Ser Ser Thr Gly Ala Val Thr Ala
            660                 665                 670

Ser Asn Tyr Ala Asn Trp Val Gln Glu Lys Pro Asp His Cys Phe Thr
            675                 680                 685

Gly Leu Ile Gly Gly His Asn Asn Arg Pro Pro Gly Val Pro Ala Arg
690                 695                 700

Phe Ser Gly Ser Leu Ile Gly Asp Lys Ala Ala Leu Thr Ile Ala Gly
705                 710                 715                 720

Thr Gln Thr Glu Asp Glu Ala Ile Tyr Phe Cys Ala Leu Trp Tyr Ser
            725                 730                 735

Asp His Trp Val Ile Gly Gly Gly Thr Arg Leu Thr Val Leu Gly
    740                 745                 750

<210> SEQ ID NO 9
<211> LENGTH: 2304
<212> TYPE: DNA
<213> ORGANISM: Artificial sequence
<220> FEATURE:
<223> OTHER INFORMATION: Synthetic

<400> SEQUENCE: 9

| | | | | |
|---|---|---|---|---|
| aagcttgccg ccatggattt tcaagtgcag attttcagct tcctgctaat cagtgcttca | 60 |
| gtcataatgt ccagaggaca gatccagctg gtgcagtctg gccccgagct gaagaaaccc | 120 |
| ggcgagacag tgaagatcag ctgcaaggcc agcggctaca ccttcaccga ctacagcatc | 180 |
| aactgggtca agagagcccc tggcaagggc ctgaagtgga tgggctggat caacaccgaa | 240 |
| accagagagc ccgcctacgc ctacgacttc agaggcagat tcgccttcag cctggaaacc | 300 |
| agcgccagca ccgcctacct gcagatcaac aacctgaagt acgaggacac cgccacctac | 360 |
| ttttgcgccc tggactacag ctacgccatg gactattggg gccagggcac cagcgtgacc | 420 |
| gtgtctagcg gaggcggagg atctggcgga ggggctccg gaggggagg ctctgatatt | 480 |
| gtgctgaccc agagcccccc cagcctggcc atgtctctgg aaagagagc caccatcagc | 540 |
| tgccgggcct ctgagagcgt gacaatcctg ggcagccacc tgatccactg gtatcagcag | 600 |
| aagcccggcc agccccctac cctgctgatt cagctggcct ccaatgtgca gaccggcgtg | 660 |
| ccagccagat tttccggcag cggcagcaga accgacttca ccctgaccat cgaccccgtg | 720 |
| gaagaggacg acgtggccgt gtactactgc ctgcagagcc ggaccatccc cagaaccttt | 780 |
| ggcgaggca ccaagctgga aatcaaactc gagcccaaat cttctgacaa aactcacaca | 840 |
| tgtccaccgt gcccagcacc tgaactcctg ggggaccgt cagtcttcct cttccccca | 900 |
| aaacccaagg acaccctcat gatctcccgg acccctgagg tcacatgcgt ggtggtggac | 960 |
| gtgagccacg aagaccctga ggtcaagttc aactggtacg tggacggcgt ggaggtgcat | 1020 |
| aatgccaaga caaagccgcg ggaggagcag tacaacagca cgtaccgtgt ggtcagcgtc | 1080 |
| ctcaccgtcc tgcaccagga ctggctgaat ggcaaggagt acaagtgcaa ggtctccaac | 1140 |
| aaagccctcc cagcccccat cgagaaaacc atctccaaag ccaaagggca gccccgagaa | 1200 |
| ccacaggtgt acaccctgcc cccatcccgg gatgagctga ccaagaacca ggtcagcctg | 1260 |
| acctgcctgg tcaaaggctt ctatcccagc gacatcgccg tggagtggga gagcaatggg | 1320 |
| cagccggaga caactacaa gaccacgcct cccgtgctgg actccgacgg ctccttcttc | 1380 |
| ctctacagca agctcaccgt ggacaagagc aggtggcagc aggggaacgt cttctcatgc | 1440 |
| tccgtgatgc atgagggtct gcacaaccac tacacgcaga gagcctctc tctgtctccg | 1500 |
| ggtaaagtcg acggtgctag cagccatgtg aatgtgagca gccctagcgt gcaggatatc | 1560 |
| cacgttaagt tgcaagaatc tggtccaggt ttggttcagc catctcaatc tttgtctctt | 1620 |
| acttgtactg tttctggttt ctctttgact gattatggtg ttcattgggt tagacaatct | 1680 |
| ccaggtaaag gtttgaatg gttgggtgtt atttggtctg gtggaggtac tgcttataat | 1740 |
| actgctttga tttctaggtt gaatatttat cgagataatt ctaaaaatca gttttttctt | 1800 |
| gaaatgaatt ctttgcaagc tgaagatact gctatgtatt attgtgctag aagaggttct | 1860 |
| tatccatata attattttga tgcttggggt tgtggtacta ctgttactgt tcttctggaa | 1920 |
| ggcggcggat ctggcggtgg aggttctggc ggcggcggat ctcaagctgt tgttattcaa | 1980 |

-continued

```
gaatctgctt tgactactcc tccaggtgaa accgttactt tgacttgtgg atcttctact    2040
ggtgctgtta ctgcttctaa ttatgctaat tgggttcaag aaaaaccaga tcattgcttt    2100
actggtttga ttggtggtca taataataga ccaccaggtg ttccggctag attttctggt    2160
tctttgattg gtgataaagc tgctttgact attgctggta ctcaaactga agatgaagct    2220
atttattttt gtgctttgtg gtattctgat cattgggtta ttggtggtgg tactagattg    2280
actgttttgg gctaataatc taga                                           2304
```

<210> SEQ ID NO 10
<211> LENGTH: 738
<212> TYPE: PRT
<213> ORGANISM: Artificial sequence
<220> FEATURE:
<223> OTHER INFORMATION: Synthetic

<400> SEQUENCE: 10

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Gly Gly Gly Ser Gly Gly Gly Gly Ser Gly
        115                 120                 125

Gly Gly Gly Ser Asp Ile Val Leu Thr Gln Ser Pro Pro Ser Leu Ala
    130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile His Trp Tyr Gln Gln Lys Pro
                165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
        195                 200                 205

Leu Thr Ile Asp Pro Val Glu Glu Asp Asp Val Ala Val Tyr Tyr Cys
    210                 215                 220

Leu Gln Ser Arg Thr Ile Pro Arg Thr Phe Gly Gly Gly Thr Lys Leu
225                 230                 235                 240

Glu Ile Lys Leu Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300
```

```
Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
        340                 345                 350

Ser Asn Lys Ala Leu Pro Ala Pro Ile Glu Lys Thr Ile Ser Lys Ala
    355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Gly Leu His Asn His
450                 455                 460

Tyr Thr Gln Lys Ser Leu Ser Leu Ser Pro Gly Lys Val Asp Gly Ala
465                 470                 475                 480

Ser Ser His Val Asn Val Ser Ser Pro Ser Val Gln Asp Ile His Val
                485                 490                 495

Lys Leu Gln Glu Ser Gly Pro Gly Leu Val Gln Pro Ser Gln Ser Leu
            500                 505                 510

Ser Leu Thr Cys Thr Val Ser Gly Phe Ser Leu Thr Asp Tyr Gly Val
        515                 520                 525

His Trp Val Arg Gln Ser Pro Gly Lys Gly Leu Glu Trp Leu Gly Val
        530                 535                 540

Ile Trp Ser Gly Gly Thr Ala Tyr Asn Thr Ala Leu Ile Ser Arg
545                 550                 555                 560

Leu Asn Ile Tyr Arg Asp Asn Ser Lys Asn Gln Val Phe Leu Glu Met
                565                 570                 575

Asn Ser Leu Gln Ala Glu Asp Thr Ala Met Tyr Tyr Cys Ala Arg Arg
            580                 585                 590

Gly Ser Tyr Pro Tyr Asn Tyr Phe Asp Ala Trp Gly Cys Gly Thr Thr
        595                 600                 605

Val Thr Val Ser Ser Gly Gly Gly Ser Gly Gly Gly Ser Gly
610                 615                 620

Gly Gly Gly Ser Gln Ala Val Val Ile Gln Glu Ser Ala Leu Thr Thr
625                 630                 635                 640

Pro Pro Gly Glu Thr Val Thr Leu Thr Cys Gly Ser Ser Thr Gly Ala
                645                 650                 655

Val Thr Ala Ser Asn Tyr Ala Asn Trp Val Gln Glu Lys Pro Asp His
            660                 665                 670

Cys Phe Thr Gly Leu Ile Gly Gly His Asn Asn Arg Pro Pro Gly Val
        675                 680                 685

Pro Ala Arg Phe Ser Gly Ser Leu Ile Gly Asp Lys Ala Ala Leu Thr
        690                 695                 700

Ile Ala Gly Thr Gln Thr Glu Asp Glu Ala Ile Tyr Phe Cys Ala Leu
705                 710                 715                 720

Trp Tyr Ser Asp His Trp Val Ile Gly Gly Gly Thr Arg Leu Thr Val
```

Leu Gly

<210> SEQ ID NO 11
<211> LENGTH: 2328
<212> TYPE: DNA
<213> ORGANISM: Artificial sequence
<220> FEATURE:
<223> OTHER INFORMATION: Synthetic

<400> SEQUENCE: 11

| | | | | | |
|---|---|---|---|---|---|
| aagcttgccg | ccatggattt | tcaagtgcag | attttcagct | tcctgctaat | cagtgcttca | 60 |
| gtcataatgt | ccagaggaca | aattgttctc | tcccagtctc | cagcaatcct | gtctgcatct | 120 |
| ccaggggaga | aggtcacaat | gacttgcagg | gccagctcaa | gtgtaagtta | catgcactgg | 180 |
| taccagcaga | agccaggatc | ctcccccaaa | ccctggattt | atgccccatc | caacctggct | 240 |
| tctggagtcc | ctgctcgctt | cagtggcagt | gggtctggga | cctcttactc | tctcacaatc | 300 |
| agcagagtgg | aggctgaaga | tgctgccact | tattactgcc | agcagtggag | ttttaaccca | 360 |
| cccacgttcg | gtgctgggac | caagctggag | ctgaaagatg | gcggtggctc | gggcggtggt | 420 |
| ggatctggag | gaggtgggag | cggggaggag | ggaagctcta | ccggtcaggc | ttatctacag | 480 |
| cagtctgggg | ctgagtcggt | gaggcctggg | gcctcagtga | agatgtcctg | caaggcttct | 540 |
| ggctacacat | ttaccagtta | caatatgcac | tgggtaaagc | agacacctag | acagggcctg | 600 |
| gaatggattg | gagctattta | tccaggaaat | ggtgatactt | cctacaatca | gaagttcaag | 660 |
| ggcaaggcca | cactgactgt | agacaaatcc | tccagcacag | cctacatgca | gctcagcagc | 720 |
| ctgacatctg | aagactctgc | ggtctatttc | tgtgcaagag | tggtgtacta | tagtaactct | 780 |
| tactggtact | tcgatgtctg | gggcacaggg | accacggtca | ccgtctcttc | tctcgagccc | 840 |
| aaatcttctg | acaaaactca | cacatgtcca | ccgtgcccag | cacctgaact | cctgggggga | 900 |
| ccgtcagtct | tcctcttccc | cccaaaaccc | aaggacaccc | tcatgatctc | ccggacccct | 960 |
| gaggtcacat | gcgtggtggt | ggacgtgagc | cacgaagacc | ctgaggtcaa | gttcaactgg | 1020 |
| tacgtggacg | gcgtggaggt | gcataatgcc | aagacaaagc | cgcgggagga | gcagtacaac | 1080 |
| agcacgtacc | gtgtggtcag | cgtcctcacc | gtcctgcacc | aggactggct | gaatggcaag | 1140 |
| gagtacaagt | gcaaggtctc | caacaaagcc | ctcccagccc | ccatcgagaa | aaccatctcc | 1200 |
| aaagccaaag | ggcagccccg | agaaccacag | gtgtacaccc | tgcccccatc | ccgggatgag | 1260 |
| ctgaccaaga | accaggtcag | cctgacctgc | ctggtcaaag | gcttctatcc | cagcgacatc | 1320 |
| gccgtggagt | gggagagcaa | tgggcagccg | gagaacaact | acaagaccac | gcctcccgtg | 1380 |
| ctggactccg | acggctcctt | cttcctctac | agcaagctca | ccgtggacaa | gagcaggtgg | 1440 |
| cagcagggga | acgtcttctc | atgctccgtg | atgcatgagg | gtctgcacaa | ccactacacg | 1500 |
| cagaagagcc | tctctctgtc | tccgggtaaa | gtcgacggtg | ctagcagcca | tgtgaatgtg | 1560 |
| agcagcccta | gcgtgcagga | tatccacgtt | aagttgcaag | aatctggtcc | aggtttggtt | 1620 |
| cagccatctc | aatctttgtc | tcttacttgt | actgtttctg | gtttctcttt | gactgattat | 1680 |
| ggtgttcatt | gggttagaca | atctccaggt | aaaggtttgg | aatggttggg | tgttatttgg | 1740 |
| tctggtggag | gtactgctta | taatactgct | ttgatttcta | ggttgaatat | ttatcgagat | 1800 |
| aattctaaaa | atcaagttttt | tcttgaaatg | aattctttgc | aagctgaaga | tactgctatg | 1860 |
| tattattgtg | ctagaagagg | ttcttatcca | tataattatt | ttgatgcttg | gggttgtggt | 1920 |
| actactgtta | ctgtttcttc | tggaggcggc | ggatctggcg | gtggaggttc | tggcggcggc | 1980 |

```
ggatctcaag ctgttgttat tcaagaatct gctttgacta ctcctccagg tgaaaccgtt   2040
actttgactt gtggatcttc tactggtgct gttactgctt ctaattatgc taattgggtt   2100
caagaaaaac cagatcattg ctttactggt ttgattggtg gtcataataa tagaccacca   2160
ggtgttccgg ctagattttc tggttctttg attggtgata aagctgcttt gactattgct   2220
ggtactcaaa ctgaagatga agctatttat ttttgtgctt tgtggtattc tgatcattgg   2280
gttattggtg gtggtactag attgactgtt ttgggctaat aatctaga               2328
```

<210> SEQ ID NO 12
<211> LENGTH: 746
<212> TYPE: PRT
<213> ORGANISM: Artificial sequence
<220> FEATURE:
<223> OTHER INFORMATION: Synthetic

<400> SEQUENCE: 12

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Asp Gly Gly Gly Ser Gly
            100                 105                 110

Gly Gly Gly Ser Gly Gly Gly Ser Gly Gly Gly Ser Ser Thr
        115                 120                 125

Gly Gln Ala Tyr Leu Gln Gln Ser Gly Ala Glu Ser Val Arg Pro Gly
    130                 135                 140

Ala Ser Val Lys Met Ser Cys Lys Ala Ser Gly Tyr Thr Phe Thr Ser
145                 150                 155                 160

Tyr Asn Met His Trp Val Lys Gln Thr Pro Arg Gln Gly Leu Glu Trp
                165                 170                 175

Ile Gly Ala Ile Tyr Pro Gly Asn Gly Asp Thr Ser Tyr Asn Gln Lys
            180                 185                 190

Phe Lys Gly Lys Ala Thr Leu Thr Val Asp Lys Ser Ser Ser Thr Ala
        195                 200                 205

Tyr Met Gln Leu Ser Ser Leu Thr Ser Glu Asp Ser Ala Val Tyr Phe
    210                 215                 220

Cys Ala Arg Val Val Tyr Tyr Ser Asn Ser Tyr Trp Tyr Phe Asp Val
225                 230                 235                 240

Trp Gly Thr Gly Thr Thr Val Thr Val Ser Ser Leu Glu Pro Lys Ser
                245                 250                 255

Ser Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300
```

```
His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
450                 455                 460

Met His Glu Gly Leu His Asn His Tyr Thr Gln Lys Ser Leu Ser Leu
465                 470                 475                 480

Ser Pro Gly Lys Val Asp Gly Ala Ser Ser His Val Asn Val Ser Ser
                485                 490                 495

Pro Ser Val Gln Asp Ile His Val Lys Leu Gln Glu Ser Gly Pro Gly
            500                 505                 510

Leu Val Gln Pro Ser Gln Ser Leu Ser Leu Thr Cys Thr Val Ser Gly
        515                 520                 525

Phe Ser Leu Thr Asp Tyr Gly Val His Trp Val Arg Gln Ser Pro Gly
530                 535                 540

Lys Gly Leu Glu Trp Leu Gly Val Ile Trp Ser Gly Gly Gly Thr Ala
545                 550                 555                 560

Tyr Asn Thr Ala Leu Ile Ser Arg Leu Asn Ile Tyr Arg Asp Asn Ser
                565                 570                 575

Lys Asn Gln Val Phe Leu Glu Met Asn Ser Leu Gln Ala Glu Asp Thr
            580                 585                 590

Ala Met Tyr Tyr Cys Ala Arg Arg Gly Ser Tyr Pro Tyr Asn Tyr Phe
        595                 600                 605

Asp Ala Trp Gly Cys Gly Thr Thr Val Thr Val Ser Ser Gly Gly Gly
610                 615                 620

Gly Ser Gly Gly Gly Gly Ser Gly Gly Gly Gly Ser Gln Ala Val Val
625                 630                 635                 640

Ile Gln Glu Ser Ala Leu Thr Thr Pro Pro Gly Glu Thr Val Thr Leu
                645                 650                 655

Thr Cys Gly Ser Ser Thr Gly Ala Val Thr Ala Ser Asn Tyr Ala Asn
            660                 665                 670

Trp Val Gln Glu Lys Pro Asp His Cys Phe Thr Gly Leu Ile Gly Gly
        675                 680                 685

His Asn Asn Arg Pro Pro Gly Val Pro Ala Arg Phe Ser Gly Ser Leu
690                 695                 700

Ile Gly Asp Lys Ala Ala Leu Thr Ile Ala Gly Thr Gln Thr Glu Asp
705                 710                 715                 720
```

```
Glu Ala Ile Tyr Phe Cys Ala Leu Trp Tyr Ser Asp His Trp Val Ile
            725                 730                 735
Gly Gly Gly Thr Arg Leu Thr Val Leu Gly
        740                 745

<210> SEQ ID NO 13
<211> LENGTH: 2322
<212> TYPE: DNA
<213> ORGANISM: Artificial sequence
<220> FEATURE:
<223> OTHER INFORMATION: Synthetic

<400> SEQUENCE: 13
aagcttgccg ccatggattt tcaagtgcag attttcagct tcctgctaat cagtgcttca     60
gtcataatgt ccagaggaga cattgtgatg actcagacac cactgagctc cccagtgact    120
ctgggacagc cagccagtat ctcatgcaga tctagtcagt cactggtcta cagcgacggc    180
aacacctatc tgagctggct gcagcagcga ccaggacagc cacctagact gctgatctac    240
aagatttcca ataggttctc tggagtgccc gaccgcttta gcggatccgg agctggaact    300
gatttcaccc tgaaaatctc cgcgtggag gctgaagatg tgggcgtcta ctattgcgtc    360
caggcaaccc agttccctct gacatttggc ggggaacta aggtggagat caagggagga    420
ggaggatctg gaggaggagg aagtggagga ggaggatccg aagtgcagct ggtccagtct    480
ggggccgagg tgaagaaacc tggagaaagt ctgaagatct catgtaaagg ctccgggtac    540
tctttcacaa gttattggat tggctgggtc cgacagatgc aggaaaggg cctggagtgg    600 atgggaatca tctaccccgg cgacagcgat accggtatt ctcctagttt tcagggccag    660
gtgacaatca gcgcagacaa gtccattacc acagcctatc tgcagtggtc aagcctgaaa    720
gcctctgata ccgctatgta ctattgtgcc aggcacccta gctacgggtc aggaagccca    780
aactttgact attggggcca ggggacactg gtgactgtct cctcactcga gcccaaatct    840
tctgacaaaa ctcacacatg tccaccgtgc ccagcacctg aactcctggg gggaccgtca    900
gtcttcctct ccccccaaa acccaaggac accctcatga tctcccggac ccctgaggtc    960
acatgcgtgg tggtggacgt gagccacgaa gaccctgagg tcaagttcaa ctggtacgtg   1020
gacggcgtgg aggtgcataa tgccaagaca aagccgcggg aggagcagta caacagcacg   1080
taccgtgtgt cagcgtcct caccgtcctg caccaggact ggctgaatgg caaggagtac   1140
aagtgcaagg tctccaacaa agccctccca gcccccatcg agaaaaccat ctccaaagcc   1200
aaagggcagc cccgagaacc acaggtgtac accctgcccc catcccggga tgagctgacc   1260
aagaaccagg tcagcctgac ctgcctggtc aaaggcttct atcccagcga catcgccgtg   1320
gagtgggaga gcaatgggca gccggagaac aactacaaga ccacgcctcc cgtgctggac   1380
tccgacggct ccttcttcct ctacagcaag ctcaccgtgg acaagagcag gtggcagcag   1440
gggaacgtct tctcatgctc cgtgatgcat gagggtctgc acaaccacta cacgcagaag   1500
agcctctctc tgtctccggg taaagtcgac ggtgctagca gccatgtgaa gtgagcagc   1560 cctagcgtgc aggatatcca cgttaagttg caagaatctg gtccaggttt ggttcagcca   1620
tctcaatctt tgtctcttac ttgtactgtt tctggtttct cttttgactga ttatggtgtt   1680 cattgggtta gacaatctcc aggtaaaggt ttggaatggt gggtgttat ttggtctggt   1740 ggaggtactg cttataatac tgctttgatt tctaggttga atatttatcg agataattct   1800
aaaaatcaag ttttcttga atgaattct ttgcaagctg aagatactgc tatgtattat   1860
tgtgctagaa gaggttctta tccatataat tattttgatg cttggggttg tggtactact   1920
```

```
gttactgtttc cttctggagg cggcggatct ggcggtggag gttctggcgg cggcggatct    1980
caagctgttg ttattcaaga atctgctttg actactcctc caggtgaaac cgttactttg    2040
acttgtggat cttctactgg tgctgttact gcttctaatt atgctaattg ggttcaagaa    2100
aaaccagatc attgctttac tggtttgatt ggtggtcata ataatagacc accaggtgtt    2160
ccggctagat tttctggttc tttgattggt gataaagctg ctttgactat tgctggtact    2220
caaactgaag atgaagctat ttattttgt gctttgtggt attctgatca ttgggttatt    2280
ggtggtggta ctagattgac tgttttgggc taataatcta ga                      2322
```

<210> SEQ ID NO 14
<211> LENGTH: 744
<212> TYPE: PRT
<213> ORGANISM: Artificial sequence
<220> FEATURE:
<223> OTHER INFORMATION: Synthetic

<400> SEQUENCE: 14

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Glu Ser
    130                 135                 140

Leu Lys Ile Ser Cys Lys Gly Ser Gly Tyr Ser Phe Thr Ser Tyr Trp
145                 150                 155                 160

Ile Gly Trp Val Arg Gln Met Pro Gly Lys Gly Leu Glu Trp Met Gly
                165                 170                 175

Ile Ile Tyr Pro Gly Asp Ser Asp Thr Arg Tyr Ser Pro Ser Phe Gln
            180                 185                 190

Gly Gln Val Thr Ile Ser Ala Asp Lys Ser Ile Thr Thr Ala Tyr Leu
        195                 200                 205

Gln Trp Ser Ser Leu Lys Ala Ser Asp Thr Ala Met Tyr Tyr Cys Ala
    210                 215                 220

Arg His Pro Ser Tyr Gly Ser Gly Ser Pro Asn Phe Asp Tyr Trp Gly
225                 230                 235                 240

Gln Gly Thr Leu Val Thr Val Ser Ser Leu Glu Pro Lys Ser Ser Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285
```

```
Ser Arg Thr Pro Glu Val Thr Cys Val Val Val Asp Val Ser His Glu
    290             295             300
Asp Pro Glu Val Lys Phe Asn Trp Tyr Val Asp Gly Val Glu Val His
305             310             315             320
Asn Ala Lys Thr Lys Pro Arg Glu Glu Gln Tyr Asn Ser Thr Tyr Arg
                325             330             335
Val Val Ser Val Leu Thr Val Leu His Gln Asp Trp Leu Asn Gly Lys
            340             345             350
Glu Tyr Lys Cys Lys Val Ser Asn Lys Ala Leu Pro Ala Pro Ile Glu
        355             360             365
Lys Thr Ile Ser Lys Ala Lys Gly Gln Pro Arg Glu Pro Gln Val Tyr
    370             375             380
Thr Leu Pro Pro Ser Arg Asp Glu Leu Thr Lys Asn Gln Val Ser Leu
385             390             395             400
Thr Cys Leu Val Lys Gly Phe Tyr Pro Ser Asp Ile Ala Val Glu Trp
                405             410             415
Glu Ser Asn Gly Gln Pro Glu Asn Asn Tyr Lys Thr Thr Pro Pro Val
            420             425             430
Leu Asp Ser Asp Gly Ser Phe Phe Leu Tyr Ser Lys Leu Thr Val Asp
        435             440             445
Lys Ser Arg Trp Gln Gln Gly Asn Val Phe Ser Cys Ser Val Met His
    450             455             460
Glu Gly Leu His Asn His Tyr Thr Gln Lys Ser Leu Ser Leu Ser Pro
465             470             475             480
Gly Lys Val Asp Gly Ala Ser Ser His Val Asn Val Ser Ser Pro Ser
                485             490             495
Val Gln Asp Ile His Val Lys Leu Gln Glu Ser Gly Pro Gly Leu Val
            500             505             510
Gln Pro Ser Gln Ser Leu Ser Leu Thr Cys Thr Val Ser Gly Phe Ser
        515             520             525
Leu Thr Asp Tyr Gly Val His Trp Val Arg Gln Ser Pro Gly Lys Gly
    530             535             540
Leu Glu Trp Leu Gly Val Ile Trp Ser Gly Gly Gly Thr Ala Tyr Asn
545             550             555             560
Thr Ala Leu Ile Ser Arg Leu Asn Ile Tyr Arg Asp Asn Ser Lys Asn
                565             570             575
Gln Val Phe Leu Glu Met Asn Ser Leu Gln Ala Glu Asp Thr Ala Met
            580             585             590
Tyr Tyr Cys Ala Arg Arg Gly Ser Tyr Pro Tyr Asn Tyr Phe Asp Ala
        595             600             605
Trp Gly Cys Gly Thr Thr Val Thr Val Ser Ser Gly Gly Gly Gly Ser
    610             615             620
Gly Gly Gly Gly Ser Gly Gly Gly Ser Gln Ala Val Val Ile Gln
625             630             635             640
Glu Ser Ala Leu Thr Thr Pro Pro Gly Glu Thr Val Thr Leu Thr Cys
                645             650             655
Gly Ser Ser Thr Gly Ala Val Thr Ala Ser Asn Tyr Ala Asn Trp Val
            660             665             670
Gln Glu Lys Pro Asp His Cys Phe Thr Gly Leu Ile Gly Gly His Asn
        675             680             685
Asn Arg Pro Pro Gly Val Pro Ala Arg Phe Ser Gly Ser Leu Ile Gly
    690             695             700
Asp Lys Ala Ala Leu Thr Ile Ala Gly Thr Gln Thr Glu Asp Glu Ala
```

```
                    705                 710                 715                 720
              Ile Tyr Phe Cys Ala Leu Trp Tyr Ser Asp His Trp Val Ile Gly Gly
                              725                 730                 735
              Gly Thr Arg Leu Thr Val Leu Gly
                        740

<210> SEQ ID NO 15
<211> LENGTH: 2337
<212> TYPE: DNA
<213> ORGANISM: Artificial sequence
<220> FEATURE:
<223> OTHER INFORMATION: Synthetic

<400> SEQUENCE: 15
aagcttgccg ccatggactt ccaggtgcag atcttctcct tcctgctgat ctccgcctcc     60
gtgatcatgt ccaggggcga catccagatg acccagtccc cctcctccct gtccgcctcc    120
gtgggcgaca gggtgaccat cacctgcaag gcctcccagg acgtgggcat cgccgtggcc    180
tggtaccagc agaagcccgg caaggtgccc aagctgctga tctactgggc ctccaccagg    240
cacaccggcg tgcccgacag gttctccggc tccggctccg gcaccgactt caccctgacc    300
atctcctccc tacagcccga ggacgtggcc acctactact gccagcagta ctcctcctac    360
ccctacacct tcggccaggg caccaaggtg gagatcaaga tctctggtgg cggcggctcg    420
ggcggtggtg ggtcgggtgg cggtggctcg ggcggtggtg ggtcgggcgg cggcggttcg    480
agcgaggtgc agctggtgga gtccggcggc ggcctggtgc agcccggcgg ctccctgagg    540
ctgtcctgcg ccgcctccgg cttcgacttc tccaggtact ggatgtcctg ggtgaggcag    600 gccccggca  agggcctgga gtggatcggc gagatcaacc ccgactcctc caccatcaac    660
tacgccccct ccctgaagga caagttcatc atctccaggg acaacgccaa gaactccctg    720
tacctgcaga tgaactccct gagggccgag gacaccgccg tgtactactg cgccaggccc    780
gacggcaact actggtactt cgacgtgtgg ggccagggca ccctggtgac cgtgtcctcc    840
ctcgagccca atcttctga  caaaactcac acatgtccac cgtgcccagc acctgaactc    900 ctgggggga  cgtcagtctt cctcttcccc ccaaaaccca aggacaccct catgatctcc    960
cggacccctg aggtcacatg cgtggtggtg gacgtgagcc acgaagaccc tgaggtcaag   1020
ttcaactggt acgtggacgg cgtggaggtg cataatgcca agacaaagcc gcgggaggag   1080
cagtacaaca gcacgtaccg tgtggtcagc gtcctcaccg tcctgcacca ggactggctg   1140
aatggcaagg agtacaagtg caaggtctcc aacaaagccc tcccagcccc catcgagaaa   1200
accatctcca aagccaaagg gcagcccga  gaaccacagg tgtacaccct gcccccatcc   1260
cgggatgagc tgaccaagaa ccaggtcagc ctgacctgcc tggtcaaagg cttctatccc   1320
agcgacatcg ccgtggagtg ggagagcaat gggcagccgg agaacaacta caagaccacg   1380
cctcccgtgc tggactccga cggctccttc ttcctctaca gcaagctcac cgtggacaag   1440
agcaggtggc agcaggggaa cgtcttctca tgctccgtga tgcatgaggg tctgcacaac   1500
cactacacgc agaagagcct ctctctgtct ccgggtaaag tcgacggtgc tagcagccat   1560
gtgaatgtga gcagccctag cgtgcaggat atccacgtta agttgcaaga atctggtcca   1620
ggtttggttc agccatctca atctttgtct cttacttgta ctgtttctgg tttctctttg   1680
actgattatg gtgttcattg ggttagacaa tctccaggta aaggtttgga atggttgggt   1740
gttatttggt ctggtggagg tactgcttat aatactgctt tgatttctag gttgaatatt   1800
tatcgagata attctaaaaa tcaagttttt cttgaaatga attctttgca agctgaagat   1860
```

```
actgctatgt attattgtgc tagaagaggt tcttatccat ataattattt tgatgcttgg    1920
ggttgtggta ctactgttac tgtttcttct ggaggcggcg gatctggcgg tggaggttct    1980
ggcggcggcg gatctcaagc tgttgttatt caagaatctg ctttgactac tcctccaggt    2040
gaaaccgtta ctttgacttg tggatcttct actggtgctg ttactgcttc taattatgct    2100
aattgggttc aagaaaaacc agatcattgc tttactggtt tgattggtgg tcataataat    2160
agaccaccag tgttccggc tagattttct ggttctttga ttggtgataa agctgctttg    2220
actattgctg gtactcaaac tgaagatgaa gctatttatt tttgtgcttt gtggtattct    2280
gatcattggg ttattggtgg tggtactaga ttgactgttt tgggctaata atctaga     2337
```

<210> SEQ ID NO 16
<211> LENGTH: 749
<212> TYPE: PRT
<213> ORGANISM: Artificial sequence
<220> FEATURE:
<223> OTHER INFORMATION: Synthetic

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys Ile Ser Gly Gly Gly
            100                 105                 110

Gly Ser Gly Gly Gly Gly Ser Gly Gly Gly Ser Gly Gly Gly Gly
        115                 120                 125

Ser Gly Gly Gly Gly Ser Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Phe Asp Phe Ser Arg Tyr Trp Met Ser Trp Val Arg Gln Ala Pro
                165                 170                 175

Gly Lys Gly Leu Glu Trp Ile Gly Glu Ile Asn Pro Asp Ser Ser Thr
            180                 185                 190

Ile Asn Tyr Ala Pro Ser Leu Lys Asp Lys Phe Ile Ile Ser Arg Asp
        195                 200                 205

Asn Ala Lys Asn Ser Leu Tyr Leu Gln Met Asn Ser Leu Arg Ala Glu
    210                 215                 220

Asp Thr Ala Val Tyr Tyr Cys Ala Arg Pro Asp Gly Asn Tyr Trp Tyr
225                 230                 235                 240

Phe Asp Val Trp Gly Gln Gly Thr Leu Val Thr Val Ser Ser Leu Glu
                245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
```

```
            275                 280                 285
Asp Thr Leu Met Ile Ser Arg Thr Pro Glu Val Thr Cys Val Val Val
            290                 295                 300
Asp Val Ser His Glu Asp Pro Glu Val Lys Phe Asn Trp Tyr Val Asp
305                 310                 315                 320
Gly Val Glu Val His Asn Ala Lys Thr Lys Pro Arg Glu Glu Gln Tyr
                325                 330                 335
Asn Ser Thr Tyr Arg Val Val Ser Val Leu Thr Val Leu His Gln Asp
                340                 345                 350
Trp Leu Asn Gly Lys Glu Tyr Lys Cys Lys Val Ser Asn Lys Ala Leu
            355                 360                 365
Pro Ala Pro Ile Glu Lys Thr Ile Ser Lys Ala Lys Gly Gln Pro Arg
370                 375                 380
Glu Pro Gln Val Tyr Thr Leu Pro Pro Ser Arg Asp Glu Leu Thr Lys
385                 390                 395                 400
Asn Gln Val Ser Leu Thr Cys Leu Val Lys Gly Phe Tyr Pro Ser Asp
                405                 410                 415
Ile Ala Val Glu Trp Glu Ser Asn Gly Gln Pro Glu Asn Asn Tyr Lys
            420                 425                 430
Thr Thr Pro Pro Val Leu Asp Ser Asp Gly Ser Phe Phe Leu Tyr Ser
            435                 440                 445
Lys Leu Thr Val Asp Lys Ser Arg Trp Gln Gln Gly Asn Val Phe Ser
450                 455                 460
Cys Ser Val Met His Glu Gly Leu His Asn His Tyr Thr Gln Lys Ser
465                 470                 475                 480
Leu Ser Leu Ser Pro Gly Lys Val Asp Gly Ala Ser Ser His Val Asn
                485                 490                 495
Val Ser Ser Pro Ser Val Gln Asp Ile His Val Lys Leu Gln Glu Ser
            500                 505                 510
Gly Pro Gly Leu Val Gln Pro Ser Gln Ser Leu Ser Leu Thr Cys Thr
            515                 520                 525
Val Ser Gly Phe Ser Leu Thr Asp Tyr Gly Val His Trp Val Arg Gln
530                 535                 540
Ser Pro Gly Lys Gly Leu Glu Trp Leu Gly Val Ile Trp Ser Gly Gly
545                 550                 555                 560
Gly Thr Ala Tyr Asn Thr Ala Leu Ile Ser Arg Leu Asn Ile Tyr Arg
                565                 570                 575
Asp Asn Ser Lys Asn Gln Val Phe Leu Glu Met Asn Ser Leu Gln Ala
            580                 585                 590
Glu Asp Thr Ala Met Tyr Tyr Cys Ala Arg Arg Gly Ser Tyr Pro Tyr
            595                 600                 605
Asn Tyr Phe Asp Ala Trp Gly Cys Gly Thr Thr Val Thr Val Ser Ser
            610                 615                 620
Gly Gly Gly Gly Ser Gly Gly Gly Ser Gly Gly Gly Gly Ser Gln
625                 630                 635                 640
Ala Val Val Ile Gln Glu Ser Ala Leu Thr Thr Pro Gly Glu Thr
                645                 650                 655
Val Thr Leu Thr Cys Gly Ser Ser Thr Gly Ala Val Thr Ala Ser Asn
                660                 665                 670
Tyr Ala Asn Trp Val Gln Glu Lys Pro Asp His Cys Phe Thr Gly Leu
            675                 680                 685
Ile Gly Gly His Asn Asn Arg Pro Pro Gly Val Pro Ala Arg Phe Ser
            690                 695                 700
```

```
Gly Ser Leu Ile Gly Asp Lys Ala Ala Leu Thr Ile Ala Gly Thr Gln
705                 710                 715                 720

Thr Glu Asp Glu Ala Ile Tyr Phe Cys Ala Leu Trp Tyr Ser Asp His
            725                 730                 735

Trp Val Ile Gly Gly Gly Thr Arg Leu Thr Val Leu Gly
            740                 745
```

<210> SEQ ID NO 17
<211> LENGTH: 2340
<212> TYPE: DNA
<213> ORGANISM: Artificial sequence
<220> FEATURE:
<223> OTHER INFORMATION: Synthetic

<400> SEQUENCE: 17

```
aagcttgccg ccatggagac agacacactc ctgctatggg tgctgctgct ctgggttcca      60
ggttccacag gtgacatcgt gatgacccag tctccaaaaa tcatgcctgt cagtcttgga     120
gatcaagcct ccatctcttg cagatctagt cagagccttg tacacagtaa tggaaacacc     180
tatttacatt ggtacctgca gaagccaggc cagtctccaa agctcctgat ctacaaagtt     240
tccaaccgat tttctggggt cccagacagg ttcagtggca gtggatcagg acagatttc      300 acactcaaga tcagcagagt ggaggctgag gatctgggag tttatttctg ctctcaaagt     360
acacatgttc cgtacacgtt cggaggggg accaagctgg aaataaagat ctctggtggc      420
ggtggctcgg gcggtggtgg gtcgggtggc ggcggctcgg gtggtggtgg gtcgggcggc     480
ggcggctcta gcgaggtgaa gctgcaggag tcacacactg gcctggtgaa ccttctcag      540 tctctgtccc tcacctgcac tgtcactggc tactcaatca ccagtgatta tgcctggaac     600
tggatccggc actttccagg aaacaaactg gagtggatgg gctacataag ctacagtggt     660
agcactagct acaacccatc tctcaaaagt cgaatctcta tcactcgaga cacatccaag     720
aaccagttct tcctgcagtt gaattctgtg actactgagg acacagccac atattactgt     780
gcaagagatg gttactacac ctttgctttc tggggccaag ggactctggt cactgtctct     840
tctctcgagc ccaaatcttc tgacaaaact cacacatgtc caccgtgccc agcacctgaa     900
ctcctggggg gaccgtcagt cttcctcttc ccccccaaaac ccaaggacac cctcatgatc     960
tcccggaccc ctgaggtcac atgcgtggtg gtggacgtga gccacgaaga ccctgaggtc    1020
aagttcaact ggtacgtgga cggcgtggag gtgcataatg ccaagacaaa gccgcgggag    1080
gagcagtaca acagcacgta ccgtgtggtc agcgtcctca ccgtcctgca ccaggactgg    1140
ctgaatggca aggagtacaa gtgcaaggtc tccaacaaag ccctcccagc ccccatcgag    1200
aaaaccatct ccaaagccaa agggcagccc cgagaaccac aggtgtacac cctgccccca    1260
tcccgggatg agctgaccaa gaaccaggtc agcctgacct gcctggtcaa aggcttctat    1320
cccagcgaca tcgccgtgga gtgggagagc aatgggcagc cggagaacaa ctacaagacc    1380
acgcctcccg tgctggactc cgacggctcc ttcttcctct acagcaagct caccgtggac    1440
aagagcaggt ggcagcaggg gaacgtcttc tcatgctccg tgatgcatga gggtctgcac    1500
aaccactaca cgcagaagag cctctctctg tctccgggta aagtcgacgg tgctagcagc    1560
catgtgaatg tgagcagccc tagcgtgcag gatatccacg ttaagttgca agaatctggt    1620
ccaggtttgg ttcagccatc tcaatctttg tctcttactt gtactgtttc tggtttctct    1680
ttgactgatt atggtgttca ttgggttaga caatctccag gtaaaggttt ggaatggttg    1740
ggtgttattt ggtctggtgg aggtactgct tataatactg ctttgatttc taggttgaat    1800
```

```
atttatcgag ataattctaa aaatcaagtt tttcttgaaa tgaattcttt gcaagctgaa   1860
gatactgcta tgtattattg tgctagaaga ggttcttatc catataatta ttttgatgct   1920
tggggttgtg gtactactgt tactgtttct tctggaggcg gcggatctgg cggtggaggt   1980
tctggcggcg gcggatctca agctgttgtt attcaagaat ctgctttgac tactcctcca   2040
ggtgaaaccg ttactttgac ttgtggatct tctactggtg ctgttactgc ttctaattat   2100
gctaattggg ttcaagaaaa accagatcat tgctttactg gtttgattgg tggtcataat   2160
aatagaccac caggtgttcc ggctagattt tctggttctt tgattggtga taaagctgct   2220
ttgactattg ctggtactca aactgaagat gaagctattt atttttgtgc tttgtggtat   2280
tctgatcatt gggttattgg tggtggtact agattgactg ttttgggcta ataatctaga   2340
```

<210> SEQ ID NO 18
<211> LENGTH: 752
<212> TYPE: PRT
<213> ORGANISM: Artificial sequence
<220> FEATURE:
<223> OTHER INFORMATION: Synthetic

<400> SEQUENCE: 18

```
Asp Ile Val Met Thr Gln Ser Pro Lys Ile Met Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Ile Ser Gly Gly Gly Gly Ser Gly Gly Gly Gly Ser Gly Gly Gly Gly
        115                 120                 125

Ser Gly Gly Gly Gly Ser Gly Gly Gly Gly Ser Glu Val Lys Leu
    130                 135                 140

Gln Glu Ser His Thr Gly Leu Val Lys Pro Ser Gln Ser Leu Ser Leu
145                 150                 155                 160

Thr Cys Thr Val Thr Gly Tyr Ser Ile Thr Ser Asp Tyr Ala Trp Asn
                165                 170                 175

Trp Ile Arg His Phe Pro Gly Asn Lys Leu Glu Trp Met Gly Tyr Ile
            180                 185                 190

Ser Tyr Ser Gly Ser Thr Ser Tyr Asn Pro Ser Leu Lys Ser Arg Ile
        195                 200                 205

Ser Ile Thr Arg Asp Thr Ser Lys Asn Gln Phe Phe Leu Gln Leu Asn
    210                 215                 220

Ser Val Thr Thr Glu Asp Thr Ala Thr Tyr Tyr Cys Ala Arg Asp Gly
225                 230                 235                 240

Tyr Tyr Thr Phe Ala Phe Trp Gly Gln Gly Thr Leu Val Thr Val Ser
                245                 250                 255

Ser Leu Glu Pro Lys Ser Ser Asp Lys Thr His Thr Cys Pro Pro Cys
            260                 265                 270
```

```
Pro Ala Pro Glu Leu Leu Gly Gly Pro Ser Val Phe Leu Phe Pro Pro
            275                 280                 285

Lys Pro Lys Asp Thr Leu Met Ile Ser Arg Thr Pro Glu Val Thr Cys
            290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
                340                 345                 350

His Gln Asp Trp Leu Asn Gly Lys Glu Tyr Lys Cys Lys Val Ser Asn
            355                 360                 365

Lys Ala Leu Pro Ala Pro Ile Glu Lys Thr Ile Ser Lys Ala Lys Gly
            370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
            435                 440                 445

Leu Tyr Ser Lys Leu Thr Val Asp Lys Ser Arg Trp Gln Gln Gly Asn
            450                 455                 460

Val Phe Ser Cys Ser Val Met His Glu Gly Leu His Asn His Tyr Thr
465                 470                 475                 480

Gln Lys Ser Leu Ser Leu Ser Pro Gly Lys Val Asp Gly Ala Ser Ser
                485                 490                 495

His Val Asn Val Ser Ser Pro Ser Val Gln Asp Ile His Val Lys Leu
            500                 505                 510

Gln Glu Ser Gly Pro Gly Leu Val Gln Pro Ser Gln Ser Leu Ser Leu
            515                 520                 525

Thr Cys Thr Val Ser Gly Phe Ser Leu Thr Asp Tyr Gly Val His Trp
            530                 535                 540

Val Arg Gln Ser Pro Gly Lys Gly Leu Glu Trp Leu Gly Val Ile Trp
545                 550                 555                 560

Ser Gly Gly Gly Thr Ala Tyr Asn Thr Ala Leu Ile Ser Arg Leu Asn
                565                 570                 575

Ile Tyr Arg Asp Asn Ser Lys Asn Gln Val Phe Leu Glu Met Asn Ser
            580                 585                 590

Leu Gln Ala Glu Asp Thr Ala Met Tyr Tyr Cys Ala Arg Arg Gly Ser
            595                 600                 605

Tyr Pro Tyr Asn Tyr Phe Asp Ala Trp Gly Cys Gly Thr Thr Val Thr
            610                 615                 620

Val Ser Ser Gly Gly Gly Gly Ser Gly Gly Gly Gly Ser Gly Gly Gly
625                 630                 635                 640

Gly Ser Gln Ala Val Val Ile Gln Glu Ser Ala Leu Thr Thr Pro Pro
                645                 650                 655

Gly Glu Thr Val Thr Leu Thr Cys Gly Ser Ser Thr Gly Ala Val Thr
            660                 665                 670

Ala Ser Asn Tyr Ala Asn Trp Val Gln Glu Lys Pro Asp His Cys Phe
            675                 680                 685
```

Thr Gly Leu Ile Gly Gly His Asn Asn Arg Pro Pro Gly Val Pro Ala
        690                 695                 700

Arg Phe Ser Gly Ser Leu Ile Gly Asp Lys Ala Ala Leu Thr Ile Ala
705                 710                 715                 720

Gly Thr Gln Thr Glu Asp Glu Ala Ile Tyr Phe Cys Ala Leu Trp Tyr
                    725                 730                 735

Ser Asp His Trp Val Ile Gly Gly Thr Arg Leu Thr Val Leu Gly
                740                 745                 750

<210> SEQ ID NO 19
<211> LENGTH: 243
<212> TYPE: PRT
<213> ORGANISM: Artificial sequence
<220> FEATURE:
<223> OTHER INFORMATION: Synthetic

<400> SEQUENCE: 19

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Gly Gly Gly Ser Gly Gly Gly Ser Gly
        115                 120                 125

Gly Gly Gly Ser Asp Ile Val Leu Thr Gln Ser Pro Pro Ser Leu Ala
130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile His Trp Tyr Gln Gln Lys Pro
                165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
        195                 200                 205

Leu Thr Ile Asp Pro Val Glu Glu Asp Val Ala Val Tyr Tyr Cys
    210                 215                 220

Leu Gln Ser Arg Thr Ile Pro Arg Thr Phe Gly Gly Gly Thr Lys Leu
225                 230                 235                 240

Glu Ile Lys

<210> SEQ ID NO 20
<211> LENGTH: 244
<212> TYPE: PRT
<213> ORGANISM: Artificial sequence
<220> FEATURE:
<223> OTHER INFORMATION: Synthetic

<400> SEQUENCE: 20

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
            35                  40                  45

Gly Val Ile Trp Ser Gly Gly Thr Ala Thr Tyr Ala Ala Phe Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Asn Asp Thr Ala Met Tyr Tyr Cys Ala
                85                  90                  95

Arg Arg Gly Ser Tyr Pro Tyr Asn Tyr Phe Asp Val Trp Gly Gln Gly
            100                 105                 110

Thr Thr Val Thr Val Ser Ser Gly Gly Gly Ser Gly Gly Gly Gly
            115                 120                 125

Ser Gly Gly Gly Ser Gln Ala Val Val Thr Gln Glu Ser Ala Leu
    130                 135                 140

Thr Thr Ser Pro Gly Glu Thr Val Thr Leu Thr Cys Arg Ser Ser Thr
145                 150                 155                 160

Gly Ala Val Thr Thr Ser Asn Tyr Ala Asn Trp Val Gln Glu Lys Pro
            165                 170                 175

Asp His Leu Phe Thr Gly Leu Ile Gly Gly Asn Asn Arg Pro Pro
            180                 185                 190

Gly Val Pro Ala Arg Phe Ser Gly Ser Leu Ile Gly Asp Lys Ala Ala
            195                 200                 205

Leu Thr Ile Ala Gly Thr Gln Thr Glu Ala Asp Ala Ile Tyr Phe Cys
    210                 215                 220

Ala Leu Trp Tyr Ser Asn His Trp Val Phe Gly Gly Phe Arg Gly
225                 230                 235                 240

Arg Val Leu Gly

<210> SEQ ID NO 21
<211> LENGTH: 244
<212> TYPE: PRT
<213> ORGANISM: Artificial sequence
<220> FEATURE:
<223> OTHER INFORMATION: Synthetic

<400> SEQUENCE: 21

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
            35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Gly Gly Gly Gly Ser Gly Gly Gly Gly
```

```
            115                 120                 125
Ser Gly Gly Gly Ser Gln Ala Val Val Ile Gln Glu Ser Ala Leu
        130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Thr Arg Leu
225                 230                 235                 240

Thr Val Leu Gly

<210> SEQ ID NO 22
<211> LENGTH: 229
<212> TYPE: PRT
<213> ORGANISM: Artificial sequence
<220> FEATURE:
<223> OTHER INFORMATION: Synthetic

<400> SEQUENCE: 22

Leu Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Arg Gly
            100                 105                 110

Thr Thr Val Thr Val Ser Ser Glu Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Leu
    210                 215                 220

Cys Phe Val Val Phe
225
```

```
<210> SEQ ID NO 23
<211> LENGTH: 244
<212> TYPE: PRT
<213> ORGANISM: Artificial sequence
<220> FEATURE:
<223> OTHER INFORMATION: Synthetic

<400> SEQUENCE: 23

Gln Ala Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65              70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145             150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225             230                 235                 240

Thr Val Leu Gly

<210> SEQ ID NO 24
<211> LENGTH: 244
<212> TYPE: PRT
<213> ORGANISM: Artificial sequence
<220> FEATURE:
<223> OTHER INFORMATION: Synthetic

<400> SEQUENCE: 24

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60
```

```
Ser Arg Leu Asn Ile Tyr Arg Asp Asn Ser Lys Asn Gln Val Phe Leu
 65                  70                  75                  80

Glu Met Asn Ser Leu Gln Ala Asp Asp Thr Ala Met Tyr Tyr Cys Ala
                 85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Pro Gly Gly Gly Gly Gly
            115                 120                 125

Ser Gly Gly Gly Ser Gln Ala Val Val Ile Gln Glu Ser Ala Leu
130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
            165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
            195                 200                 205

Leu Thr Ile Ala Gly Thr Gln Thr Glu Asp Glu Ala Ile Tyr Phe Cys
210                 215                 220

Ala Leu Trp Tyr Ser Asp His Trp Val Ile Gly Gly Thr Arg Leu
225                 230                 235                 240

Thr Val Leu Ser

<210> SEQ ID NO 25
<211> LENGTH: 244
<212> TYPE: PRT
<213> ORGANISM: Artificial sequence
<220> FEATURE:
<223> OTHER INFORMATION: Synthetic

<400> SEQUENCE: 25

His Val Lys Leu Gln Glu Ser Gly Pro Gly Leu Val Gln Pro Ser Gln
  1               5                  10                  15

Ser Leu Ser Leu Thr Cys Thr Val Ser Gly Phe Ser Leu Thr Asp Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Thr Ala Tyr Asn Thr Ala Leu Ile
         50                  55                  60

Ser Arg Leu Asn Ile Tyr Arg Asp Asn Ser Lys Asn Gln Val Phe Leu
 65                  70                  75                  80

Glu Met Asn Ser Leu Gln Ala Glu Asp Thr Ala Met Tyr Tyr Cys Ala
                 85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Ser Gly Gly Gly Gly
            115                 120                 125

Ser Gly Gly Gly Ser Gln Ala Val Val Ile Gln Glu Ser Ala Leu
130                 135                 140

Thr Thr Pro Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
            165                 170                 175
```

```
Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
        210                 215                 220

Ala Leu Trp Tyr Ser Asp His Trp Val Ile Gly Gly Thr Arg Leu
225                 230                 235                 240

Thr Val Leu Gly

<210> SEQ ID NO 26
<211> LENGTH: 244
<212> TYPE: PRT
<213> ORGANISM: Artificial sequence
<220> FEATURE:
<223> OTHER INFORMATION: Synthetic

<400> SEQUENCE: 26

Gln Val Lys Leu Gln Glu Ser Gly Pro Gly Leu Val Arg Pro Ser Gln
1               5                   10                  15

Pro Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Ser Gly Gly Gly Gly
        115                 120                 125

Ser Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Phe Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
        210                 215                 220

Ala Leu Trp Tyr Ser Asp His Trp Val Ile Gly Gly Thr Arg Leu
225                 230                 235                 240

Thr Val Leu Gly

<210> SEQ ID NO 27
<211> LENGTH: 244
<212> TYPE: PRT
<213> ORGANISM: Artificial sequence
<220> FEATURE:
<223> OTHER INFORMATION: Synthetic
```

```
<400> SEQUENCE: 27

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
                100                 105                 110

Thr Thr Val Thr Val Ser Ser Gly Gly Gly Ser Gly Gly Gly Gly
                115                 120                 125

Ser Gly Gly Gly Gly Ser Gln Ala Val Val Ile Gln Glu Ser Ala Leu
        130                 135                 140

Ile Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
                180                 185                 190

Gly Val Pro Ala Arg Phe Ser Gly Ser Leu Ile Gly Asp Lys Ala Ala
            195                 200                 205

Leu Thr Ile Ala Gly Thr Gln Thr Gly Asp Glu Ala Ile Tyr Phe Cys
    210                 215                 220

Ala Leu Trp Tyr Ser Asp His Trp Val Ile Gly Gly Thr Arg Leu
225                 230                 235                 240

Thr Val Leu Gly

<210> SEQ ID NO 28
<211> LENGTH: 244
<212> TYPE: PRT
<213> ORGANISM: Artificial sequence
<220> FEATURE:
<223> OTHER INFORMATION: Synthetic

<400> SEQUENCE: 28

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
                100                 105                 110
```

```
Thr Thr Val Thr Val Ser Ser Gly Gly Gly Ser Gly Gly Gly
        115                 120                 125

Ser Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Thr Arg Leu
225                 230                 235                 240

Thr Val Leu Gly

<210> SEQ ID NO 29
<211> LENGTH: 244
<212> TYPE: PRT
<213> ORGANISM: Artificial sequence
<220> FEATURE:
<223> OTHER INFORMATION: Synthetic

<400> SEQUENCE: 29

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Ser Gly Gly Gly
        115                 120                 125

Ser Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220
```

Ala Leu Trp Tyr Ser Asp His Trp Val Ile Gly Gly Thr Arg Leu
225                 230                 235                 240

Thr Val Leu Gly

<210> SEQ ID NO 30
<211> LENGTH: 244
<212> TYPE: PRT
<213> ORGANISM: Artificial sequence
<220> FEATURE:
<223> OTHER INFORMATION: Synthetic

<400> SEQUENCE: 30

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Ser Gly Ser Gly Gly
        115                 120                 125

Ser Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Thr Arg Leu
225                 230                 235                 240

Thr Val Leu Gly

<210> SEQ ID NO 31
<211> LENGTH: 244
<212> TYPE: PRT
<213> ORGANISM: Artificial sequence
<220> FEATURE:
<223> OTHER INFORMATION: Synthetic

<400> SEQUENCE: 31

Gln Val Lys Leu Gln Glu Ser Gly Pro Gly Leu Val Gln Pro Pro Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu

```
                35                  40                  45
Gly Val Ile Trp Ser Gly Gly Thr Ala Tyr Asn Thr Ala Leu Ile
 50                  55                  60

Ser Arg Leu Asn Ile Tyr Arg Asp Asn Ser Lys Asn Gln Val Phe Phe
 65                  70                  75                  80

Glu Met Asn Ser Leu Gln Ala Asp Asp Thr Ala Met Tyr Tyr Cys Ala
                 85                  90                  95

Arg Arg Gly Ser Tyr Pro Tyr Asn Tyr Phe Asp Ala Trp Gly Cys Gly
                100                 105                 110

Thr Thr Val Thr Val Ser Ser Gly Gly Gly Ser Gly Gly Gly Gly
                115                 120                 125

Ser Gly Gly Gly Gly Ser Gln Ala Val Val Ile Gln Glu Ser Ala Leu
130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
                180                 185                 190

Gly Val Pro Ala Arg Phe Ser Gly Ser Leu Ile Gly Asp Lys Ala Thr
                195                 200                 205

Leu Thr Ile Ala Gly Thr Gln Thr Glu Asp Glu Ala Ile Tyr Phe Cys
210                 215                 220

Ala Leu Trp Tyr Ser Asp His Trp Val Ile Gly Gly Thr Arg Leu
225                 230                 235                 240

Thr Val Leu Gly

<210> SEQ ID NO 32
<211> LENGTH: 244
<212> TYPE: PRT
<213> ORGANISM: Artificial sequence
<220> FEATURE:
<223> OTHER INFORMATION: Synthetic

<400> SEQUENCE: 32

Gln Val Lys Leu Gln Glu Ser Gly Pro Gly Leu Val Gln Pro Ser Gln
 1               5                  10                  15

Ser Leu Ser Ile Thr Cys Thr Val Ser Gly Phe Ser Leu Thr Asp Tyr
                20                  25                  30

Gly Val His Trp Val Arg Gln Ser Pro Gly Lys Gly Leu Glu Trp Leu
                35                  40                  45

Gly Val Ile Trp Ser Gly Gly Thr Ala Tyr Asn Thr Ala Leu Ile
 50                  55                  60

Ser Arg Leu Asn Ile Tyr Arg Asp Asn Ser Lys Asn Gln Val Phe Phe
 65                  70                  75                  80

Glu Met Asn Ser Leu Gln Ala Glu Asp Thr Ala Met Tyr Tyr Cys Ala
                 85                  90                  95

Arg Arg Gly Ser Tyr Pro Tyr Asn Tyr Phe Asp Ala Trp Gly Cys Gly
                100                 105                 110

Thr Thr Val Thr Val Ser Ser Gly Gly Gly Pro Gly Gly Gly
                115                 120                 125

Ser Gly Gly Gly Gly Ser Gln Ala Val Val Ile Gln Glu Ser Ala Leu
130                 135                 140

Thr Thr Ser Pro Gly Glu Thr Val Thr Leu Thr Cys Gly Ser Ser Thr
145                 150                 155                 160
```

```
Gly Ala Ile Thr Thr Ser Asn Tyr Ala Asn Trp Val Gln Glu Lys Pro
            165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
            195                 200                 205

Leu Thr Ile Ala Gly Thr Gln Thr Glu Asp Glu Ala Ile Tyr Phe Cys
            210                 215                 220

Ala Leu Trp Tyr Ser Asp His Trp Val Ile Gly Gly Thr Arg Leu
225                 230                 235                 240

Thr Val Leu Gly

<210> SEQ ID NO 33
<211> LENGTH: 244
<212> TYPE: PRT
<213> ORGANISM: Artificial sequence
<220> FEATURE:
<223> OTHER INFORMATION: Synthetic

<400> SEQUENCE: 33

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Glu Asp Thr Ala Met Tyr Tyr Cys Ala
                85                  90                  95

Arg Arg Gly Ser Tyr Pro Tyr Asn Tyr Phe Asp Ala Trp Gly Cys Gly
            100                 105                 110

Thr Thr Val Thr Val Ser Ser Gly Gly Gly Ser Gly Gly Gly Gly
            115                 120                 125

Ser Gly Gly Gly Gly Ser Gln Ala Val Val Gln Glu Ser Ala Leu
        130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
            165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
            195                 200                 205

Leu Thr Ile Val Gly Thr Gln Thr Glu Asp Glu Ala Ile Tyr Phe Cys
            210                 215                 220

Ala Leu Trp Tyr Ser Asp His Trp Val Ile Gly Gly Thr Arg Leu
225                 230                 235                 240

Thr Val Leu Gly

<210> SEQ ID NO 34
<211> LENGTH: 244
<212> TYPE: PRT
```

<213> ORGANISM: Artificial sequence
<220> FEATURE:
<223> OTHER INFORMATION: Synthetic

<400> SEQUENCE: 34

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Gly Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Arg Asp Asn Ser Lys Asn Gln Val Phe Phe
65                  70                  75                  80

Glu Met Asn Ser Leu Gln Ala Asp Asp Thr Ala Met Tyr Tyr Cys Ala
                85                  90                  95

Arg Arg Gly Arg Tyr Pro Tyr Asn Tyr Phe Asp Ala Trp Gly Cys Gly
            100                 105                 110

Thr Thr Val Thr Val Ser Ser Gly Gly Gly Ser Gly Gly Gly Gly
        115                 120                 125

Ser Gly Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
            180                 185                 190

Gly Val Pro Ala Arg Phe Ser Gly Ser Leu Ile Gly Asp Lys Ala Ala
        195                 200                 205

Leu Thr Ile Ala Gly Thr Gln Thr Glu Asp Glu Ala Ile Tyr Phe Cys
    210                 215                 220

Ala Leu Trp Tyr Ser Asp His Trp Val Ile Gly Gly Gly Thr Arg Leu
225                 230                 235                 240

Thr Val Leu Gly
```

<210> SEQ ID NO 35
<211> LENGTH: 244
<212> TYPE: PRT
<213> ORGANISM: Artificial sequence
<220> FEATURE:
<223> OTHER INFORMATION: Synthetic

<400> SEQUENCE: 35

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Val Arg Gln Ser Pro Gly Lys Ser Leu Glu Trp Leu
        35                  40                  45

Gly Val Ile Trp Ser Gly Gly Gly Thr Ala Tyr Asn Thr Ala Leu Ile
    50                  55                  60

Ser Arg Leu Asn Ile Tyr Lys Asp Asn Ser Lys Asn Gln Val Phe Phe
65                  70                  75                  80

Glu Met Asn Ser Leu Gln Ala Glu Asp Thr Ala Met Tyr Tyr Cys Ala
```

```
                    85                  90                  95
Arg Arg Gly Ser Tyr Pro Tyr Asn Tyr Phe Asp Ala Trp Gly Cys Gly
                100                 105                 110

Thr Thr Val Thr Val Ser Ser Gly Gly Gly Ser Gly Gly Gly Gly
            115                 120                 125

Ser Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
                180                 185                 190

Gly Val Pro Ala Arg Phe Ser Gly Ser Leu Ile Gly Asp Lys Ala Ala
                195                 200                 205

Leu Thr Ile Ala Gly Thr Gln Thr Glu Asp Glu Ala Ile Tyr Tyr Cys
    210                 215                 220

Ala Leu Trp Tyr Ser Asp His Trp Val Ile Gly Gly Thr Arg Leu
225                 230                 235                 240

Thr Val Leu Gly

<210> SEQ ID NO 36
<211> LENGTH: 238
<212> TYPE: PRT
<213> ORGANISM: Artificial sequence
<220> FEATURE:
<223> OTHER INFORMATION: Synthetic

<400> SEQUENCE: 36

Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
                20                  25                  30

Gly Val His Trp Val Arg Gln Ser Pro Gly Lys Gly Leu Glu Trp Leu
            35                  40                  45

Gly Val Ile Trp Ser Gly Gly Thr Ala Tyr Asn Thr Ala Leu Ile
    50                  55                  60

Ser Arg Leu Asn Ile Tyr Arg Asp Asn Ser Lys Asn Gln Val Phe Leu
65                  70                  75                  80

Glu Met Asn Ser Leu Gln Ala Asp Asp Thr Ala Met Tyr Tyr Cys Ala
                85                  90                  95

Arg Arg Gly Ser Tyr Pro Tyr Asn Tyr Phe Asp Ala Trp Gly Arg Gly
                100                 105                 110

Thr Thr Val Thr Val Ser Ser Gly Gly Gly Ser Gly Gly Gly Gly
            115                 120                 125

Ser Gly Gly Gly Ser Gln Ala Val Val Ile Gln Glu Ser Ala Leu
    130                 135                 140

Thr Thr Ser Pro Gly Glu Thr Val Thr Leu Thr Cys Gly Ser Ser Thr
145                 150                 155                 160

Gly Ala Val Thr Ala Ser Asn Tyr Ala Asn Trp Val Gln Glu Lys Pro
                165                 170                 175

Asp His Cys Phe Thr Gly Leu Ile Gly Gly His Asn Asn Arg Pro Pro
                180                 185                 190

Gly Val Pro Ala Arg Phe Ser Gly Ser Leu Ile Gly Asp Lys Ala Ala
                195                 200                 205
```

Leu Thr Ile Ala Gly Thr Gln Thr Glu Asp Glu Ala Ile Tyr Phe Cys
            210                 215                 220

Ala Leu Trp Tyr Ser Asp His Trp Val Ile Gly Trp Trp Tyr
225                 230                 235

<210> SEQ ID NO 37
<211> LENGTH: 40
<212> TYPE: DNA
<213> ORGANISM: Artificial sequence
<220> FEATURE:
<223> OTHER INFORMATION: Synthetic

<400> SEQUENCE: 37
agacccaagc ttgccgccat ggattttcaa gtgcagattt                              40

<210> SEQ ID NO 38
<211> LENGTH: 36
<212> TYPE: DNA
<213> ORGANISM: Artificial sequence
<220> FEATURE:
<223> OTHER INFORMATION: Synthetic

<400> SEQUENCE: 38
tttgggctcg agtgaagaga cggtgaccat tgtccc                                  36

<210> SEQ ID NO 39
<211> LENGTH: 112
<212> TYPE: PRT
<213> ORGANISM: Artificial sequence
<220> FEATURE:
<223> OTHER INFORMATION: Synthetic

<400> SEQUENCE: 39

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

<210> SEQ ID NO 40
<211> LENGTH: 106
<212> TYPE: PRT
<213> ORGANISM: Artificial sequence
<220> FEATURE:
<223> OTHER INFORMATION: Synthetic

<400> SEQUENCE: 40

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr

```
                35                  40                  45
Ala Thr Ser Asn Leu Ala Ser Gly Val Pro Ala Arg Phe Ser Gly Ser
             50                  55                  60
Gly Ser Gly Thr Ser Tyr Ser Leu Thr Ile Ser Arg Val Glu Ala Glu
 65                  70                  75                  80
Asp Ala Ala Thr Tyr Tyr Cys Gln Gln Trp Ser Phe Asn Pro Pro Thr
                 85                  90                  95
Phe Gly Gly Gly Thr Lys Leu Glu Ile Lys
            100                 105

<210> SEQ ID NO 41
<211> LENGTH: 106
<212> TYPE: PRT
<213> ORGANISM: Artificial sequence
<220> FEATURE:
<223> OTHER INFORMATION: Synthetic

<400> SEQUENCE: 41

Asp Ile Val Leu Ser Gln Ser Pro Ala Ile Leu Ser Ala Ser Pro Gly
  1               5                  10                  15
Glu Lys Val Thr Met Thr Cys Arg Ala Ser Ser Ser Leu Ser Phe Met
                 20                  25                  30
His Trp Tyr Gln Gln Lys Pro Gly Ser Ser Pro Lys Pro Trp Ile Tyr
             35                  40                  45
Ala Thr Ser Asn Leu Ala Ser Gly Val Pro Ala Arg Phe Ser Gly Ser
         50                  55                  60
Gly Ser Gly Thr Ser Tyr Ser Leu Thr Ile Ser Arg Val Glu Ala Glu
 65                  70                  75                  80
Asp Ala Ala Thr Tyr Phe Cys His Gln Trp Ser Ser Asn Pro Leu Thr
                 85                  90                  95
Phe Gly Ala Gly Thr Lys Leu Glu Leu Lys
            100                 105

<210> SEQ ID NO 42
<211> LENGTH: 122
<212> TYPE: PRT
<213> ORGANISM: Artificial sequence
<220> FEATURE:
<223> OTHER INFORMATION: Synthetic

<400> SEQUENCE: 42

Glu Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Thr Ser Tyr
                 20                  25                  30
Trp Ile Gly Trp Val Arg Gln Met Pro Gly Lys Gly Leu Glu Trp Met
             35                  40                  45
Gly Ile Ile Tyr Pro Gly Asp Ser Asp Thr Arg Tyr Ser Pro Ser Phe
         50                  55                  60
Gln Gly Gln Val Thr Ile Ser Ala Asp Lys Ser Ile Thr Thr Ala Tyr
 65                  70                  75                  80
Leu Gln Trp Ser Ser Leu Lys Ala Ser Asp Thr Ala Met Tyr Tyr Cys
                 85                  90                  95
Ala Arg His Pro Ser Tyr Gly Ser Gly Ser Pro Asn Phe Asp Tyr Trp
            100                 105                 110
Gly Gln Gly Thr Leu Val Thr Val Ser Ser
            115                 120
```

<210> SEQ ID NO 43
<211> LENGTH: 128
<212> TYPE: PRT
<213> ORGANISM: Artificial sequence
<220> FEATURE:
<223> OTHER INFORMATION: Synthetic

<400> SEQUENCE: 43

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser Leu Asp Glu Ser Lys Tyr
        115                 120                 125
```

<210> SEQ ID NO 44
<211> LENGTH: 128
<212> TYPE: PRT
<213> ORGANISM: Artificial sequence
<220> FEATURE:
<223> OTHER INFORMATION: Synthetic

<400> SEQUENCE: 44

```
Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Thr Leu Thr Val Ser Ser Leu Asp Pro Lys Ser Ser
        115                 120                 125
```

<210> SEQ ID NO 45
<211> LENGTH: 747
<212> TYPE: DNA
<213> ORGANISM: Artificial sequence
<220> FEATURE:
<223> OTHER INFORMATION: Synthetic

<400> SEQUENCE: 45

```
gacattgtga tgactcagac accactgagc tccccagtga ctctgggaca gccagccagt    60
```

```
atctcatgca gatctagtca gtcactggtc tacagcgacg gcaacaccta tctgagctgg    120
ctgcagcagc gaccaggaca gccacctaga ctgctgatct acaagatttc aataggttc    180 tctggagtgc ccgaccgctt tagcggatcc ggagctggaa ctgatttcac cctgaaaatc    240
tcccgcgtgg aggctgaaga tgtgggcgtc tactattgcg tccaggcaac ccagttccct    300
ctgacatttg gcgggggaac taaggtggag atcaagggag gaggaggatc tggaggagga    360
ggaagtggag gaggaggatc cgaagtgcag ctggtccagt ctggggccga ggtgaagaaa    420
cctggagaaa gtctgaagat ctcatgtaaa ggctccgggt actctttcac aagttattgg    480
attggctggg tccgacagat gccaggaaag ggcctgagt ggatgggaat catctacccc    540
ggcgacagcg atacccggta ttctcctagt tttcagggcc aggtgacaat cagcgcagac    600
aagtccatta ccacagccta tctgcagtgg tcaagcctga agcctctga taccgctatg    660 tactattgtg ccaggcaccc tagctacggg tcaggaagcc caaactttga ctattgggc    720 caggggacac tggtgactgt ctcctct                                        747

<210> SEQ ID NO 46
<211> LENGTH: 756
<212> TYPE: DNA
<213> ORGANISM: Artificial sequence
<220> FEATURE:
<223> OTHER INFORMATION: Synthetic

<400> SEQUENCE: 46
gacattgtgc tgacccaatc tccagctatc ctgtctgcat ctccagggga gaaggtcaca     60
atgacttgca gggccagctc aagtgtaaat tacatggact ggtaccagaa gaagccagga    120
tcctccccca aaccctggat ttatgccaca tccaacctgg cttctggagt ccctgctcgc    180
ttcagtggca gtgggtctgg gacctcttac tctctcacaa tcagcagagt ggaggctgaa    240
gatgctgcca cttattactg ccagcagtgg agttttaatc cacccacgtt cggagggggg    300
accaagctgg aaataaaagg cagtactagc ggtggtggct ccggggggcgg ttccggtggg    360 ggcggcagca gcgaggtgca gctgcagcag tctggggctg agctggtgaa gcctggggcc    420
tcagtgaaga tgtcctgcaa ggcttctggc tacacattta ccagttacaa tatgcactgg    480
gtaaagcaga cacctggaca gggcctggaa tggattggag ctatttatcc aggaaatggt    540
gatacttcct acaatcagaa gttcaaaggc aaggccacat tgactgcaga caaatcctcc    600
agcacagcct acatgcagct cagcagcctg acatctgagg actctgcgga ctattactgt    660
gcaagatcta attattacgg tagtagctac tggttcttcg atgtctgggg cgcagggacc    720
acggtcaccg tctcctcact cgacgaatct aagtac                              756

<210> SEQ ID NO 47
<211> LENGTH: 738
<212> TYPE: DNA
<213> ORGANISM: Artificial sequence
<220> FEATURE:
<223> OTHER INFORMATION: Synthetic

<400> SEQUENCE: 47
gacattgttc tctcccagtc tccagcaatc ctttctgcat ctccagggga gaaggtcaca     60
atgacttgca gggccagctc aagtttaagt ttcatgcact ggtaccagca gaagccagga    120
tcctccccca aaccctggat ttatgccaca tccaacctgg cttctggagt ccctgctcgc    180
ttcagtggca gtgggtctgg gacctcttac tctctcacaa tcagcagagt ggaggctgaa    240
```

```
gatgctgcca cttatttctg ccatcagtgg agtagtaacc cgctcacgtt cggtgctggg    300
accaagctgg agctgaaggg cagtactagc ggtggtggct ccggggggcgg ttccggtggg    360 ggcggcagca gccaggtgca actgcggcag cctggggctg agctggtgaa gcctggggcc    420
tcagtgaaga tgtcctgcaa ggcttctggc tacacattta ccagttacaa tatgcactgg    480
gtaaagcaga cacctggaca gggcctggaa tggattggag ctatttatcc aggaaatggt    540
gatacttcct acaatcagaa gttcaaaggc aaggccacat tgactgcaga caaatcctcc    600
agcacagcct acatgcagct cagcagtctg acatctgagg actctgcggt ctattactgt    660
gcaagatcgc actacggtag taactacgta gactactttg actactgggg ccaaggcacc    720
actctcacag tctcctca                                                   738

<210> SEQ ID NO 48
<211> LENGTH: 336
<212> TYPE: DNA
<213> ORGANISM: Artificial sequence
<220> FEATURE:
<223> OTHER INFORMATION: Synthetic

<400> SEQUENCE: 48
gacattgtga tgactcagac accactgagc tccccagtga ctctgggaca gccagccagt     60
atctcatgca gatctagtca gtcactggtc tacagcgacg gcaacaccta tctgagctgg    120
ctgcagcagc gaccaggaca gccacctaga ctgctgatct acaagatttc caataggttc    180
tctggagtgc ccgaccgctt tagcggatcc ggagctggaa ctgatttcac cctgaaaatc    240
tcccgcgtgg aggctgaaga tgtgggcgtc tactattgcg tccaggcaac ccagttccct    300
ctgacatttg gcgggggaac taaggtggag atcaag                              336

<210> SEQ ID NO 49
<211> LENGTH: 318
<212> TYPE: DNA
<213> ORGANISM: Artificial sequence
<220> FEATURE:
<223> OTHER INFORMATION: Synthetic

<400> SEQUENCE: 49
gacattgtgc tgacccaatc tccagctatc ctgtctgcat ctccagggga aaggtcaca      60 atgacttgca gggccagctc aagtgtaaat tacatggact ggtaccagaa gaagccagga   120
tcctccccca aaccctggat ttatgccaca tccaacctgg cttctggagt ccctgctcgc   180
ttcagtggca gtgggtctgg gacctcttac tctctcacaa tcagcagagt ggaggctgaa   240
gatgctgcca cttattactg ccagcagtgg agttttaatc cacccacgtt cggaggggggg   300 accaagctgg aaataaaa                                                  318

<210> SEQ ID NO 50
<211> LENGTH: 318
<212> TYPE: DNA
<213> ORGANISM: Artificial sequence
<220> FEATURE:
<223> OTHER INFORMATION: Synthetic

<400> SEQUENCE: 50
gacattgttc tctcccagtc tccagcaatc ctttctgcat ctccagggga aaggtcaca      60 atgacttgca gggccagctc aagtttaagt ttcatgcact ggtaccagca gaagccagga   120
tcctccccca aaccctggat ttatgccaca tccaacctgg cttctggagt ccctgctcgc   180
ttcagtggca gtgggtctgg gacctcttac tctctcacaa tcagcagagt ggaggctgaa   240
```

```
gatgctgcca cttatttctg ccatcagtgg agtagtaacc cgctcacgtt cggtgctggg    300
accaagctgg agctgaag                                                 318

<210> SEQ ID NO 51
<211> LENGTH: 366
<212> TYPE: DNA
<213> ORGANISM: Artificial sequence
<220> FEATURE:
<223> OTHER INFORMATION: Synthetic

<400> SEQUENCE: 51
gaagtgcagc tggtccagtc tggggccgag gtgaagaaac ctggagaaag tctgaagatc    60
tcatgtaaag gctccgggta ctctttcaca agttattgga ttggctgggt ccgacagatg    120
ccaggaaagg gcctggagtg gatgggaatc atctaccccg gcgacagcga tacccggtat    180
tctcctagtt ttcagggcca ggtgacaatc agcgcagaca agtccattac cacagcctat    240
ctgcagtggt caagcctgaa agcctctgat accgctatgt actattgtgc caggcaccct    300
agctacgggt caggaagccc aaactttgac tattggggcc aggggacact ggtgactgtc    360
tcctct                                                              366

<210> SEQ ID NO 52
<211> LENGTH: 384
<212> TYPE: DNA
<213> ORGANISM: Artificial sequence
<220> FEATURE:
<223> OTHER INFORMATION: Synthetic

<400> SEQUENCE: 52
gaggtgcagc tgcagcagtc tggggctgag ctggtgaagc ctggggcctc agtgaagatg    60
tcctgcaagg cttctggcta cacatttacc agttacaata tgcactgggt aaagcagaca    120
cctggacagg gcctggaatg gattggagct atttatccag gaaatggtga tacttcctac    180
aatcagaagt tcaaaggcaa ggccacattg actgcagaca atcctccag cacagcctac    240 atgcagctca gcagcctgac atctgaggac tctgcggact attactgtgc aagatctaat    300
tattacggta gtagctactg gttcttcgat gtctggggcg cagggaccac ggtcaccgtc    360
tcctcactcg acgaatctaa gtac                                          384

<210> SEQ ID NO 53
<211> LENGTH: 366
<212> TYPE: DNA
<213> ORGANISM: Artificial sequence
<220> FEATURE:
<223> OTHER INFORMATION: Synthetic

<400> SEQUENCE: 53
caggtgcaac tgcggcagcc tggggctgag ctggtgaagc ctggggcctc agtgaagatg    60
tcctgcaagg cttctggcta cacatttacc agttacaata tgcactgggt aaagcagaca    120
cctggacagg gcctggaatg gattggagct atttatccag gaaatggtga tacttcctac    180
aatcagaagt tcaaaggcaa ggccacattg actgcagaca atcctccag cacagcctac    240 atgcagctca gcagtctgac atctgaggac tctgcggtct attactgtgc aagatcgcac    300
tacggtagta actacgtaga ctactttgac tactggggcc aaggcaccac tctcacagtc    360
tcctca                                                              366

<210> SEQ ID NO 54
```

<211> LENGTH: 449
<212> TYPE: PRT
<213> ORGANISM: Artificial sequence
<220> FEATURE:
<223> OTHER INFORMATION: Synthetic

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 55
<211> LENGTH: 214
<212> TYPE: PRT
<213> ORGANISM: Artificial sequence
<220> FEATURE:
<223> OTHER INFORMATION: Synthetic

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 249
<212> TYPE: PRT
<213> ORGANISM: Artificial sequence
<220> FEATURE:
<223> OTHER INFORMATION: Synthetic

<400> SEQUENCE: 56

Asp Ile Val Met Thr Gln Thr Pro Leu Ser Ser Pro Val Thr Leu Gly
1               5                   10                  15
```

```
Gln Pro Ala Ser Ile Ser Cys Arg Ser Ser Gln Ser Leu Val Tyr Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Val Gln Ala
                 85                  90                  95

Thr Gln Phe Pro Leu Thr Phe Gly Gly Gly Thr Lys Val Glu Ile Lys
             100                 105                 110

Gly Gly Gly Gly Ser Gly Gly Gly Ser Gly Gly Gly Gly Ser Glu
         115                 120                 125

Val Gln Leu Val Gln Ser Gly Ala Glu Val Lys Lys Pro Gly Glu Ser
130                 135                 140

Leu Lys Ile Ser Cys Lys Gly Ser Gly Tyr Ser Phe Thr Ser Tyr Trp
145                 150                 155                 160

Ile Gly Trp Val Arg Gln Met Pro Gly Lys Gly Leu Glu Trp Met Gly
                165                 170                 175

Ile Ile Tyr Pro Gly Asp Ser Asp Thr Arg Tyr Ser Pro Ser Phe Gln
            180                 185                 190

Gly Gln Val Thr Ile Ser Ala Asp Lys Ser Ile Thr Thr Ala Tyr Leu
        195                 200                 205

Gln Trp Ser Ser Leu Lys Ala Ser Asp Thr Ala Met Tyr Tyr Cys Ala
210                 215                 220

Arg His Pro Ser Tyr Gly Ser Gly Ser Pro Asn Phe Asp Tyr Trp Gly
225                 230                 235                 240

Gln Gly Thr Leu Val Thr Val Ser Ser
                245

<210> SEQ ID NO 57
<211> LENGTH: 252
<212> TYPE: PRT
<213> ORGANISM: Artificial sequence
<220> FEATURE:
<223> OTHER INFORMATION: Synthetic

<400> SEQUENCE: 57

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
             20                  25                  30

Asp Trp Tyr Gln Lys Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
     50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Gly Ser Thr Ser Gly Gly
            100                 105                 110

Gly Ser Gly Gly Gly Ser Gly Gly Gly Gly Ser Ser Glu Val Gln Leu
        115                 120                 125
```

Gln Gln Ser Gly Ala Glu Leu Val Lys Pro Gly Ala Ser Val Lys Met
        130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Thr Ala Tyr Met Gln Leu Ser
        195                 200                 205

Ser Leu Thr Ser Glu Asp Ser Ala Asp Tyr Tyr Cys Ala Arg Ser Asn
        210                 215                 220

Tyr Tyr Gly Ser Ser Tyr Trp Phe Phe Asp Val Trp Gly Ala Gly Thr
225                 230                 235                 240

Thr Val Thr Val Ser Ser Leu Asp Glu Ser Lys Tyr
                245                 250

<210> SEQ ID NO 58
<211> LENGTH: 252
<212> TYPE: PRT
<213> ORGANISM: Artificial sequence
<220> FEATURE:
<223> OTHER INFORMATION: Synthetic

<400> SEQUENCE: 58

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys Gly Ser Thr Ser Gly Gly
            100                 105                 110

Gly Ser Gly Gly Gly Ser Gly Gly Gly Ser Ser Gln Val Gln Leu
        115                 120                 125

Arg Gln Pro Gly Ala Glu Leu Val Lys Pro Gly Ala Ser Val Lys Met
        130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Thr Ala Tyr Met Gln Leu Ser
        195                 200                 205

Ser Leu Thr Ser Glu Asp Ser Ala Val Tyr Tyr Cys Ala Arg Ser His
        210                 215                 220

Tyr Gly Ser Asn Tyr Val Asp Tyr Phe Asp Tyr Trp Gly Gln Gly Thr
225                 230                 235                 240

```
Thr Leu Thr Val Ser Ser Leu Asp Pro Lys Ser Ser
            245                 250

<210> SEQ ID NO 59
<211> LENGTH: 120
<212> TYPE: PRT
<213> ORGANISM: Homo sapiens

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Arg Trp Arg Gly Tyr Lys Leu Asp Tyr Trp Gly Gln
            100                 105                 110

Gly Thr Leu Val Thr Val Ser Ser
        115                 120

<210> SEQ ID NO 60
<211> LENGTH: 123
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Lys Tyr Tyr Ala Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Phe Asp Phe Gly Arg Arg Ala Val Arg Leu Asp Tyr
            100                 105                 110

Trp Gly Gln Gly Thr Leu Val Thr Val Ser Ser
        115                 120

<210> SEQ ID NO 61
<211> LENGTH: 123
<212> TYPE: PRT
<213> ORGANISM: Homo sapiens

<400> SEQUENCE: 61

Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
            20                  25                  30

Phe Ile Gly Trp Val Arg Gln Met Pro Gly Lys Gly Leu Glu Trp Met
         35                  40                  45

Gly Ile Ile Tyr Pro Gly Lys Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Val Tyr Ser Phe Gly Gly Arg His Lys Ala Leu Phe Asp Tyr
            100                 105                 110

Trp Gly Gln Gly Thr Leu Val Thr Val Ser Ser
            115                 120
```

<210> SEQ ID NO 62
<211> LENGTH: 118
<212> TYPE: PRT
<213> ORGANISM: Homo sapiens

<400> SEQUENCE: 62

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
         35                  40                  45

Gly Leu Ile Asn Pro Tyr Asn Ser Asp Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg Val Ala Leu Arg Val Ala Leu Asp Tyr Trp Gly Gln Gly Thr
            100                 105                 110

Leu Val Thr Val Ser Ser
            115
```

<210> SEQ ID NO 63
<211> LENGTH: 119
<212> TYPE: PRT
<213> ORGANISM: Homo sapiens

<400> SEQUENCE: 63

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
         35                  40                  45

Ser Ala Ile Lys Tyr Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

```
Ala Lys Arg Ala Glu Ser Gly Pro Gly Leu Asp Tyr Trp Gly Gln Gly
            100                 105                 110

Thr Leu Val Thr Val Ser Ser
            115

<210> SEQ ID NO 64
<211> LENGTH: 123
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Trp Asp Phe Gly Arg Arg Ala Val Arg Leu Asp Tyr
            100                 105                 110

Trp Gly Gln Gly Thr Leu Val Thr Val Ser Ser
        115                 120

<210> SEQ ID NO 65
<211> LENGTH: 122
<212> TYPE: PRT
<213> ORGANISM: Homo sapiens

<400> SEQUENCE: 65

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Gly Phe Tyr Gly Arg Ser Phe Arg Ile Phe Asp Tyr Trp
            100                 105                 110

Gly Gln Gly Thr Leu Val Thr Val Ser Ser
        115                 120

<210> SEQ ID NO 66
<211> LENGTH: 123
<212> TYPE: PRT
<213> ORGANISM: Homo sapiens

<400> SEQUENCE: 66

Glu Val Gln Leu Val Gln Ser Gly Ala Glu Val Lys Lys Pro Gly Glu
```

-continued

```
                 1               5                  10                 15
             Ser Leu Lys Ile Ser Cys Lys Gly Ser Gly Tyr Ser Phe Thr Ser Tyr
                             20                  25                 30

Trp Ile Gly Trp Val Arg Gln Met Pro Gly Lys Gly Leu Glu Trp Met
                             35                  40                 45

Gly Ile Ile Tyr Pro Gly Asp Ser Asp Thr Arg Tyr Ser Pro Ser Phe
                             50                  55                 60

Gln Gly Gln Val Thr Ile Ser Ala Asp Lys Ser Ile Ser Thr Ala Tyr
             65                          70                  75                 80

Leu Gln Trp Ser Ser Leu Lys Ala Ser Asp Thr Ala Met Tyr Tyr Cys
                             85                  90                 95

Ala Arg Val Tyr Ser Phe Gly Gly Arg His Lys Ala Leu Phe Asp Tyr
                            100                 105                110

Trp Gly Gln Gly Thr Leu Val Thr Val Ser Ser
                            115                 120
```

<210> SEQ ID NO 67
<211> LENGTH: 123
<212> TYPE: PRT
<213> ORGANISM: Homo sapiens

<400> SEQUENCE: 67

```
             Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Ser Gly Tyr
                             20                  25                 30

Ala Met Ser Trp Val Arg Gln Ala Pro Gly Lys Gly Leu Glu Trp Val
                             35                  40                 45

Ser Ala Ile Ser Gly Ser Gly Gly Ser Thr Tyr Tyr Ala Asp Ser Val
                             50                  55                 60

Lys Gly Arg Phe Thr Ile Ser Arg Asp Asn Ser Lys Asn Thr Leu Tyr
             65                          70                  75                 80

Leu Gln Met Asn Ser Leu Arg Ala Glu Asp Thr Ala Val Tyr Tyr Cys
                             85                  90                 95

Ala Lys Val Asp Arg Ser Phe Gly Arg Ser Arg Tyr Thr Leu Asp Tyr
                            100                 105                110

Trp Gly Gln Gly Thr Leu Val Thr Val Ser Ser
                            115                 120
```

<210> SEQ ID NO 68
<211> LENGTH: 123
<212> TYPE: PRT
<213> ORGANISM: Homo sapiens

<400> SEQUENCE: 68

```
             Gln Val Gln Leu Val Gln Ser Gly Ala Glu Val Lys Lys Pro Gly Ser
             1               5                  10                 15

Ser Val Lys Val Ser Cys Lys Ala Ser Gly Gly Thr Phe Ser Ser Tyr
                             20                  25                 30

Gly Ile Ser Trp Val Arg Gln Ala Pro Gly Gln Gly Leu Glu Trp Met
                             35                  40                 45

Gly Gly Ile Ile Pro Ile Phe Gly Asn Ile Asn Tyr Ala Gln Lys Phe
                             50                  55                 60

Gln Gly Arg Val Thr Ile Thr Ala Asp Glu Ser Thr Ser Thr Ala Tyr
             65                          70                  75                 80

Met Glu Leu Ser Ser Leu Arg Ser Glu Asp Thr Ala Val Tyr Tyr Cys
```

85                  90                  95
Ala Arg Val Ser Arg Arg Phe Lys Arg Phe Ala Tyr Tyr Phe Asp Tyr
                100                 105                 110

Trp Gly Gln Gly Thr Leu Val Thr Val Ser Ser
        115                 120

<210> SEQ ID NO 69
<211> LENGTH: 118
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Gly Asp Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
                100                 105                 110

Leu Val Thr Val Ser Ser
        115

<210> SEQ ID NO 70
<211> LENGTH: 119
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asn Phe Leu Pro Val Phe Asp Tyr Trp Gly Gln Gly
                100                 105                 110

Thr Leu Val Thr Val Ser Ser
        115

<210> SEQ ID NO 71
<211> LENGTH: 117
<212> TYPE: PRT
<213> ORGANISM: Homo sapiens

<400> SEQUENCE: 71

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Tyr
            20                  25                  30

Asn Val His Trp Ile Arg Gln Pro Pro Gly Lys Ala Leu Glu Trp Leu
        35                  40                  45

Ala Val Ile Trp Ala Gly Gly Ser Thr Asn Tyr Asn Ser Ala Leu Met
50                  55                  60

Ser Arg Leu Thr Ile Ser Lys Asp Thr Ser Lys Ser Gln Val Val Leu
65                  70                  75                  80

Thr Met Thr Asn Met Arg Ala Glu Asp Thr Ala Thr Tyr Tyr Cys Ala
                85                  90                  95

Arg Asp Gly Ile Arg Leu Arg Phe Ala Tyr Trp Gly Gln Gly Thr Leu
            100                 105                 110

Val Thr Val Ser Ser
        115

<210> SEQ ID NO 72
<211> LENGTH: 107
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 73
<211> LENGTH: 107
<212> TYPE: PRT
<213> ORGANISM: Homo sapiens

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95
```

Thr Phe Gly Gln Gly Thr Lys Val Glu Ile Lys
            100                 105

<210> SEQ ID NO 74
<211> LENGTH: 107
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
            20                  25                  30

Val Gly Trp Tyr Gln Gln Lys Pro Gly Lys Ala Pro Lys Arg Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 75
<211> LENGTH: 113
<212> TYPE: PRT
<213> ORGANISM: Homo sapiens

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 76
<211> LENGTH: 108
<212> TYPE: PRT
<213> ORGANISM: Homo sapiens

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Lys Ser
            20                  25                  30

Leu Ala Trp Tyr Gln Gln Lys Pro Gly Gln Ala Pro Arg Leu Leu Ile

```
                35                  40                  45

Tyr Thr Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Phe Arg Ala Pro Ile
                85                  90                  95

Thr Phe Gly Gln Gly Thr Lys Val Glu Ile Lys Lys
            100                 105

<210> SEQ ID NO 77
<211> LENGTH: 107
<212> TYPE: PRT
<213> ORGANISM: Homo sapiens

<400> SEQUENCE: 77

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Ala Thr His
                20                  25                  30

Val Gly Trp Tyr Gln Gln Lys Pro Gly Gln Ala Pro Arg Leu Leu Ile
            35                  40                  45

Tyr Ser Ala Ser Tyr Arg Tyr Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 78
<211> LENGTH: 120
<212> TYPE: PRT
<213> ORGANISM: Artificial sequence
<220> FEATURE:
<223> OTHER INFORMATION: Synthetic

<400> SEQUENCE: 78

Gln Val Gln Leu Val Gln Ser Gly Ser Glu Leu Lys Lys Pro Gly Ala
1               5                   10                  15

Ser Val Arg Val Ser Cys Thr Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Val Ile Asn Pro Asn Ala Gly Ser Thr Arg Tyr Ala Gln Lys Phe
        50                  55                  60

Gln Gly Arg Val Thr Met Ser Thr Asp Thr Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Met Tyr Arg Ser Leu Leu Phe Tyr Asp Pro Trp Gly Gln
            100                 105                 110

Gly Thr Leu Val Thr Val Ser Ser
        115                 120

<210> SEQ ID NO 79
```

```
<211> LENGTH: 116
<212> TYPE: PRT
<213> ORGANISM: Artificial sequence
<220> FEATURE:
<223> OTHER INFORMATION: Synthetic

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Val Arg Tyr Thr Asp Ile Trp Gly Gln Gly Thr Leu Val
            100                 105                 110

Thr Val Ser Ser
        115

<210> SEQ ID NO 80
<211> LENGTH: 119
<212> TYPE: PRT
<213> ORGANISM: Artificial sequence
<220> FEATURE:
<223> OTHER INFORMATION: Synthetic

<400> SEQUENCE: 80

Glu Val Gln Leu Val Gln Ser Gly Gly Gly Leu Val Gln Pro Gly Gly
1               5                   10                  15

Ser Leu Arg Leu Ser Cys Ala Thr Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Ala Asp Ser Val
    50                  55                  60

Arg Gly Arg Phe Thr Ile Ser Arg Asp Asn Ala Lys Asn Ser Leu Ser
65                  70                  75                  80

Leu Gln Leu Asn Asn Leu Arg Ala Glu Asp Thr Ala Val Tyr Tyr Cys
                85                  90                  95

Ala Arg Ser Met Ser Thr Ala Trp Gly Tyr Asp Glu Trp Gly Gln Gly
            100                 105                 110

Thr Leu Val Thr Val Ser Ser
        115

<210> SEQ ID NO 81
<211> LENGTH: 121
<212> TYPE: PRT
<213> ORGANISM: Artificial sequence
<220> FEATURE:
<223> OTHER INFORMATION: Synthetic

<400> SEQUENCE: 81

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ser Arg Trp Gly Gly Trp Thr Gly Asp Tyr Trp Gly
            100                 105                 110

Gln Gly Thr Leu Val Thr Val Ser Ser
        115                 120

<210> SEQ ID NO 82
<211> LENGTH: 117
<212> TYPE: PRT
<213> ORGANISM: Artificial sequence
<220> FEATURE:
<223> OTHER INFORMATION: Synthetic

<400> SEQUENCE: 82

Glu Val Gln Leu Val Glu Thr Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Lys Ser Ser Lys Asp His Trp Gly Gln Gly Thr Leu
            100                 105                 110

Val Thr Val Ser Ser
        115

<210> SEQ ID NO 83
<211> LENGTH: 121
<212> TYPE: PRT
<213> ORGANISM: Artificial sequence
<220> FEATURE:
<223> OTHER INFORMATION: Synthetic

<400> SEQUENCE: 83

Gln Val Gln Leu Val Gln Ser Gly Ala Glu Val Gln Arg Pro Gly Ala
1               5                   10                  15

Ser Val Arg Val Ser Cys Lys Ala Ile Ala Tyr Thr Phe Thr Asp Tyr
            20                  25                  30

Tyr Ile His Trp Val Arg Gln Ala Pro Gly Gly Gly Pro Glu Trp Met
        35                  40                  45

Gly Trp Ile Asn Pro Lys Ser Gly Arg Thr Gly Tyr Ala Pro Lys Phe
    50                  55                  60

Gln Asp Arg Val Thr Leu Ala Arg Glu Thr Pro Ile Ser Thr Ala Ser
65                  70                  75                  80

```
Met Glu Leu Arg Gly Leu Thr Ser Asp Asp Thr Ala Val Tyr Tyr Cys
                85                  90                  95

Ala Arg Val Tyr Gly Tyr Ser Arg Trp Ser Gly Phe Asp Leu Trp Gly
            100                 105                 110

Gln Gly Thr Leu Val Thr Val Ser Ser
        115                 120
```

<210> SEQ ID NO 84
<211> LENGTH: 124
<212> TYPE: PRT
<213> ORGANISM: Artificial sequence
<220> FEATURE:
<223> OTHER INFORMATION: Synthetic

<400> SEQUENCE: 84

```
Gln Val Gln Leu Val Gln Ser Gly Ala Glu Val Lys Gln Pro Gly Ala
1               5                   10                  15

Ser Val Lys Val Ser Cys Gln Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Asn Gly Gly Thr Phe Tyr Ala Gln Lys Phe
    50                  55                  60

Gln Asp Arg Val Thr Met Thr Arg Asp Thr Ser Thr Gly Thr Val Tyr
65                  70                  75                  80

Met Glu Leu Ser Ser Leu Arg Ser Asp Asp Thr Ala Val Tyr Tyr Cys
                85                  90                  95

Ala Arg Gly His Lys Val Tyr Lys Ser His Pro Thr Gly Gly Tyr Asp
            100                 105                 110

Arg Trp Gly Gln Gly Thr Leu Val Thr Val Ser Ser
        115                 120
```

<210> SEQ ID NO 85
<211> LENGTH: 119
<212> TYPE: PRT
<213> ORGANISM: Artificial sequence
<220> FEATURE:
<223> OTHER INFORMATION: Synthetic

<400> SEQUENCE: 85

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Val Ala Trp Ser Leu Leu Asp Tyr Trp Gly Gln Gly
            100                 105                 110

Thr Leu Val Thr Val Ser Ser
        115
```

<210> SEQ ID NO 86
<211> LENGTH: 120
<212> TYPE: PRT
<213> ORGANISM: Artificial sequence
<220> FEATURE:
<223> OTHER INFORMATION: Synthetic

<400> SEQUENCE: 86

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gln Ser Tyr Lys Gly Ser Gln Ser Asp Ser Trp Gly Gln
            100                 105                 110

Gly Thr Leu Val Thr Val Ser Ser
        115                 120
```

<210> SEQ ID NO 87
<211> LENGTH: 127
<212> TYPE: PRT
<213> ORGANISM: Artificial sequence
<220> FEATURE:
<223> OTHER INFORMATION: Synthetic

<400> SEQUENCE: 87

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Lys Lys Trp Ser Gly Glu Lys Trp Arg Arg Glu
            100                 105                 110

Asn Phe Asp Tyr Trp Gly Gln Gly Thr Leu Val Thr Val Ser Ser
        115                 120                 125
```

<210> SEQ ID NO 88
<211> LENGTH: 113
<212> TYPE: PRT
<213> ORGANISM: Artificial sequence
<220> FEATURE:
<223> OTHER INFORMATION: Synthetic

<400> SEQUENCE: 88

```
Gln Met Gln Leu Val Gln Ser Gly Ala Glu Val Lys Lys Pro Gly Ala
1               5                   10                  15
```

```
Ser Val Lys Val Ser Cys Lys Ala Ser Glu Tyr Thr Phe Thr Arg His
            20                  25                  30

Ile Leu His Trp Val Arg Gln Ala Pro Gly Gln Ser Leu Glu Trp Met
        35                  40                  45

Gly Trp Ile Asn Pro Gly Asn Gly Asn Thr Lys Tyr Ser Gln Lys Phe
50                  55                  60

Gln Val Arg Val Thr Phe Thr Arg Asp Thr Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Pro Asp Gln Trp Gly Gln Gly Thr Leu Val Thr Val Ser
            100                 105                 110

Ser
```

```
<210> SEQ ID NO 89
<211> LENGTH: 96
<212> TYPE: PRT
<213> ORGANISM: Artificial sequence
<220> FEATURE:
<223> OTHER INFORMATION: Synthetic

<400> SEQUENCE: 89
```

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
50                  55                  60

Leu Gln Met Asn Ser Leu Arg Ala Glu Asp Thr Ala Val Tyr Tyr Cys
65                  70                  75                  80

Ala Arg Ser Lys Gln Asp Tyr Trp Gly Gln Gly Thr Leu Val Thr Val
                85                  90                  95
```

```
<210> SEQ ID NO 90
<211> LENGTH: 114
<212> TYPE: PRT
<213> ORGANISM: Artificial sequence
<220> FEATURE:
<223> OTHER INFORMATION: Synthetic

<400> SEQUENCE: 90
```

```
Glu Val Gln Leu Val Glu Thr Gly Gly Asn Leu Val Gln Pro Gly Ala
1               5                   10                  15

Ser Leu Arg Leu Ser Cys Ala Ala Ser Gly Phe Ser Phe Ser Gly Thr
            20                  25                  30

Ala Met His Trp Val Arg Gln Ala Pro Gly Lys Gly Leu Glu Trp Val
        35                  40                  45

Ser Thr Ile Ser Ser Thr Gly Arg Ser Thr Tyr Tyr Arg Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Val Ser Phe Asp Tyr Trp Gly Gln Gly Thr Leu Val Thr Val
            100                 105                 110
```

Ser Ser

<210> SEQ ID NO 91
<211> LENGTH: 118
<212> TYPE: PRT
<213> ORGANISM: Artificial sequence
<220> FEATURE:
<223> OTHER INFORMATION: Synthetic

<400> SEQUENCE: 91

```
Glu Val Gln Leu Val Glu Ser Gly Gly Ala Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Ser Gly Arg Gly Arg Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr His Ala Gly Ala Phe Asp Leu Trp Gly Gln Gly Thr
            100                 105                 110

Leu Val Thr Val Ser Ser
        115
```

<210> SEQ ID NO 92
<211> LENGTH: 114
<212> TYPE: PRT
<213> ORGANISM: Artificial sequence
<220> FEATURE:
<223> OTHER INFORMATION: Synthetic

<400> SEQUENCE: 92

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Arg Tyr
            20                  25                  30

Ala Ile Thr Trp Val Arg Gln Ala Pro Gly Gln Gly Leu Glu Trp Met
        35                  40                  45

Gly Trp Ile Ser Ala Tyr Asn Gly Asn Ser His Tyr Ala Gln Lys Leu
    50                  55                  60

Gln Gly Arg Val Thr Met Thr Thr Asp Thr Ser Thr Gly Thr Ala Tyr
65                  70                  75                  80

Met Glu Leu Arg Arg Leu Arg Ser Asp Asp Thr Ala Val Tyr Tyr Cys
                85                  90                  95

Ala Arg Met Ala Tyr Asp Ser Trp Gly Gln Gly Thr Leu Val Thr Val
            100                 105                 110

Ser Ser
```

<210> SEQ ID NO 93
<211> LENGTH: 117
<212> TYPE: PRT
<213> ORGANISM: Artificial sequence
<220> FEATURE:
<223> OTHER INFORMATION: Synthetic

<400> SEQUENCE: 93

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Lys Ala Tyr Asp Gln Trp Gly Gln Gly Thr Leu
                100                 105                 110

Val Thr Val Ser Ser
            115
```

```
<210> SEQ ID NO 94
<211> LENGTH: 119
<212> TYPE: PRT
<213> ORGANISM: Artificial sequence
<220> FEATURE:
<223> OTHER INFORMATION: Synthetic

<400> SEQUENCE: 94
```

```
Gln Val Gln Leu Val Glu Ser Gly Gly Gly Leu Val His Pro Gly Gly
1               5                   10                  15

Ser Leu Arg Leu Ser Cys Ala Ala Ser Gly Phe Thr Phe Arg Ser His
            20                  25                  30

Ser Met Asn Trp Val Arg Gln Ala Pro Gly Lys Gly Leu Glu Trp Val
        35                  40                  45

Ser Ser Ile Ser Ser Asp Ser Thr Tyr Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Gly Trp Lys Tyr Tyr Asp Tyr Trp Gly Gln Gly
                100                 105                 110

Thr Leu Val Thr Val Ser Ser
            115
```

```
<210> SEQ ID NO 95
<211> LENGTH: 116
<212> TYPE: PRT
<213> ORGANISM: Artificial sequence
<220> FEATURE:
<223> OTHER INFORMATION: Synthetic

<400> SEQUENCE: 95
```

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Thr Ile Asn Gly Arg Gly Ser Ser Thr Ile Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Tyr Ile Ser Arg Gly Leu Gly Asp Ser Trp Gly Gln Gly Thr
                100                 105                 110

Leu Val Thr Val
        115

<210> SEQ ID NO 96
<211> LENGTH: 116
<212> TYPE: PRT
<213> ORGANISM: Artificial sequence
<220> FEATURE:
<223> OTHER INFORMATION: Synthetic

<400> SEQUENCE: 96

Gln Met Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ala Gly Met Gly Met Asp Thr Trp Gly Gln Gly Thr Leu Val
                100                 105                 110

Thr Val Ser Ser
        115

<210> SEQ ID NO 97
<211> LENGTH: 117
<212> TYPE: PRT
<213> ORGANISM: Artificial sequence
<220> FEATURE:
<223> OTHER INFORMATION: Synthetic

<400> SEQUENCE: 97

Gln Val Gln Leu Val Gln Ser Gly Ala Glu Val Lys Lys Pro Gly Ala
  1               5                  10                  15

Ser Val Lys Val Ser Cys Arg Ala Ser Gly Tyr Thr Phe Thr Ala Tyr
                 20                  25                  30

Ser Leu His Trp Val Arg Gln Ala Pro Gly Gln Gly Leu Glu Trp Met
             35                  40                  45

Gly Trp Ile Asn Pro Ser Ser Gly Gly Ala Val Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Gly Leu Arg Ser Asp Asp Thr Ala Val Tyr Tyr Cys
                 85                  90                  95

Ala Arg Asn Val Gly Gly Gln Ala Asp Asp Trp Gly Gln Gly Thr Leu
                100                 105                 110
```

Val Thr Val Ser Ser
        115

<210> SEQ ID NO 98
<211> LENGTH: 117
<212> TYPE: PRT
<213> ORGANISM: Artificial sequence
<220> FEATURE:
<223> OTHER INFORMATION: Synthetic

<400> SEQUENCE: 98

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Ala Tyr
            20                  25                  30

Ser Leu His Trp Val Arg Gln Ala Pro Gly Gln Gly Leu Glu Trp Met
        35                  40                  45

Gly Trp Ile Asn Pro Ser Ser Gly Gly Ala Val Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Asn Val Gly Gly His Ala Asp Asp Trp Gly Gln Gly Thr Leu
            100                 105                 110

Val Thr Val Ser Ser
        115

<210> SEQ ID NO 99
<211> LENGTH: 129
<212> TYPE: PRT
<213> ORGANISM: Artificial sequence
<220> FEATURE:
<223> OTHER INFORMATION: Synthetic

<400> SEQUENCE: 99

Gln Val Gln Leu Val Gln Ser Gly Gly Glu Val Lys Lys Pro Gly Ala
1               5                   10                  15

Ser Val Lys Val Ser Cys Lys Ala Ser Gly Phe Thr Phe Asn Thr Tyr
            20                  25                  30

Gly Ile Ser Trp Val Arg Gln Ala Pro Gly Gln Gly Leu Glu Trp Met
        35                  40                  45

Gly Trp Ile Ser Ala Asn Asn Gly His Thr Lys Ser Ala Gln Arg Phe
    50                  55                  60

Gln Asp Arg Val Ala Met Ala Thr Asp Thr Ser Thr Ser Thr Ala Tyr
65                  70                  75                  80

Met Glu Leu Arg Ser Leu Lys Phe Asp Asp Thr Ala Val Tyr Tyr Cys
                85                  90                  95

Ala Arg Gly Gly Tyr His His Gln Met Gln Arg Tyr Tyr Lys Ala Thr
            100                 105                 110

Ser Val Tyr Ser Asp Tyr Trp Gly Gln Gly Thr Leu Val Thr Val Ser
        115                 120                 125

Ser

<210> SEQ ID NO 100
<211> LENGTH: 116
<212> TYPE: PRT
<213> ORGANISM: Artificial sequence
<220> FEATURE:

<223> OTHER INFORMATION: Synthetic

<400> SEQUENCE: 100

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Gly Met Gly Met Asp Thr Trp Gly Gln Gly Thr Leu Val
            100                 105                 110

Thr Val Ser Ser
        115

<210> SEQ ID NO 101
<211> LENGTH: 117
<212> TYPE: PRT
<213> ORGANISM: Artificial sequence
<220> FEATURE:
<223> OTHER INFORMATION: Synthetic

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Ile Ser Gly Phe Asp Ser Trp Gly Gln Gly Thr Leu
            100                 105                 110

Val Thr Val Ser Ser
        115

<210> SEQ ID NO 102
<211> LENGTH: 114
<212> TYPE: PRT
<213> ORGANISM: Artificial sequence
<220> FEATURE:
<223> OTHER INFORMATION: Synthetic

<400> SEQUENCE: 102

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val

```
                35                  40                  45
Ser Gly Ile Asn Trp Asn Gly Gly Ser Thr Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Lys Gln Asp Tyr Trp Gly Gln Gly Thr Leu Val Thr Val
                100                 105                 110

Ser Ser

<210> SEQ ID NO 103
<211> LENGTH: 121
<212> TYPE: PRT
<213> ORGANISM: Artificial sequence
<220> FEATURE:
<223> OTHER INFORMATION: Synthetic

<400> SEQUENCE: 103

Gln Leu Gln Leu Gln Glu Ser Gly Gly Gly Ser Val Gln Pro Gly Gly
 1               5                  10                  15

Ser Leu Arg Leu Ser Cys Ala Ala Ser Gly Phe Thr Phe Ser Asn Tyr
                 20                  25                  30

Ala Met Ser Trp Val Arg Gln Ala Pro Gly Lys Gly Leu Glu Trp Val
             35                  40                  45

Ser Ala Ile Thr Asn Ser Gly Arg Ser Thr Tyr Tyr Ala Asp Ser Val
     50                  55                  60

Lys Gly Arg Phe Thr Ile Ser Arg Asp Asn Ser Lys Asn Thr Leu Ser
 65                  70                  75                  80

Leu Gln Met Ser Ser Leu Arg Ala Glu Asp Thr Ala Val Tyr Tyr Cys
                 85                  90                  95

Ala Arg Val Thr His Arg Arg Tyr Gly Ser Thr Phe Asp Ser Arg Gly
                100                 105                 110

Gln Gly Thr Leu Val Thr Val Ser Ser
        115                 120

<210> SEQ ID NO 104
<211> LENGTH: 121
<212> TYPE: PRT
<213> ORGANISM: Artificial sequence
<220> FEATURE:
<223> OTHER INFORMATION: Synthetic

<400> SEQUENCE: 104

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Ser Tyr
                 20                  25                  30

Ala Ile Thr Trp Val Arg Gln Ala Pro Gly Gln Gly Leu Glu Trp Met
             35                  40                  45

Gly Arg Ile Ile Pro Met Leu Asp Ile Thr Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Tyr Ser Arg Ser Pro Phe His Met Glu Asp Phe Trp Gly
```

```
                100             105              110
Gln Gly Thr Leu Val Thr Val Ser Ser
        115                 120

<210> SEQ ID NO 105
<211> LENGTH: 114
<212> TYPE: PRT
<213> ORGANISM: Artificial sequence
<220> FEATURE:
<223> OTHER INFORMATION: Synthetic

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Gln Asp Val Trp Gly Gln Gly Thr Leu Val Thr Val
            100                 105                 110

Ser Ser

<210> SEQ ID NO 106
<211> LENGTH: 122
<212> TYPE: PRT
<213> ORGANISM: Artificial sequence
<220> FEATURE:
<223> OTHER INFORMATION: Synthetic

<400> SEQUENCE: 106

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ser Phe Ser Gly Thr
            20                  25                  30

Ala Met His Trp Val Arg Gln Ala Pro Gly Lys Gly Leu Glu Trp Val
        35                  40                  45

Ser Thr Ile Ser Ser Thr Gly Arg Ser Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Pro Val Ser Ser Met Thr Leu Ser Ile Gln Ser Asp Gly Trp
            100                 105                 110

Gly Gln Gly Thr Leu Val Thr Val Ser Ser
        115                 120

<210> SEQ ID NO 107
<211> LENGTH: 130
<212> TYPE: PRT
<213> ORGANISM: Artificial sequence
<220> FEATURE:
<223> OTHER INFORMATION: Synthetic
```

<400> SEQUENCE: 107

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Lys Tyr His Ser Gln Tyr Ser Arg Gly Gly Thr Gly
            100                 105                 110

Gly Gly Met Thr Gln Asp Met Trp Gly Gln Gly Thr Leu Val Thr Val
            115                 120                 125

Ser Ser
    130

<210> SEQ ID NO 108
<211> LENGTH: 117
<212> TYPE: PRT
<213> ORGANISM: Artificial sequence
<220> FEATURE:
<223> OTHER INFORMATION: Synthetic

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Tyr Ile His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Tyr His Val Ile Asp Tyr Trp Gly Gln Gly Thr Leu
            100                 105                 110

Val Thr Val Ser Ser
        115

<210> SEQ ID NO 109
<211> LENGTH: 111
<212> TYPE: PRT
<213> ORGANISM: Artificial sequence
<220> FEATURE:
<223> OTHER INFORMATION: Synthetic

<400> SEQUENCE: 109

Gln Ser Val Leu Thr Gln Pro Pro Ser Val Ser Ala Ala Pro Gly Gln
1               5                   10                  15

Lys Val Thr Ile Pro Cys Ser Gly Ser Arg Ser Asn Val Gly Asn Tyr
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Gly Ser Leu
                85                  90                  95

Ser Ala His Val Phe Gly Thr Gly Thr Lys Val Thr Val Leu Gly
            100                 105                 110

<210> SEQ ID NO 110
<211> LENGTH: 113
<212> TYPE: PRT
<213> ORGANISM: Artificial sequence
<220> FEATURE:
<223> OTHER INFORMATION: Synthetic

<400> SEQUENCE: 110

Asn Phe Met Leu Thr Gln Pro His Ser Val Ser Glu Ser Pro Gly Lys
1               5                   10                  15

Thr Val Ser Ile Ser Cys Thr Arg Thr Ser Gly Ala Ile Ala Gly Ala
            20                  25                  30

Tyr Val Gln Trp Phe Gln Gln Arg Pro Gly Ser Ala Pro Thr Thr Val
            35                  40                  45

Ile Tyr Asp Asp Asn Lys Arg Pro Ser Gly Val Pro Asp Arg Phe Ser
 50                  55                  60

Gly Ser Ile Asp Lys Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Tyr
                85                  90                  95

Asp Ser Ser Asn Val Leu Phe Gly Gly Gly Thr Lys Leu Thr Val Leu
            100                 105                 110

Gly

<210> SEQ ID NO 111
<211> LENGTH: 108
<212> TYPE: PRT
<213> ORGANISM: Artificial sequence
<220> FEATURE:
<223> OTHER INFORMATION: Synthetic

<400> SEQUENCE: 111

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Ala Asp Phe Ala Thr Tyr Tyr Cys Gln Gln Ser Tyr Ser Val Pro Tyr
                85                  90                  95

Thr Phe Gly Gln Gly Thr Lys Leu Glu Ile Lys Arg
            100                 105

<210> SEQ ID NO 112
<211> LENGTH: 111
<212> TYPE: PRT
<213> ORGANISM: Artificial sequence
<220> FEATURE:
<223> OTHER INFORMATION: Synthetic

<400> SEQUENCE: 112

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Val
        35                  40                  45

Met Ile Tyr Asp Val Ser Lys Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Glu Tyr Tyr Cys Ser Ser Tyr Thr Ser Thr
                85                  90                  95

Arg Thr Val Ile Phe Ala Gly Gly Thr Lys Val Thr Val Leu Gly
            100                 105                 110
```

<210> SEQ ID NO 113
<211> LENGTH: 111
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (37)..(37)
<223> OTHER INFORMATION: Xaa can be any naturally occurring amino acid

<400> SEQUENCE: 113

```
Gln Ser Val Leu Thr Gln Pro Pro Ser Leu Ser Gly Ala Pro Gly Gln
1               5                   10                  15

Arg Val Thr Ile Ser Cys Ser Gly Ser Arg Ser Asn Ile Gly Thr Asn
            20                  25                  30

Tyr Val Ser Trp Xaa Gln Gln Leu Pro Gly Thr Ala Pro Lys Leu Leu
        35                  40                  45

Ile Tyr Arg Asn His Gln Trp Pro Ser Gly Val Pro Asp Arg Phe Thr
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Val Val Phe Gly Gly Gly Thr Lys Leu Thr Val Leu Gly
            100                 105                 110
```

<210> SEQ ID NO 114
<211> LENGTH: 111
<212> TYPE: PRT
<213> ORGANISM: Artificial sequence
<220> FEATURE:
<223> OTHER INFORMATION: Synthetic

<400> SEQUENCE: 114

```
Gln Ala Val Leu Thr Gln Pro Pro Ser Ala Ser Gly Thr Pro Gly Gln
1               5                   10                  15
```

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 115
<211> LENGTH: 111
<212> TYPE: PRT
<213> ORGANISM: Artificial sequence
<220> FEATURE:
<223> OTHER INFORMATION: Synthetic

<400> SEQUENCE: 115

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Phe Gly Thr Gly Thr Lys Val Thr Val Leu Gly
            100                 105                 110

<210> SEQ ID NO 116
<211> LENGTH: 111
<212> TYPE: PRT
<213> ORGANISM: Artificial sequence
<220> FEATURE:
<223> OTHER INFORMATION: Synthetic

<400> SEQUENCE: 116

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu Gly

<210> SEQ ID NO 117
<211> LENGTH: 111
<212> TYPE: PRT
<213> ORGANISM: Artificial sequence
<220> FEATURE:
<223> OTHER INFORMATION: Synthetic

<400> SEQUENCE: 117

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
            100                 105                 110

<210> SEQ ID NO 118
<211> LENGTH: 111
<212> TYPE: PRT
<213> ORGANISM: Artificial sequence
<220> FEATURE:
<223> OTHER INFORMATION: Synthetic

<400> SEQUENCE: 118

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
                85                  90                  95

Ser Thr Glu Val Phe Gly Gly Gly Thr Lys Leu Thr Val Leu Gly
            100                 105                 110

<210> SEQ ID NO 119
<211> LENGTH: 110
<212> TYPE: PRT
<213> ORGANISM: Artificial sequence
<220> FEATURE:
<223> OTHER INFORMATION: Synthetic

<400> SEQUENCE: 119

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Leu Phe Gly Thr Gly Thr Lys Val Thr Val Leu Gly
            100                 105                 110

<210> SEQ ID NO 120
<211> LENGTH: 112
<212> TYPE: PRT
<213> ORGANISM: Artificial sequence
<220> FEATURE:
<223> OTHER INFORMATION: Synthetic

<400> SEQUENCE: 120

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Arg Asp Ala Gly Gly Tyr
            20                  25                  30

Asn Tyr Phe Ser Trp Tyr Gln Gln His Pro Gly Lys Ala Pro Lys Leu
        35                  40                  45

Leu Ile Tyr Glu Val Thr Lys Arg Pro Ser Gly Val Pro Asp Arg Phe
    50                  55                  60

Ser Gly Ser Lys Ser Gly Lys Thr Ala Ser Leu Thr Val Ser Gly Leu
65                  70                  75                  80

Gln Ala Asp Asp Glu Ala Val Tyr Tyr Cys Ser Ser Tyr Gly Gly Ser
                85                  90                  95

Asn Asn Phe Arg Val Phe Gly Gly Gly Thr Lys Leu Thr Val Leu Gly
            100                 105                 110

<210> SEQ ID NO 121
<211> LENGTH: 113
<212> TYPE: PRT
<213> ORGANISM: Artificial sequence
<220> FEATURE:
<223> OTHER INFORMATION: Synthetic

<400> SEQUENCE: 121

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Tyr Val Phe Gly Thr Gly Thr Lys Leu Thr Val Leu
            100                 105                 110

Gly

<210> SEQ ID NO 122
<211> LENGTH: 118
<212> TYPE: PRT
<213> ORGANISM: Artificial sequence
<220> FEATURE:
<223> OTHER INFORMATION: Synthetic

<400> SEQUENCE: 122

```
Glu Val Gln Leu Val Glu Ser Gly Gly Ala Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Ser Gly Arg Gly Arg Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr His Ala Gly Ala Phe Asp Leu Trp Gly Gln Gly Thr
            100                 105                 110

Leu Val Thr Val Ser Ser
        115
```

<210> SEQ ID NO 123
<211> LENGTH: 111
<212> TYPE: PRT
<213> ORGANISM: Artificial sequence
<220> FEATURE:
<223> OTHER INFORMATION: Synthetic

<400> SEQUENCE: 123

```
Gln Ser Val Leu Thr Gln Pro Ala Ser Val Ser Gly Ser Pro Gly Gln
1               5                   10                  15

Ser Leu Thr Ile Ser Cys Thr Gly Thr Ser Asn Asp Val Gly Ala Tyr
            20                  25                  30

Lys Tyr Val Ser Trp Tyr Gln Gln Tyr Pro Gly Lys Ala Pro Lys Leu
        35                  40                  45

Ile Leu Tyr Asp Val Phe Lys Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Phe Ser Leu Thr Ser Ser
                85                  90                  95

Asn Thr Tyr Val Phe Gly Thr Gly Thr Lys Val Thr Val Leu Gly
            100                 105                 110
```

<210> SEQ ID NO 124
<211> LENGTH: 111
<212> TYPE: PRT
<213> ORGANISM: Artificial sequence
<220> FEATURE:
<223> OTHER INFORMATION: Synthetic

<400> SEQUENCE: 124

```
Gln Ser Val Leu Thr Gln Pro Pro Ser Ala Ser Gly Thr Pro Gly Gln
1               5                   10                  15
```

```
Arg Val Thr Ile Ser Cys Ser Gly Ser Arg Ser Asn Val Gly Asn
            20                  25                  30

Tyr Val Phe Trp Tyr Gln Gln Val Pro Gly Ala Thr Pro Lys Leu Leu
            35                  40                  45

Ile Tyr Arg Ser Asn Gln Arg Pro Ser Gly Val Pro Asp Arg Phe Ala
 50                      55                  60

Gly Ser Lys Ser Gly Ser Ser Ala Ser Leu Ala Ile Ser Gly Leu Arg
 65                  70                  75                  80

Ser Glu Asp Glu Ala Asp Tyr Tyr Cys Ala Thr Trp Asp Ser Leu
                 85                  90                  95

Ser Gly Phe Val Phe Gly Thr Gly Thr Lys Val Thr Val Leu Gly
            100                 105                 110
```

<210> SEQ ID NO 125
<211> LENGTH: 119
<212> TYPE: PRT
<213> ORGANISM: Artificial sequence
<220> FEATURE:
<223> OTHER INFORMATION: Synthetic

<400> SEQUENCE: 125

```
Gln Val Gln Leu Val Glu Ser Gly Gly Gly Leu Val His Pro Gly Gly
 1               5                  10                  15

Ser Leu Arg Leu Ser Cys Ala Ala Ser Gly Phe Thr Phe Arg Ser His
            20                  25                  30

Ser Met Asn Trp Val Arg Gln Ala Pro Gly Lys Gly Leu Glu Trp Val
            35                  40                  45

Ser Ser Ile Ser Ser Asp Ser Thr Tyr Thr Tyr Tyr Ala Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Gly Gln Trp Lys Tyr Tyr Asp Tyr Trp Gly Gln Gly
            100                 105                 110

Thr Leu Val Thr Val Ser Ser
            115
```

<210> SEQ ID NO 126
<211> LENGTH: 111
<212> TYPE: PRT
<213> ORGANISM: Artificial sequence
<220> FEATURE:
<223> OTHER INFORMATION: Synthetic

<400> SEQUENCE: 126

```
Gln Ser Val Val Thr Gln Pro Pro Ser Met Ser Ala Ala Pro Gly Gln
 1               5                  10                  15

Gln Val Thr Ile Ser Cys Ser Gly Gly Asn Ser Asn Ile Glu Arg Asn
            20                  25                  30

Tyr Val Ser Trp Tyr Leu Gln Leu Pro Gly Thr Ala Pro Lys Leu Val
            35                  40                  45

Ile Phe Asp Asn Asp Arg Arg Pro Ser Gly Ile Pro Arg Phe Ser
 50                      55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95
```

```
Arg Gly Trp Val Phe Gly Gly Gly Thr Lys Leu Thr Val Leu Gly
            100                 105                 110
```

<210> SEQ ID NO 127
<211> LENGTH: 111
<212> TYPE: PRT
<213> ORGANISM: Artificial sequence
<220> FEATURE:
<223> OTHER INFORMATION: Synthetic

<400> SEQUENCE: 127

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly
            100                 105                 110
```

<210> SEQ ID NO 128
<211> LENGTH: 111
<212> TYPE: PRT
<213> ORGANISM: Artificial sequence
<220> FEATURE:
<223> OTHER INFORMATION: Synthetic

<400> SEQUENCE: 128

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95

Lys Thr Leu Val Phe Gly Gly Gly Thr Lys Leu Thr Val Leu Gly
            100                 105                 110
```

<210> SEQ ID NO 129
<211> LENGTH: 111
<212> TYPE: PRT
<213> ORGANISM: Artificial sequence
<220> FEATURE:
<223> OTHER INFORMATION: Synthetic

<400> SEQUENCE: 129

```
Gln Ser Ala Leu Thr Gln Pro Pro Ser Ala Ser Gly Ser Pro Gly Gln
1               5                   10                  15
```

Ser Val Thr Ile Ser Cys Thr Gly Thr Ser Thr Asp Ile Gly Gly Tyr
            20                  25                  30

Asn Tyr Val Ser Trp Tyr Gln His His Pro Ser Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Phe Ala Gly Arg
                85                  90                  95

Lys Thr Leu Val Phe Gly Gly Gly Thr Lys Leu Thr Val Leu Gly
            100                 105                 110

<210> SEQ ID NO 130
<211> LENGTH: 111
<212> TYPE: PRT
<213> ORGANISM: Artificial sequence
<220> FEATURE:
<223> OTHER INFORMATION: Synthetic

<400> SEQUENCE: 130

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
            100                 105                 110

<210> SEQ ID NO 131
<211> LENGTH: 111
<212> TYPE: PRT
<213> ORGANISM: Artificial sequence
<220> FEATURE:
<223> OTHER INFORMATION: Synthetic

<400> SEQUENCE: 131

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Leu Val Phe Gly Gly Gly Thr Lys Leu Thr Val Leu Gly
            100                 105                 110

<210> SEQ ID NO 132
<211> LENGTH: 111
<212> TYPE: PRT
<213> ORGANISM: Artificial sequence
<220> FEATURE:
<223> OTHER INFORMATION: Synthetic

<400> SEQUENCE: 132

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Ser Pro Gly Lys Ala Pro Arg Leu
        35                  40                  45

Met Ile Tyr Gly Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Val
                85                  90                  95

Asn Asn Leu Met Phe Gly Gly Gly Thr Lys Leu Thr Val Leu Gly
            100                 105                 110
```

<210> SEQ ID NO 133
<211> LENGTH: 136
<212> TYPE: PRT
<213> ORGANISM: Artificial sequence
<220> FEATURE:
<223> OTHER INFORMATION: Synthetic

<400> SEQUENCE: 133

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Ala Leu Thr Gln Pro Pro
            20                  25                  30

Ser Ala Ser Gly Ser Pro Gly Gln Ser Val Thr Ile Ser Cys Thr Gly
        35                  40                  45

Thr Ser Arg Asp Ala Gly Gly Tyr Asn Tyr Phe Ser Trp Tyr Gln Gln
    50                  55                  60

His Pro Gly Lys Ala Pro Lys Leu Leu Ile Tyr Glu Val Thr Lys Arg
65                  70                  75                  80

Pro Ser Gly Val Pro Asp Arg Phe Ser Gly Ser Lys Ser Gly Lys Thr
                85                  90                  95

Ala Ser Leu Thr Val Ser Gly Leu Gln Ala Asp Asp Glu Ala Val Tyr
            100                 105                 110

Tyr Cys Ser Ser Tyr Gly Gly Ser Asn Asn Phe Arg Val Phe Gly Gly
        115                 120                 125

Gly Thr Lys Leu Thr Val Leu Gly
    130                 135
```

<210> SEQ ID NO 134
<211> LENGTH: 135
<212> TYPE: PRT
<213> ORGANISM: Artificial sequence
<220> FEATURE:
<223> OTHER INFORMATION: Synthetic

<400> SEQUENCE: 134

```
Met Lys Lys Thr Ala Ile Ala Ile Ala Val Ala Leu Ala Gly Phe Ala
1               5                   10                  15

Thr Val Ala Gln Ala Ala Glu Leu Ser Tyr Glu Leu Thr Gln Pro Pro
            20                  25                  30

Ser Ala Ser Gly Thr Pro Gly Gln Arg Val Ser Ile Ser Cys Ser Gly
        35                  40                  45

Ser Ser Ser Asn Ile Gly Ser Asn Thr Val Asn Trp Tyr Gln Gln Phe
    50                  55                  60

Pro Gly Thr Ala Pro Lys Leu Leu Ile His Ser Asn Asn Gln Arg Pro
65                  70                  75                  80

Ser Gly Val Pro Asp Arg Phe Ser Gly Ser Lys Ser Gly Thr Ser Ala
                85                  90                  95

Ser Leu Ala Ile Ser Gly Pro Gln Ser Glu Asp Glu Ala Asp Tyr Tyr
                100                 105                 110

Cys Ala Ala Trp Asp Asp Ser Val Asn Gly Tyr Val Phe Gly Thr Gly
                115                 120                 125

Thr Lys Val Thr Val Leu Gly
    130                 135
```

<210> SEQ ID NO 135
<211> LENGTH: 134
<212> TYPE: PRT
<213> ORGANISM: Artificial sequence
<220> FEATURE:
<223> OTHER INFORMATION: Synthetic

<400> SEQUENCE: 135

```
Met Lys Lys Thr Ala Ile Ala Ile Ala Val Ala Leu Ala Gly Phe Ala
1               5                   10                  15

Thr Val Ala Gln Ala Ala Glu Leu Gln Pro Val Leu Thr Gln Pro Pro
            20                  25                  30

Ser Ala Ser Gly Thr Pro Gly Gln Arg Val Thr Ile Ser Cys Ser Gly
        35                  40                  45

Ser Ser Ser Asn Ile Gly Gly Asn Thr Val Ser Trp Tyr Gln Gln Val
    50                  55                  60

Pro Gly Thr Ala Pro Arg Leu Leu Ile Phe Arg Asn Asn Gln Arg Pro
65                  70                  75                  80

Pro Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
                100                 105                 110

Cys Ala Ala Trp Asp Ala Ser Arg Gln Gly Val Phe Gly Gly Gly Thr
                115                 120                 125

Lys Leu Thr Val Leu Gly
    130
```

<210> SEQ ID NO 136
<211> LENGTH: 135
<212> TYPE: PRT
<213> ORGANISM: Artificial sequence
<220> FEATURE:
<223> OTHER INFORMATION: Synthetic

<400> SEQUENCE: 136

```
Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30
```

Ser Ala Ser Gly Thr Pro Gly Gln Arg Val Thr Ile Ser Cys Ser Gly
        35                  40                  45

Ser Ser Ser Asn Ile Gly Ser Asn Thr Val Asn Trp Tyr Gln Gln Leu
    50                  55                  60

Pro Gly Thr Ala Pro Lys Leu Leu Ile Tyr Arg Asn Asn Gln Arg Pro
65                  70                  75                  80

Ser Gly Val Pro Asp Arg Phe Ser Gly Ser Lys Ser Gly Thr Ser Ala
                85                  90                  95

Ser Leu Ala Ile Ser Gly Leu Arg Ser Glu Asp Glu Ala Asp Tyr Tyr
            100                 105                 110

Cys Ala Ala Trp Asp Asp Ser Leu Ser Gly Arg Val Phe Gly Gly Gly
            115                 120                 125

Thr Lys Leu Thr Val Leu Gly
        130             135

<210> SEQ ID NO 137
<211> LENGTH: 136
<212> TYPE: PRT
<213> ORGANISM: Artificial sequence
<220> FEATURE:
<223> OTHER INFORMATION: Synthetic

<400> SEQUENCE: 137

Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Val Ser Gly Ala Pro Gly Gln Arg Val Thr Ile Ser Cys Thr Gly
        35                  40                  45

Ser Ser Ser Asn Ile Gly Ala Gly Tyr Asp Val His Trp Tyr Gln Gln
    50                  55                  60

Leu Pro Gly Arg Ala Pro Lys Leu Leu Ile Tyr Gly Asn Ser Asn Arg
65                  70                  75                  80

Pro Ser Gly Val Pro Asp Arg Phe Ser Gly Ser Lys Ser Gly Thr Ser
                85                  90                  95

Ala Ser Leu Ala Ile Thr Gly Leu Gln Ala Glu Asp Glu Ala Asp Tyr
            100                 105                 110

Tyr Cys Gln Ser Tyr Asp Ser Ser Leu Arg Gly Tyr Val Phe Gly Thr
            115                 120                 125

Gly Thr Lys Val Thr Val Leu Gly
        130             135

<210> SEQ ID NO 138
<211> LENGTH: 135
<212> TYPE: PRT
<213> ORGANISM: Artificial sequence
<220> FEATURE:
<223> OTHER INFORMATION: Synthetic

<400> SEQUENCE: 138

Met Lys Lys Thr Ala Ile Ala Ile Ala Val Ala Leu Ala Gly Phe Ala
1               5                   10                  15

Thr Val Ala Gln Ala Ala Glu Leu Gln Ser Val Val Thr Gln Pro Pro
            20                  25                  30

Ser Val Ser Ala Ala Pro Gly Gln Arg Val Thr Ile Ser Cys Ser Gly
        35                  40                  45

Gly Ser Ser Asn Ile Gly Asn Asn Tyr Val Ser Trp Phe Gln Gln Leu

```
                    50                  55                  60
Pro Arg Thr Ala Pro Lys Leu Leu Ile Tyr Asp Asn Asn Lys Arg Pro
65                  70                  75                  80

Ser Gly Ile Pro Asp Arg Phe Ser Gly Ser Lys Ser Gly Thr Ser Ala
                85                  90                  95

Ala Leu Asp Ile Thr Val Leu Gln Thr Gly Asp Glu Ala Asp Tyr Tyr
            100                 105                 110

Cys Gly Thr Trp Asp Ser Ser Leu Arg Asn Trp Val Phe Gly Gly Gly
            115                 120                 125

Thr Lys Leu Thr Val Leu Gly
        130                 135

<210> SEQ ID NO 139
<211> LENGTH: 135
<212> TYPE: PRT
<213> ORGANISM: Artificial sequence
<220> FEATURE:
<223> OTHER INFORMATION: Synthetic

<400> SEQUENCE: 139

Met Lys Lys Thr Ala Ile Ala Ile Ala Val Ala Leu Ala Gly Phe Ala
1               5                   10                  15

Thr Val Ala Gln Ala Ala Glu Leu Gln Ser Val Leu Thr Gln Pro Pro
            20                  25                  30

Ser Ala Ser Gly Ser Pro Gly Gln Ser Leu Thr Ile Ser Cys Thr Gly
            35                  40                  45

Thr Ser Ser Asp Val Gly Gly Tyr Asn His Val Ser Trp Tyr Gln Gln
        50                  55                  60

Tyr Pro Gly Lys Ala Pro Lys Leu Met Ile Tyr Glu Val Thr Lys Arg
65                  70                  75                  80

Pro Ser Gly Val Pro Asp Arg Phe Ser Gly Ser Lys Ser Gly Asn Thr
                85                  90                  95

Ala Ser Leu Thr Val Ser Gly Leu Gln Ala Glu Asp Glu Ala Asp Tyr
            100                 105                 110

Tyr Cys Ser Ser Tyr Ala Gly Ser Ala His Trp Val Phe Gly Gly Gly
            115                 120                 125

Thr Lys Leu Thr Val Leu Gly
        130                 135
```